(12) United States Patent
Dupray et al.

(10) Patent No.: US 8,961,172 B2
(45) Date of Patent: *Feb. 24, 2015

(54) SELF LIGATING ORTHODONTIC BRACKET HAVING A ROTATABLE MEMBER

(71) Applicant: RMO, Inc., Denver, CO (US)

(72) Inventors: Dennis J. Dupray, Golden, CO (US); Nam Trinh, Highlands Ranch, CO (US); Jeffrey Allen Smith, Denver, CO (US)

(73) Assignee: RMO, Inc., Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/223,194

(22) Filed: Mar. 24, 2014

(65) Prior Publication Data

US 2014/0205961 A1    Jul. 24, 2014

Related U.S. Application Data

(63) Continuation of application No. 13/766,997, filed on Feb. 14, 2013, now Pat. No. 8,678,818, which is a continuation of application No. 13/117,085, filed on May 26, 2011, now Pat. No. 8,376,739.

(60) Provisional application No. 61/518,927, filed on May 12, 2011.

(51) Int. Cl.
*A61C 3/00* (2006.01)
*A61C 7/28* (2006.01)
(Continued)

(52) U.S. Cl.
CPC .............. *A61C 7/285* (2013.01); *A61C 7/143* (2013.01); *A61C 7/16* (2013.01); *A61C 7/28* (2013.01)
USPC .......................................................... 433/10

(58) Field of Classification Search
USPC ....................................................... 433/8–17
See application file for complete search history.

(56) References Cited

U.S. PATENT DOCUMENTS

| 626,476 A | 6/1899 | Angle |
| 1,890,487 A | 12/1932 | Angle |
| 2,011,575 A | 8/1935 | Ford |

(Continued)

FOREIGN PATENT DOCUMENTS

| DE | 8903611 | 8/1990 |
| DE | 69228472 | 10/1999 |

(Continued)

OTHER PUBLICATIONS

U.S. Appl. No. 10/821,699, filed Apr. 9, 2004, Ricketts.
(Continued)

*Primary Examiner* — Eric Rosen
(74) *Attorney, Agent, or Firm* — Sheridan Ross P.C.

(57) ABSTRACT

The present disclosure is directed, at least in part, to a self ligating orthodontic bracket having a rotatable member for securing an archwire within a slot of the bracket. Embodiments of the orthodontic bracket disclosed herein include a bracket body containing the archwire slot as well as tie wings for attaching various orthodontic devices (e.g., elastomeric bands) to the bracket. The rotatable member is rotatable in a first direction (e.g., counter clockwise) relative to a body of the bracket for securing or locking the archwire within the slot, and for rotating in an opposite direction (e.g., a clockwise direction) relative to the bracket body for unsecuring or unlocking the archwire so that it is substantially unrestrained from exiting the slot.

20 Claims, 61 Drawing Sheets

(51) Int. Cl.
*A61C 7/14* (2006.01)
*A61C 7/16* (2006.01)

(56) References Cited

U.S. PATENT DOCUMENTS

| | | |
|---|---|---|
| 2,104,192 A | 1/1938 | Ford |
| 2,196,515 A | 4/1940 | Atkinson |
| 3,028,671 A | 4/1962 | Berger |
| 3,055,110 A | 9/1962 | Kesling |
| 3,158,934 A | 12/1964 | Waldman |
| 3,193,930 A | 7/1965 | Bien |
| 3,391,461 A | 7/1968 | Johnson |
| 3,435,527 A | 4/1969 | Kesling |
| 3,494,034 A | 2/1970 | Kesling |
| 3,504,438 A | 4/1970 | Wittman et al. |
| 3,526,961 A | 9/1970 | Kesling |
| 3,765,091 A | 10/1973 | Northcutt |
| 3,798,773 A | 3/1974 | Northcutt |
| 3,838,514 A | 10/1974 | Polak |
| 3,854,207 A | 12/1974 | Wildman |
| 3,874,080 A | 4/1975 | Wallshein |
| 3,916,526 A | 11/1975 | Schudy |
| 3,964,156 A | 6/1976 | Williams et al. |
| 3,975,824 A | 8/1976 | Lee |
| 3,985,282 A | 10/1976 | Miller et al. |
| 3,987,547 A | 10/1976 | Moss |
| 4,015,334 A | 4/1977 | Moss |
| 4,028,809 A | 6/1977 | Wallshein |
| 4,083,113 A | 4/1978 | Miller et al. |
| 4,103,423 A | 8/1978 | Kessel |
| 4,134,208 A | 1/1979 | Pearlman |
| 4,171,568 A | 10/1979 | Forster |
| 4,172,999 A | 10/1979 | Leidich |
| 4,183,141 A | 1/1980 | Dellinger et al. |
| 4,192,070 A | 3/1980 | Lemchen et al. |
| 4,193,195 A | 3/1980 | Merkel et al. |
| 4,197,642 A | 4/1980 | Wallshein |
| 4,212,638 A | 7/1980 | Korn |
| 4,219,617 A | 8/1980 | Wallshein |
| D256,950 S | 9/1980 | Sable |
| 4,242,085 A | 12/1980 | Wallshein |
| 4,248,587 A | 2/1981 | Kurz |
| 4,260,375 A | 4/1981 | Wallshein |
| 4,284,405 A | 8/1981 | Dellinger |
| 4,299,569 A | 11/1981 | Frantz |
| 4,302,532 A | 11/1981 | Wallshein |
| 4,322,206 A | 3/1982 | Reynolds |
| 4,350,487 A | 9/1982 | Kesling et al. |
| 4,354,834 A | 10/1982 | Wilson |
| 4,386,908 A | 6/1983 | Kurz |
| 4,415,330 A | 11/1983 | Daisley et al. |
| 4,419,078 A | 12/1983 | Pletcher |
| 4,430,061 A | 2/1984 | Webb et al. |
| 4,455,137 A | 6/1984 | Diamond |
| 4,462,800 A | 7/1984 | Jones |
| 4,478,577 A | 10/1984 | Warren, Jr. |
| 4,498,867 A | 2/1985 | Kesling |
| 4,511,331 A | 4/1985 | Scebold et al. |
| 4,527,975 A | 7/1985 | Ghafari et al. |
| 4,529,382 A | 7/1985 | Creekmore |
| 4,531,911 A | 7/1985 | Creekmore |
| 4,531,991 A | 7/1985 | Ziemek et al. |
| 4,545,760 A | 10/1985 | Forster |
| 4,551,095 A | 11/1985 | Mason |
| 4,575,337 A | 3/1986 | Fujita |
| 4,626,209 A | 12/1986 | Tsai et al. |
| 4,639,218 A | 1/1987 | Jones et al. |
| 4,659,309 A | 4/1987 | Merkel |
| 4,661,059 A | 4/1987 | Kanno |
| D290,040 S | 5/1987 | Kelly |
| 4,669,979 A | 6/1987 | Snead |
| 4,669,981 A | 6/1987 | Kurz |
| D291,919 S | 9/1987 | Reynolds |
| 4,700,697 A | 10/1987 | Mundell et al. |
| 4,712,999 A | 12/1987 | Rosenberg |
| 4,752,221 A | 6/1988 | Hanson et al. |
| 4,773,853 A | 9/1988 | Kussick |
| 4,781,334 A | 11/1988 | Derichs |
| 4,781,582 A | 11/1988 | Kesling |
| 4,793,804 A | 12/1988 | Schudy |
| 4,795,342 A | 1/1989 | Jones |
| 4,799,882 A | 1/1989 | Kesling |
| 4,819,316 A | 4/1989 | Rossini et al. |
| 4,820,151 A | 4/1989 | Pospisil |
| 4,838,786 A | 6/1989 | Reher et al. |
| 4,854,866 A | 8/1989 | Wilson |
| 4,859,179 A | 8/1989 | Kesling |
| 4,900,251 A | 2/1990 | Andreasen |
| 4,917,602 A | 4/1990 | Broussard |
| 4,927,360 A | 5/1990 | Pospisil |
| 4,927,362 A | 5/1990 | Snead |
| 4,954,080 A | 9/1990 | Kelly et al. |
| 4,963,092 A | 10/1990 | Snead |
| 4,975,052 A | 12/1990 | Spencer et al. |
| 4,997,182 A | 3/1991 | Kussick |
| 5,022,854 A | 6/1991 | Broughton et al. |
| 5,030,089 A | 7/1991 | Kawaguchi |
| 5,035,614 A | 7/1991 | Greenfield |
| 5,044,945 A | 9/1991 | Peterson |
| 5,057,012 A | 10/1991 | Kesling |
| 5,059,119 A | 10/1991 | Snead |
| 5,062,794 A | 11/1991 | Miura |
| 5,066,225 A | 11/1991 | Forbes Jones et al. |
| D322,482 S | 12/1991 | Ianieri et al. |
| 5,095,602 A | 3/1992 | Reher et al. |
| 5,120,218 A | 6/1992 | Hanson |
| 5,125,831 A | 6/1992 | Pospisil |
| 5,125,832 A | 6/1992 | Kesling |
| 5,127,828 A | 7/1992 | Suyama |
| 5,133,740 A | 7/1992 | Kussick |
| 5,151,028 A | 9/1992 | Snead |
| 5,154,607 A | 10/1992 | Hanson |
| 5,158,452 A | 10/1992 | Franseen et al. |
| 5,160,261 A | 11/1992 | Peterson |
| 5,161,969 A | 11/1992 | Pospisil et al. |
| D331,975 S | 12/1992 | Pospisil |
| 5,183,388 A | 2/1993 | Kumar |
| 5,203,804 A | 4/1993 | Nikutowski et al. |
| 5,224,858 A | 7/1993 | Hanson |
| 5,226,814 A | 7/1993 | Allen |
| 5,230,620 A | 7/1993 | Watanabe |
| 5,238,402 A | 8/1993 | Rohlcke et al. |
| 5,242,299 A | 9/1993 | Yoshida |
| D340,523 S | 10/1993 | Barngrover |
| 5,252,066 A | 10/1993 | Fairhurst |
| 5,254,002 A | 10/1993 | Reher et al. |
| 5,267,855 A | 12/1993 | Tuneberg |
| 5,269,680 A | 12/1993 | Kawaguchi |
| 5,277,581 A | 1/1994 | Peterson |
| 5,288,229 A | 2/1994 | Huff et al. |
| 5,292,248 A | 3/1994 | Schultz |
| 5,299,934 A | 4/1994 | Suyama |
| 5,302,117 A | 4/1994 | Kraut et al. |
| 5,302,121 A | 4/1994 | Gagin |
| 5,320,525 A | 6/1994 | Forster |
| 5,320,526 A | 6/1994 | Tuneberg |
| 5,322,435 A | 6/1994 | Pletcher |
| 5,322,613 A | 6/1994 | Ohira |
| 5,356,288 A | 10/1994 | Cohen |
| 5,358,402 A | 10/1994 | Reed et al. |
| 5,362,232 A | 11/1994 | Franseen et al. |
| 5,362,233 A | 11/1994 | Thompson |
| 5,380,196 A | 1/1995 | Kelly et al. |
| 5,383,784 A | 1/1995 | Sernetz |
| 5,395,238 A | 3/1995 | Andreiko et al. |
| D358,649 S | 5/1995 | Moschik |
| D358,650 S | 5/1995 | Moschik |
| D359,776 S | 6/1995 | Hilgers |
| 5,439,379 A | 8/1995 | Hansen |
| 5,441,408 A | 8/1995 | Moschik |
| 5,441,409 A | 8/1995 | Tuneberg |
| 5,443,384 A | 8/1995 | Franseen et al. |
| 5,454,716 A | 10/1995 | Banerjee et al. |
| 5,464,349 A | 11/1995 | Andreiko et al. |

(56) References Cited

U.S. PATENT DOCUMENTS

| | | |
|---|---|---|
| 5,470,228 A | 11/1995 | Franseen et al. |
| 5,474,444 A | 12/1995 | Wildman |
| 5,474,445 A | 12/1995 | Voudouris |
| 5,505,616 A | 4/1996 | Harwell |
| 5,522,725 A | 6/1996 | Jordan et al. |
| 5,545,037 A | 8/1996 | Takeshi |
| 5,556,277 A | 9/1996 | Yawata et al. |
| 5,562,445 A | 10/1996 | DeVincenzo et al. |
| 5,588,833 A | 12/1996 | Risse |
| 5,595,484 A | 1/1997 | Orikasa et al. |
| 5,597,302 A | 1/1997 | Pospisil et al. |
| 5,607,301 A | 3/1997 | Roman |
| 5,616,026 A | 4/1997 | Cash |
| 5,618,175 A | 4/1997 | Reher et al. |
| 5,620,321 A | 4/1997 | Thornburg et al. |
| 5,622,494 A | 4/1997 | Andreiko et al. |
| 5,653,588 A | 8/1997 | Moschik |
| 5,685,711 A | 11/1997 | Hanson |
| 5,692,898 A | 12/1997 | Orikasa et al. |
| 5,707,231 A | 1/1998 | Watt et al. |
| 5,720,611 A | 2/1998 | Teng |
| 5,727,941 A | 3/1998 | Kesling |
| 5,729,768 A | 3/1998 | Fields et al. |
| 5,738,514 A | 4/1998 | DeVincenzo et al. |
| 5,746,592 A | 5/1998 | Nezu et al. |
| 5,746,594 A | 5/1998 | Jordan et al. |
| RE35,863 E | 7/1998 | Sachdeva et al. |
| 5,779,470 A | 7/1998 | Kussick |
| 5,791,897 A | 8/1998 | Wildman |
| 5,810,583 A | 9/1998 | Doyle |
| 5,820,371 A | 10/1998 | Forster |
| 5,829,972 A | 11/1998 | Farzin-Nia |
| 5,829,975 A | 11/1998 | Gold |
| 5,857,849 A | 1/1999 | Kurz |
| 5,871,350 A | 2/1999 | Clark et al. |
| 5,879,157 A | 3/1999 | Schue |
| 5,885,073 A | 3/1999 | Kussick |
| 5,885,074 A | 3/1999 | Hanson |
| 5,890,891 A | 4/1999 | Doyle |
| 5,908,293 A | 6/1999 | Voudouris |
| 5,915,550 A | 6/1999 | Gartz |
| 6,036,489 A | 3/2000 | Brosius |
| 6,053,458 A | 4/2000 | Meyer |
| 6,053,729 A | 4/2000 | Brehm et al. |
| 6,053,759 A | 4/2000 | Kunert |
| 6,071,119 A | 6/2000 | Christoff et al. |
| 6,086,364 A | 7/2000 | Brunson |
| 6,109,916 A | 8/2000 | Wilcko et al. |
| 6,123,544 A | 9/2000 | Cleary |
| 6,126,441 A | 10/2000 | Tenti |
| 6,142,775 A | 11/2000 | Hansen et al. |
| 6,162,051 A | 12/2000 | Brehm et al. |
| 6,190,165 B1 | 2/2001 | Andreiko et al. |
| 6,193,508 B1 | 2/2001 | Georgakis |
| 6,206,690 B1 | 3/2001 | Vargas |
| 6,217,322 B1 | 4/2001 | Kesling |
| 6,220,857 B1 | 4/2001 | Abels |
| 6,227,849 B1 | 5/2001 | Brehm et al. |
| 6,234,792 B1 | 5/2001 | DeVincenzo |
| 6,264,469 B1 | 7/2001 | Moschik |
| 6,276,930 B1 | 8/2001 | Pozzi |
| 6,280,185 B1 | 8/2001 | Palmer et al. |
| 6,302,688 B1 | 10/2001 | Jordan et al. |
| 6,347,939 B2 | 2/2002 | Abels |
| 6,354,834 B2 | 3/2002 | Kanomi |
| 6,358,043 B1 | 3/2002 | Mottate et al. |
| 6,358,046 B1 | 3/2002 | Brehm et al. |
| 6,361,314 B1 | 3/2002 | Garton, Jr. |
| 6,361,317 B1 | 3/2002 | Rahman |
| 6,368,105 B1 | 4/2002 | Voudouris et al. |
| 6,371,760 B1 | 4/2002 | Zavilenski et al. |
| 6,394,798 B1 | 5/2002 | Huff et al. |
| 6,428,314 B1 | 8/2002 | Jones, Jr. et al. |
| 6,461,157 B1 | 10/2002 | Kussick |
| 6,478,579 B1 | 11/2002 | Brusse |
| 6,491,519 B1 | 12/2002 | Clark et al. |
| 6,506,049 B2 | 1/2003 | Hanson |
| 6,582,226 B2 | 6/2003 | Jordan et al. |
| 6,592,366 B2 | 7/2003 | Triaca et al. |
| 6,607,383 B2 | 8/2003 | Abels et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,656,767 B1 | 12/2003 | King et al. |
| 6,659,766 B2 | 12/2003 | Abels et al. |
| 6,659,767 B2 | 12/2003 | Abels et al. |
| 6,663,385 B2 | 12/2003 | Tepper |
| 6,668,834 B1 | 12/2003 | Zikria |
| 6,695,612 B2 | 2/2004 | Abels et al. |
| 6,705,862 B2 | 3/2004 | Schultz |
| 6,709,268 B2 | 3/2004 | Pospisil et al. |
| 6,733,286 B2 | 5/2004 | Abels et al. |
| 6,769,910 B1 | 8/2004 | Pantino |
| 6,776,613 B2 | 8/2004 | Orikasa |
| 6,776,614 B2 | 8/2004 | Wiechmann et al. |
| 6,846,178 B2 | 1/2005 | Freeman, Jr. et al. |
| 6,863,528 B2 | 3/2005 | Lin |
| 6,877,982 B2 | 4/2005 | Williams |
| 6,893,257 B2 | 5/2005 | Kelly |
| 6,903,262 B2 | 6/2005 | Blersch |
| 6,910,884 B2 | 6/2005 | Kelly et al. |
| 6,913,459 B2 | 7/2005 | Fukutomi |
| 7,001,179 B2 | 2/2006 | Devincenzo |
| 7,025,591 B1 | 4/2006 | Kesling |
| 7,033,170 B2 | 4/2006 | Cordato |
| 7,033,171 B2 | 4/2006 | Wilkerson |
| 7,055,908 B1 | 6/2006 | Williams |
| 7,074,037 B2 | 7/2006 | Macchi |
| 7,094,052 B2 | 8/2006 | Abels et al. |
| 7,140,875 B2 | 11/2006 | Lai et al. |
| 7,151,541 B2 | 12/2006 | Seder |
| 7,153,130 B2 | 12/2006 | Christoff |
| 7,210,927 B2 | 5/2007 | Abels et al. |
| 7,234,935 B2 | 6/2007 | Abels et al. |
| 7,247,018 B2 | 7/2007 | Freeman et al. |
| 7,258,545 B2 | 8/2007 | Hotta |
| 7,267,545 B2 | 9/2007 | Oda |
| 7,306,458 B1 | 12/2007 | Lu |
| 7,416,408 B2 | 8/2008 | Farzin-Nia et al. |
| 7,621,743 B2 | 11/2009 | Bathen et al. |
| 7,695,277 B1 | 4/2010 | Stevens |
| 7,704,072 B2 | 4/2010 | Damon |
| 7,780,443 B2 | 8/2010 | Hagelganz et al. |
| 7,811,087 B2 | 10/2010 | Wiechmann et al. |
| 7,850,451 B2 | 12/2010 | Wiechmann et al. |
| 7,909,603 B2 | 3/2011 | Oda |
| 7,959,437 B2 | 6/2011 | Zakhem |
| 7,963,768 B2 | 6/2011 | Hilliard |
| 8,251,697 B2 | 8/2012 | Smith et al. |
| 8,376,739 B2 | 2/2013 | Dupray et al. |
| 8,485,816 B2 | 7/2013 | Macchi |
| 8,573,971 B2 | 11/2013 | Stevens |
| 8,585,399 B2 | 11/2013 | Smith et al. |
| 8,678,818 B2 | 3/2014 | Dupray et al. |
| 2001/0036615 A1 | 11/2001 | Binder |
| 2002/0025502 A1 | 2/2002 | Williams |
| 2002/0110778 A1 | 8/2002 | Abels et al. |
| 2002/0187452 A1 | 12/2002 | Abels et al. |
| 2003/0049582 A1 | 3/2003 | Abels et al. |
| 2003/0064344 A1 | 4/2003 | Vazquez |
| 2003/0088261 A1 | 5/2003 | Schraga |
| 2003/0096209 A1 | 5/2003 | Sugiyama et al. |
| 2003/0143509 A1 | 7/2003 | Kopelman et al. |
| 2004/0244149 A1 | 12/2004 | Anscher |
| 2004/0259048 A1 | 12/2004 | Balabanovsky |
| 2005/0069833 A1 | 3/2005 | Chikami |
| 2005/0244777 A1 | 11/2005 | Schultz |
| 2006/0014116 A1 | 1/2006 | Maijer et al. |
| 2006/0046224 A1 | 3/2006 | Sondhi et al. |
| 2006/0063123 A1 | 3/2006 | Cleary et al. |
| 2006/0099544 A1 | 5/2006 | Lai et al. |
| 2006/0099545 A1 | 5/2006 | Lai et al. |
| 2006/0199137 A1 | 9/2006 | Abels et al. |
| 2006/0228662 A1 | 10/2006 | Lokar et al. |

(56) References Cited

U.S. PATENT DOCUMENTS

| | | |
|---|---|---|
| 2006/0228664 A1 | 10/2006 | Castner et al. |
| 2006/0246392 A1 | 11/2006 | Vigolo |
| 2006/0252002 A1 | 11/2006 | Hanson |
| 2006/0257810 A1 | 11/2006 | Maijer et al. |
| 2006/0263737 A1 | 11/2006 | Oda |
| 2006/0269889 A1 | 11/2006 | Voudouris |
| 2007/0054231 A1 | 3/2007 | Manemann et al. |
| 2007/0092849 A1 | 4/2007 | Cosse |
| 2007/0166658 A1 | 7/2007 | Voudouris |
| 2007/0207436 A1 | 9/2007 | Tan et al. |
| 2007/0224569 A1 | 9/2007 | Oda |
| 2007/0243497 A1 | 10/2007 | Voudouris |
| 2007/0248926 A1 | 10/2007 | Lai et al. |
| 2007/0256694 A1 | 11/2007 | Kussick |
| 2007/0264606 A1 | 11/2007 | Muha |
| 2007/0281269 A1 | 12/2007 | Forster |
| 2008/0014544 A1 | 1/2008 | Nucera |
| 2008/0128297 A1 | 6/2008 | Rose |
| 2008/0131831 A1 | 6/2008 | Abels et al. |
| 2008/0138759 A1 | 6/2008 | Kravitz et al. |
| 2008/0160474 A1 | 7/2008 | Wolf et al. |
| 2008/0182219 A1 | 7/2008 | Spalty |
| 2008/0223377 A1 | 9/2008 | Kussick |
| 2008/0227047 A1 | 9/2008 | Lowe et al. |
| 2008/0268398 A1 | 10/2008 | Cantarella |
| 2009/0004617 A1 | 1/2009 | Oda et al. |
| 2009/0004618 A1 | 1/2009 | Oda et al. |
| 2009/0004619 A1 | 1/2009 | Oda et al. |
| 2009/0042160 A1 | 2/2009 | Ofir |
| 2009/0162807 A1 | 6/2009 | Hagelganz et al. |
| 2009/0291404 A1 | 11/2009 | Oda |
| 2009/0325118 A1 | 12/2009 | Lewis et al. |
| 2010/0003632 A1 | 1/2010 | Ruiz Diaz et al. |
| 2010/0062387 A1 | 3/2010 | Hilliard |
| 2010/0129765 A1 | 5/2010 | Mohr et al. |
| 2010/0159411 A1 | 6/2010 | Oda |
| 2010/0178629 A1 | 7/2010 | Oda et al. |
| 2010/0196840 A1 | 8/2010 | Lai et al. |
| 2010/0203463 A1 | 8/2010 | Huff |
| 2010/0261131 A1 | 10/2010 | Ruiz-Vela et al. |
| 2010/0279247 A1 | 11/2010 | Kesling |
| 2010/0285420 A1 | 11/2010 | Oda |
| 2010/0285421 A1 | 11/2010 | Heiser |
| 2010/0304321 A1 | 12/2010 | Patel |
| 2011/0014583 A1 | 1/2011 | Romano et al. |
| 2011/0020762 A1 | 1/2011 | Kanomi et al. |
| 2011/0039224 A1 | 2/2011 | Cosse |
| 2011/0076633 A1 | 3/2011 | Bryant |
| 2011/0081622 A1 | 4/2011 | Mashouf |
| 2011/0086322 A1 | 4/2011 | Baron et al. |
| 2011/0123942 A1 | 5/2011 | Rudman et al. |
| 2011/0165532 A1 | 7/2011 | Benvegnu' et al. |
| 2011/0287378 A1 | 11/2011 | Dupray et al. |
| 2012/0070797 A1 | 3/2012 | Edgren |
| 2013/0280668 A1 | 10/2013 | Upchurch, Jr. et al. |
| 2013/0280670 A1 | 10/2013 | Edgren |
| 2013/0302745 A1 | 11/2013 | Aldo |
| 2013/0309624 A1 | 11/2013 | Smith et al. |
| 2013/0309625 A1 | 11/2013 | Macchi et al. |
| 2014/0038121 A1 | 2/2014 | Smith et al. |

FOREIGN PATENT DOCUMENTS

| | | |
|---|---|---|
| EP | 0317098 | 5/1989 |
| EP | 0379668 | 8/1990 |
| EP | 0389223 | 9/1990 |
| EP | 0397533 | 11/1990 |
| EP | 0588961 | 3/1994 |
| EP | 0624354 | 11/1994 |
| EP | 0875211 | 11/1998 |
| EP | 1332727 | 8/2003 |
| EP | 1359859 | 11/2003 |
| ES | 2130174 | 7/1999 |
| FR | 2497657 | 7/1982 |
| FR | 2887135 | 12/2006 |
| JP | S64-25847 | 1/1989 |
| JP | H01-160547 | 6/1989 |
| JP | H02-147112 | 12/1990 |
| JP | H03-21236 | 1/1991 |
| JP | H06-507803 | 9/1994 |
| JP | 2579431 | 2/1997 |
| JP | 11-276504 | 10/1999 |
| JP | 2003-102749 | 4/2003 |
| WO | WO 91/07925 | 6/1991 |
| WO | WO 92/00041 | 1/1992 |
| WO | WO 92/20296 | 11/1992 |
| WO | WO 2004/039276 | 5/2004 |

OTHER PUBLICATIONS

U.S. Appl. No. 11/123,470, filed May 5, 2005, Wilson.
U.S. Appl. No. 13/199,828, filed Sep. 9, 2011, Rudman et al.
U.S. Appl. No. 13/506,513, filed Apr. 23, 2012, Rudman et al.
3M Unitek Corporation Catalog, 1990, pp. 1-1, 1-3, 3-7, Figs. A, B.
"Buccal Tube," Sankin, printed Apr. 1, 2004, 7 pages.
"Direct Bond Tubes," American Orthodontics, New Products Catalog, 2005, p. 76.
"Focus on Brackets," Orthodontic Products, Mar. 2005, pp. 1-2.
Ortho Organizers, Inc. Advertisement, "Journal of Clinical Orthodontics," Sep. 1989, 3 pages.
Victory Series Appliance System, Mastering the Art of Orthodontic Application, 3M Unitek Dental Products Division, 1998, 4 pages.
Epstein, "Bi-Dimensional Orthos Treatment: Benefits and Rationale of Differential Bracket-Slot Sizes," Clinical Impressions, 1998, vol. 7(3), 6 pages.
Ricketts, "Provocations and Perceptions in Cranio-Facial Orthopedics," RMO, Inc., Denver, CO, USA, 1989, cover and pp. 982-1021.
International Search Report for International (PCT) Patent Application No. PCT/US03/34430, mailed May 24, 2004.
International Search Report for International (PCT) Patent Application No. PCT/US11/38229, mailed Sep. 21, 2011 2 pages.
Written Opinion for International (PCT) Patent Application No. PCT/US11/38229, mailed Sep. 21, 2011 4 pages.
International Preliminary Report on Patentability for International (PCT) Patent Application No. PCT/US11/38229, mailed Nov. 21, 2013, 6 pages.
Official Action for U.S. Appl. No. 11/782,569, mailed Mar. 10, 2010.
Official Action for U.S. Appl. No. 11/782,569, mailed Oct. 12, 2010.
Notice of Allowance for U.S. Appl. No. 11/782,569, mailed Jan. 25, 2011.
Official Action for U.S. Appl. No. 13/117,070, mailed Dec. 13, 2011 13 pages.
Official Action for U.S. Appl. No. 13/117,070, mailed Mar. 22, 2012 7 pages.
Official Action for U.S. Appl. No. 13/117,085, mailed Dec. 13, 2011 17 pages.
Official Action for U.S. Appl. No. 13/117,085, mailed Mar. 28, 2012 22 pages.
Notice of Allowance for U.S. Appl. No. 13/117,085, mailed Oct. 18, 2012 13 pages.
Official Action for U.S. Appl. No. 13/766,997 mailed Jul. 9, 2013, 14 pages.
Notice of Allowance for U.S. Appl. No. 13/766,997 mailed Oct. 30, 2013, 16 pages.
Official Action for U.S. Appl. No. 13/654,021 mailed Aug. 13, 2013, 17 pages.
Final Action for U.S. Appl. No. 13/654,021 mailed Feb. 5, 2014, 16 pages.
Official Action for U.S. Appl. No. 13/654,021 mailed Apr. 29, 2014, 10 pages.

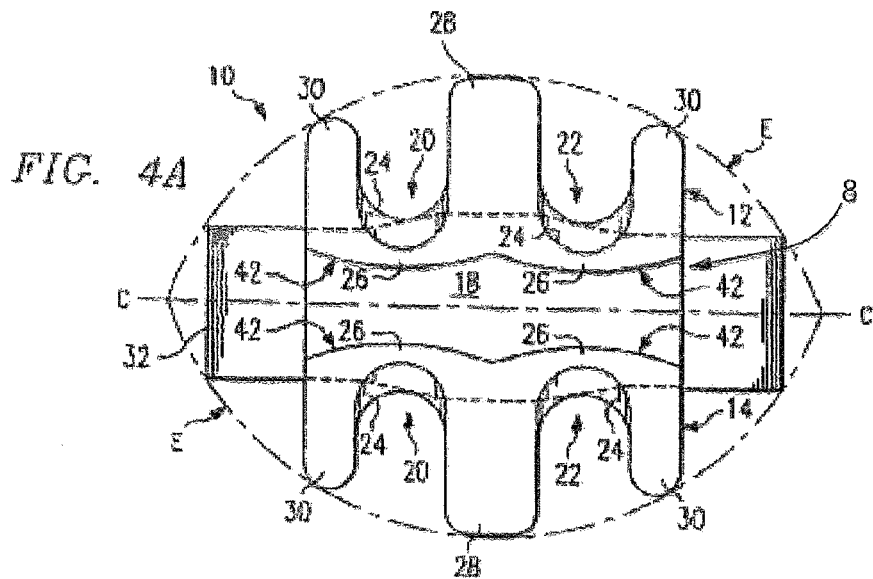
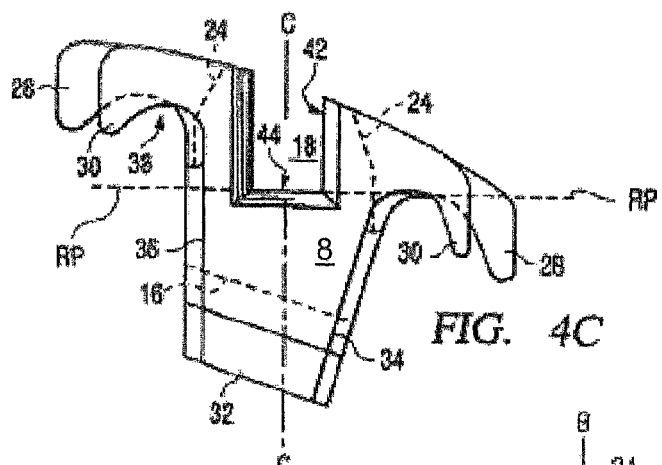
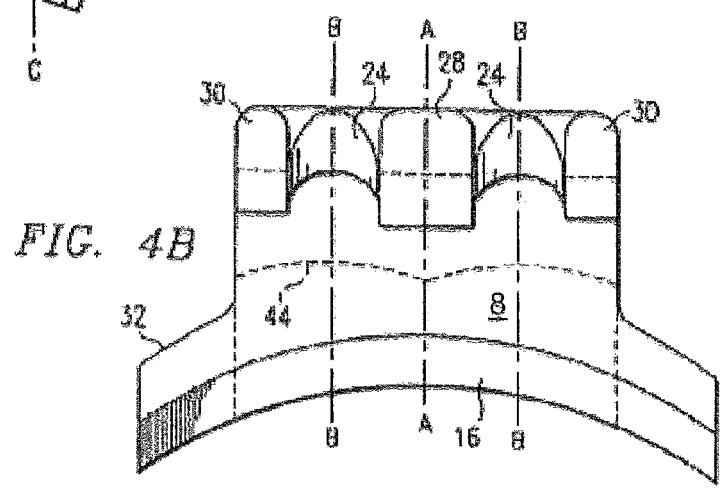

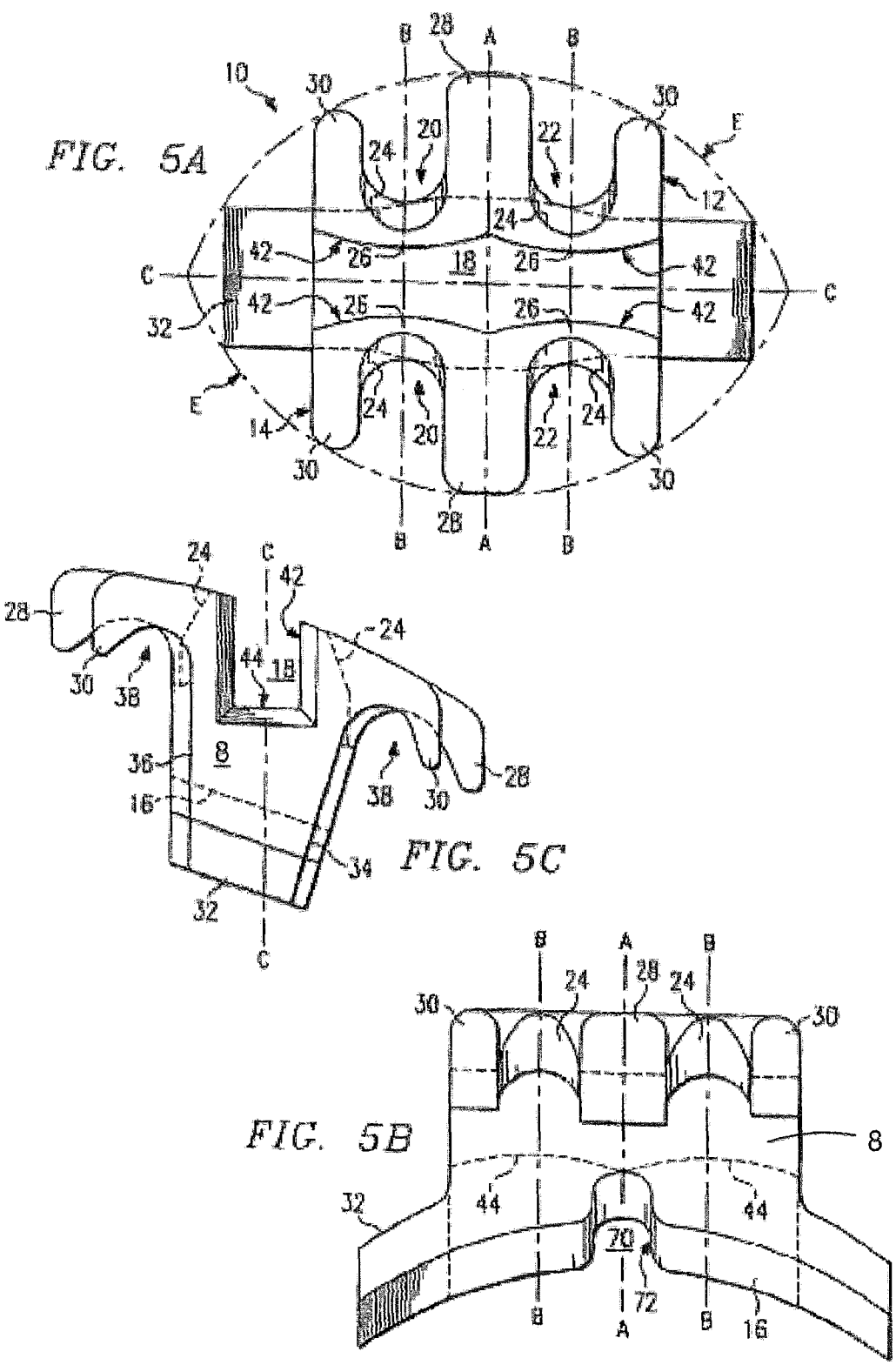

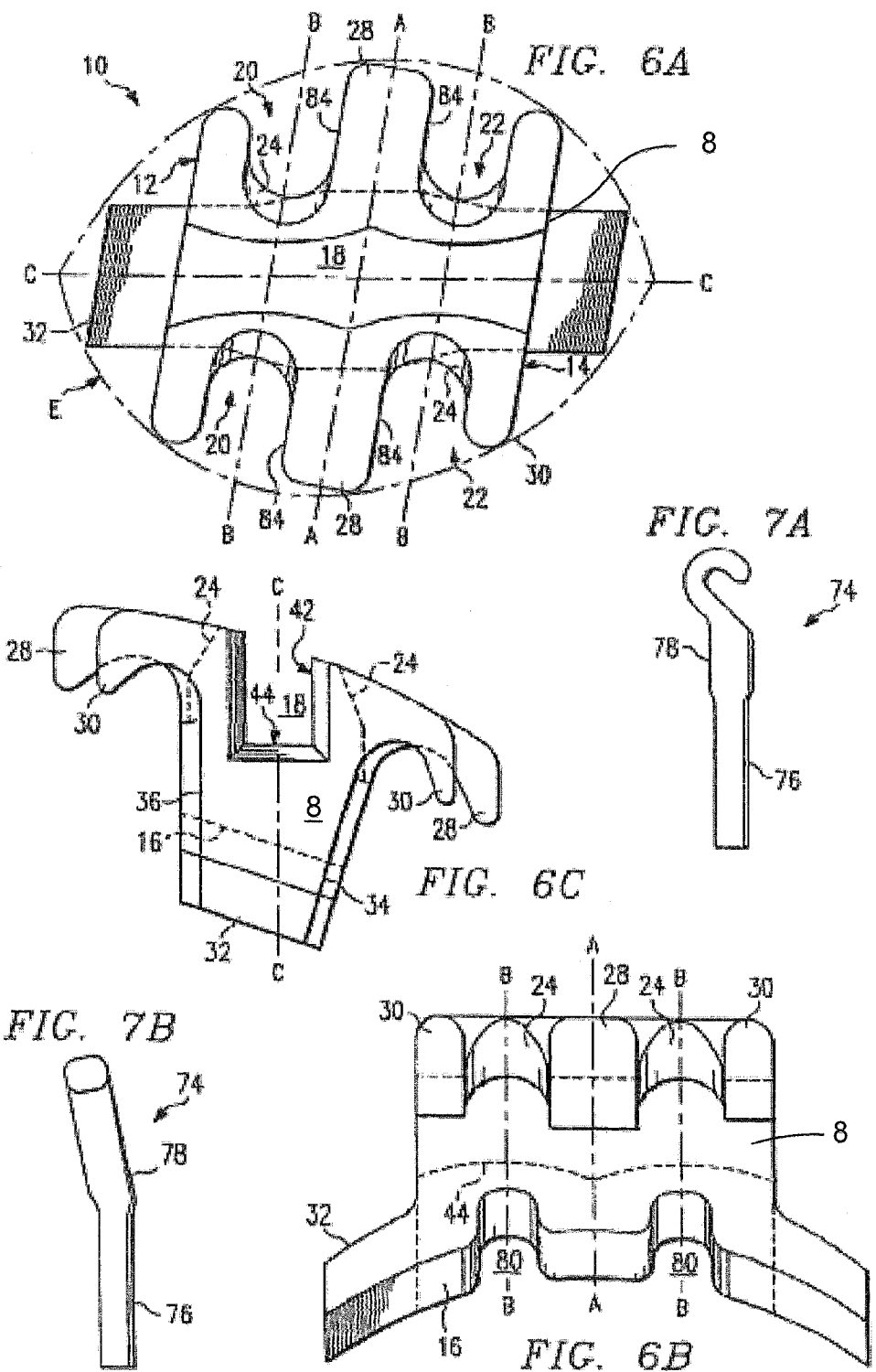

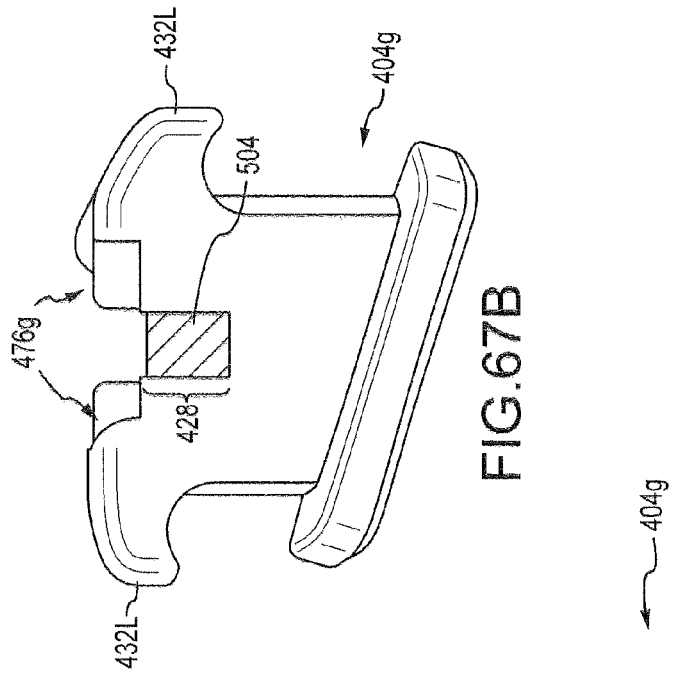
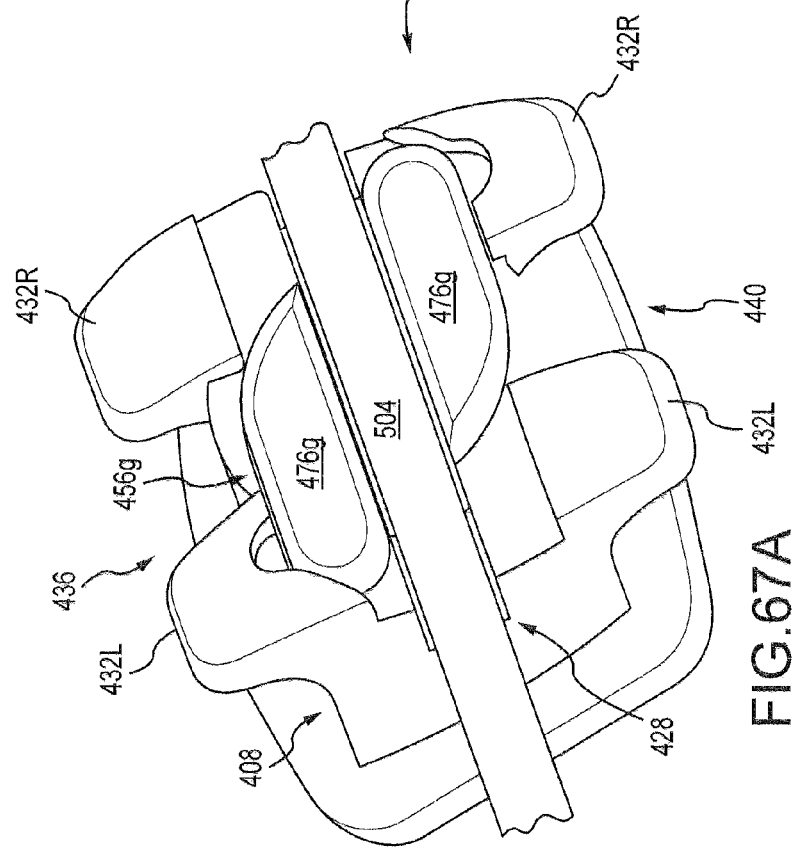

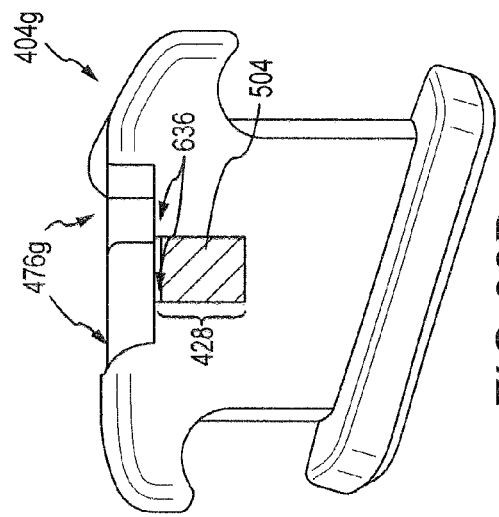
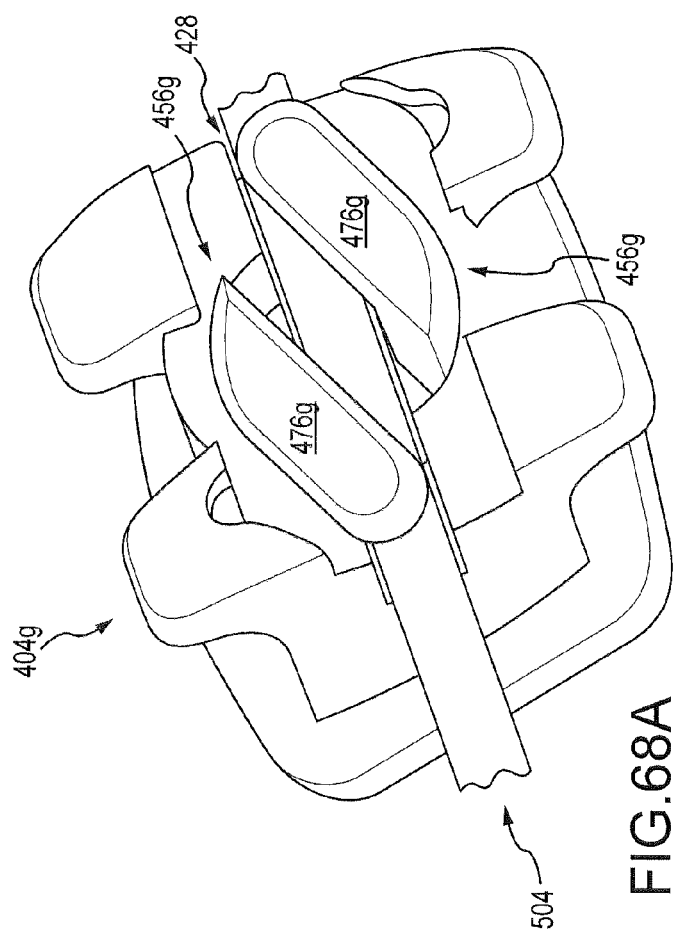

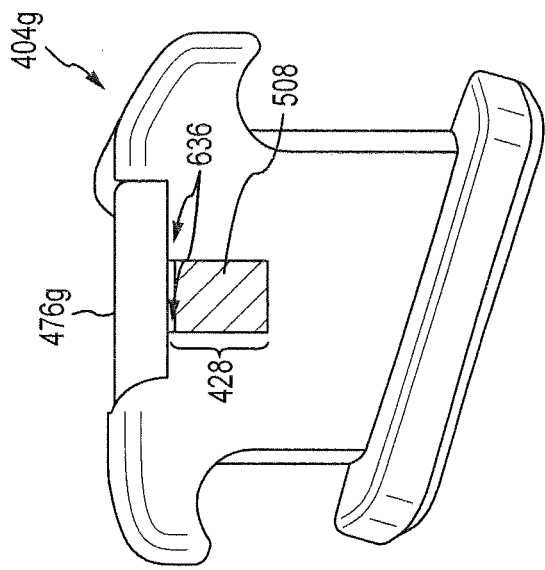
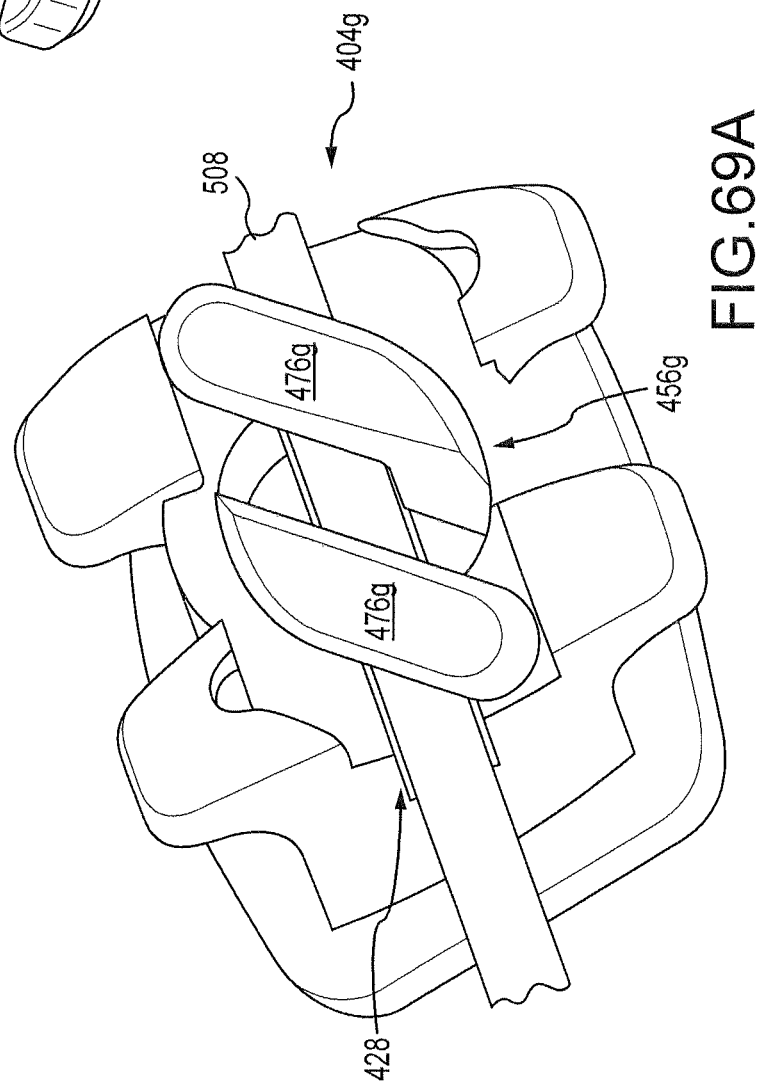

SELF LIGATING ORTHODONTIC BRACKET HAVING A ROTATABLE MEMBER

REFERENCE TO RELATED APPLICATIONS

This application is a continuation of U.S. patent application Ser. No. 13/766,997 (now U.S. Pat. No. 8,678,818), which is a continuation of U.S. patent application Ser. No. 13/117,085, filed May 26, 2011 (now U.S. Pat. No. 8,376, 739), and claims priority to U.S. Provisional Patent Application No. 61/518,927, filed May 12, 2011; the above-identified applications are incorporated fully herein by reference.

FIELD OF THE INVENTION

The present disclosure is directed, at least in part, to a self ligating orthodontic bracket having a rotatable member for securing an archwire within a slot of the bracket.

BACKGROUND OF THE INVENTION

Orthodontic brackets are widely used to align teeth through the application of forces selectively provided by interconnected archwires and accessories. Brackets are typically of metal, ceramic or composite construction and are interconnected to either bands or bonding pads for attachment to teeth.

In edgewise brackets, an archwire passes through a labially opening, horizontal slot defined by one or more pair of opposing tie wings. The archwire is preshaped and sized to provide the desired forces. In each bracket, a tie wing pair includes a gingivally extending tie wing and occlusally extending tie wing. Once placed in the slot of one or more pair of tie wings, an archwire is typically restricted therein by a ligating device such as a steel or elastomeric ligature.

As orthodontic treatment objectives and techniques continue to evolve, numerous corresponding edgewise bracket designs and interconnecting accessories have been proposed. Recently, it has been recognized that it is desirable to reduce frictional engagement between the archwire and bracket surfaces defining the archwire slot to facilitate space closure and bodily tooth movement. Similarly, in many situations, it is now a goal to reduce frictional engagement between the archwire and ligating device employed to restrict the archwire within the slot. Such friction reduction can markedly increase the rate of tooth movement and reduce the duration of the orthodontic treatment.

At the same time, patient comfort and ease-of-use considerations have become increasingly important. Patient comfort has been largely addressed by reducing bracket size to yield smaller and more smoothly contoured brackets. Ease-of-use considerations have stimulated bracket designs which facilitate practitioner's bracket placement/use and accommodate plural modalities.

Texturing of the lingual surface of orthodontic brackets has been used to provide improved bonding between the bracket and the tooth to which the bracket is applied. For example, U.S. Pat. No. 5,522,725, incorporated herein by reference, concerns a method of improving the bond strength of a plastic bracket by temporarily heating and then permanently deforming projections located on the base of the bracket. The deformed projections interlock with adhesive when the bracket is bonded to a tooth. U.S. Pat. No. 5,595,484, incorporated herein by reference, discloses a plastic bracket having a metal reinforcement member partly embedded in the bracket body. FIG. 13 of the '484 patent discloses a bracket base having eight recessed discontinuous portions 36 that include molded identification characters 35. U.S. Pat. No. 5,622,494 (the '494 patent), incorporated herein by reference, discloses several structures, including a spiral-like ridge, concentric rectangles, and a weave pattern. Upon being deformed, each structure creates an undercut structure for forming a mechanical bond with an adhesive. However, the '494 patent and the other patents noted above fail to disclose a base structure that includes lettering, symbols, or numerals that are substantially continuous and that functionally serve as texturing to enhance the adhesive bonding surface of, e.g., an orthodontic appliance to a patient's tooth. The present disclosure, amongst other things as described below, addresses these shortcomings.

SUMMARY

Embodiments of the orthodontic bracket disclosed herein include a bracket body containing the archwire slot as well as tie wings for attaching various orthodontic devices (e.g., elastomeric bands) to the bracket. The rotatable member is rotatable in a first direction (e.g., counter clockwise) relative to a body of the bracket for securing or locking the archwire within the slot, and for rotating in an opposite direction (e.g., a clockwise direction) relative to the bracket body for unsecuring or unlocking the archwire so that it is substantially unrestrained from exiting the slot.

The rotatable member may include a cylindrical or circular portion for inserting into and rotating within a cylindrical bore or recess within the bracket body, wherein the cylindrical recess may be positioned so that it spans the width of the bracket slot. The rotatable member may further include one or more slot coverable extensions of various shapes and functionality wherein such extensions can be rotated into the slot opening where an archwire can be inserted into the opening and/or removed from the bracket slot via this opening. In particular, such extensions, when rotated to occlude at least a portion of the slot opening thereby preventing an archwire residing in the bracket slot from exiting therefrom, and when rotated out of the slot opening, these extensions do not prevent the archwire from being readily removed from the bracket slot, e.g., by an orthodontist or technician. In one or more embodiments, such coverable extensions may be C-shaped. However, other shapes are also within the scope of the present disclosure. In particular, such slot coverable extensions may be straight or bar shaped, such extensions may be parallel to one another, or such extensions may be generally irregularly shaped. Additionally, such extensions may include one or more notches that can be assessed by an orthodontic tool for rotating the rotatable member.

In one or more embodiments, the rotatable member may include two opposing columns attached to opposing sides of the circumference of the cylindrical portion, wherein such columns extend away from their attachment to the cylindrical portion such that they extend out of the cylindrical recess for attaching to the one or more rotatable extensions described above. The attachment of the columns to opposing sides of the cylindrical portion allow for the insertion of an archwire between the columns so that the archwire can reside in the archwire slot. More specifically, although the columns extend above the side walls of the slot, the columns do not interfere, regardless of the rotation of the rotatable member (relative to the bracket body), with an archwire's placement in or removal from the archwire slot. In particular, the columns may rotate (when the rotatable member rotates) about a central axis of the cylindrical recess, and rotate within a confined angular range that prevents them from conflicting or interfering with the operation of an archwire within the slot.

In one or more embodiments, the rotatable member and the cylindrical recess may include various features for being rotatably securing the rotatable member within the cylindrical recess so that this member is substantially prevented for disengaging from the bracket body. Such features may include mating combinations of projections and recesses such that a projection (or recess) may be provided on the cylindrical portion and/or the columns for mating with a corresponding recess (or projection) of an interior wall of the cylindrical recess for locking the rotatable member therein while also allowing it to rotate therein. Note that such mating projections and recesses may be, respectively, ridges and grooves.

Also, note that the cylindrical recess may include additional features or mechanisms that prevent the rotatable member from freely rotating within the cylindrical recess. In one or more embodiments, a circular cross section (perpendicular to the central axis of the cylindrical recess) may be slightly out of round in various places to frictionally engage adjacent surfaces of the rotatable member for assisting in maintaining the slot coverable extensions in one or more predetermined orientations relative to the slot. In one or more embodiments of the bracket, the cylindrical recess and the rotatable member may include interlocking elements that substantially restrict the rotation of the rotatable member to discrete and predetermined angular orientations about the central axis. Such interlocking elements may provide a ratchet mechanism, or alternatively interlocking shapes wherein a first shaped element (e.g., on the cylindrical portion of the rotatable member or a wall portion of the cylindrical recess) mates or interlocks with compatibly one or more shaped elements (on the other of the rotatable member or a wall of the cylindrical recess) dispersed at discrete angular positions about the central axis for restricting rotation of the rotatable member from one of these positions to another. Note that such interlocking elements may allow the rotatable member to rotate in both a clockwise and a counter clockwise direction when a sufficient predetermined directional force(s) is applied for disengaging the interlocking elements from a first position and interlocking at a second position.

In one or more embodiments of the bracket, the strength transmitted to the free ends of the slot coverable extensions for covering the slot is partially derived from the circular shape of the attached cylindrical portion and the intimate fitting of this cylindrical portion of the rotatable member within the cylindrical recess. In particular, such strength may allow the extensions to be thinner than one of ordinary skill in the art would expect, thus providing additional patient comfort.

In one or more embodiments of the slot coverable extensions, the side thereof facing the bracket body may include features or elements for engaging with the bracket body adjacent the slot for assisting in holding such extensions in a "closed" position (i.e., where the extensions span or at least partially cover a width of the slot opening thereby preventing, e.g., an archwire from exiting the slot), or in an "open" position (i.e., where the extensions do not span or interfere with the slot opening in a manner that would prevent an archwire from entering or exiting the slot). In particular, such an underside may include one or more protrusions for mating with a corresponding depression in the bracket body adjacent the slot.

In one or more embodiments, the bracket's cylindrical recess remains open (e.g., not completely enclosed) to facilitate self cleaning, and to reduce calculus build up and stuck moving parts. In another embodiment, the bracket's cylindrical recess is completely enclosed. Tooth brush bristles can access the walls of bracket body.

In one or more embodiments of the bracket, the slot coverable extensions can be configured so that in at least one rotatable position such extensions cause or induce an archwire in the slot to be "actively" held in place within the slot, wherein, for example, the extensions (or another bracket component) contacts the archwire for causing or forcing the archwire into contact with the surfaces of the slot (e.g., a floor of the slot) with sufficient force to induce frictional forces therebetween such that (for orthodontic purposes) such frictional forces effectively inhibit movement of the archwire in a direction along the length of the slot. Additionally/alternatively, the slot coverable extensions can be configured so that in at least one rotatable position such extensions cause or induce an archwire in the slot to be "passively" held in place within the slot, wherein, for example, the extensions (or another bracket component) only loosely restrains the archwire to remain in the slot in a manner such that the archwire can readily move in a direction along the length of the slot. In particular, in the passive archwire restraining configuration, there is insufficient frictional forces between the archwire and the slot (for orthodontic purposes) to effectively inhibit movement of the archwire in a direction along the length of the slot. Moreover, in one or more embodiments of the bracket, the slot coverable extensions can be rotated from a passive configuration to an active configuration, and/or from an active configuration to a passive configuration.

The orthodontic bracket disclosed herein may be comprised of metal, plastic or ceramic or combinations thereof. Equivalent materials also may be used. Metal injection molding (MIM) technology can be used for manufacturing components of the bracket, including the bracket body which provides features for rotatably securing the rotatable member to this body. In particular, the bracket body may be manufactured using a breakaway design in MIM for one piece bracket body assembly.

In a related aspect of the present disclosure, an orthodontic appliance, e.g., a bracket or tube, is described, wherein the appliance has information formed (equivalently, embedded) in the underneath side of the base of the appliance. In particular the information may be one or more symbols formed in the underneath side of the base in a manner wherein such embedded symbols are also structurally important to the adhesion of the appliance to a patient's tooth. That is, the symbols significantly increase the total surface area of the appliance base to which an adhesive can bond.

In one embodiment of the present disclosure provides a substantially continuous series of alpha-numeric characters (such as letters or numerals) or symbols (such as company logos) that are formed or embedded in the base in a manner such that the symbols or characters of the base of the bracket serve to increase the base total surface area (which includes the area of the walls separating the projected portions of the base from the recessed portions of the base) to which an adhesive can effectively adhere for effectively facilitating bonding of the orthodontic appliance with a patient's tooth when the base of the appliance is attached to the tooth. Hereafter, the term "characters" refers to either letters, and/or numbers, and/or graphics, and/or symbols (such as logos), and/or various portions of an informational encoding, and/or a combination thereof. "Substantially continuous" is meant to convey the regular matrix-like aspect of the characters configured on the appliance base so as to facilitate a more or less textured surface for bonding purposes.

In another embodiment disclosed herein, an orthodontic appliance may have an embedded base that does not include a substantially continuous series of characters, but instead may include a non-repeating encoding of information, e.g., about the appliance.

One of the heretofore unappreciated aspects provided by the present disclosure includes the ability of a manufacturer and/or supplier of orthodontic devices to have a trademark or other identifying character (i.e., a name, symbol, part number, etc.) emblazoned on the actual device. This contributes to customer confidence in purchases of "real" (vs. knock-off) products and further permits effective recalls of product in the event of later discovered difficulties.

In a separate aspect of the disclosure, a perimeter rail, and more preferably, a discontinuous perimeter rail may be used at the perimeter edges of the base. The discontinuous perimeter rail, if used, is in contact with the tooth surface, with the interior portion of the information content in the base having its characters recessed relative to the surface of the discontinuous perimeter rail. If used, the perimeter rail forms a pocket to the base interior surrounded by the perimeter rail wherein this base interior receives the adhesive for attaching the orthodontic appliance to the tooth surface. Thus, if used, a perimeter rail contacts the tooth surface, with the base embedded information content recessed relative to the surface of the perimeter rail.

Since the characters are preferably recessed, the space between and around the characters is preferably non-recessed or projected. Thus, the projected space between the characters is either in contact with the tooth, or is the next surface closest to the tooth's surface if a perimeter rail is present, as discussed below. The surface of the recessed characters is preferably further away from the tooth surface than the space between the characters. Alternatively, the opposite arrangement may be used, where the space between and around the characters is recessed, and the characters themselves are projected. In either case, the walls between the projected and recessed portions of the appliance base may increase the total surface area for adhesive contact in the range of 120% to 125% of what a two dimensional appliance base might provide, and in at least some embodiments 140% or more, wherein the two dimensional appliance base has the same exterior dimensions and general convexity as the appliance base, but without the undulating or abrupt changes in the base surface curvature that do not follow the smoothly changing contour of a patient's tooth. More preferably, the total surface area for adhesive contact may be at least 144% of what a two dimensional appliance base provides. For example, the corresponding two dimensional base is effectively a flat or convex surface that generally conforms to a surface of a tooth. Said another way, for orthodontic bases according to the present disclosure, the at least 125% value above corresponds to at least 20% of the total surface area of the base being provided by the walls of the characters that connect the most recessed surface portions of the base from the more projected portions of the base, and the at least 144% value above corresponds to at least 29% of the total surface area of the base being provided by the walls of the characters that connect the most recessed surface portions of the base from the more projected portions of the base. Note that such an increase in base total surface area is believed to substantially distinguish the embedded information of the present orthodontic appliances from those of the prior art.

The disclosure herein shows an orthodontic appliance having a pair of tie wings defining an archwire slot therebetween, and a pair of ligating support means, one defined within the mesial/distal extent of each tie wing. The ligating support means may be selectively employed to reduce frictional engagement between an archwire positioned in the slot and a ligating device positioned on the ligating support means and across the archwire slot. Each ligating support means includes a sloped, or angled, portion that extends labially toward the slot (e.g., labially from the gingival/occlusal periphery towards the slot), to reduce binding of a ligating device positioned thereupon. The ligating support means are preferably notches extending from the gingival or occlusal periphery of a tie wing, sized to readily receive a ligating device, and preferably having a curvilinear, concave configuration to further reduce binding. Typically, the opposing notches in a given pair of tie wings have a common center axis which is parallel to the gingival-occlusal center axis of the orthodontic appliance. When the archwire slot includes convex sidewall and/or floor portions to reduce frictional engagement between the archwire and the appliance, the ligating support means are preferably disposed adjacent thereto (e.g., centered upon a common gingival-occlusal plane) for enhanced treatment control.

In another aspect of the present disclosure, an edgewise bracket is disclosed having a single pair of tie wings and two pairs of opposing ligating support means defined within the mesial/distal extent of the tie wings, one pair on each of the mesial and distal sides of the bracket. The gingival/occlusal extremes of the tie wings define an elliptical configuration when viewed from the labial ("viewed labially"). More particularly, each tie wing comprises central, mesial and distal portions which extend gingivally or occlusally, with ligating support means defined between the central and mesial portions and between the central and distal portions, wherein the gingival/occlusal edges of such portions define an elliptical configuration. Such configuration accommodates size reduction, yielding patient comfort benefits, while preserving structural integrity and performance.

In this regard, and as will become apparent, a single pair of opposing T-shaped tie wings is preferred. That is, the "caps" of the T-shaped tie wings define an archwire slot therebetween, and the "center legs" of each tie wing extends gingivally or occlusally. The ligating support means are preferably notches defined on the gingival/occlusal periphery on both the mesial and distal sides of a center leg of each T-shaped tie wing. The center legs each comprise a gingivally/occlusally extending cantilevered portion that can be conveniently employed as a stanchion for ligature interconnection. The mesial/distal tie wing tip portions on the outside of each notch also comprise gingivally/occlusally extending cantilevered portions that extend a sufficient distance outward from the outer tie wing sidewalls to retain a ligating device in an arcuate seat formed under the cantilevered tie wing tip portions and center legs during conventional ligation. Relatedly, the cantilevered center leg of each T-shaped tie wing should extend at least approximately the same distance outward beyond the outer gingival/occlusal extremes of the adjacent ligating support means so as to retain a ligating device when the ligating support notches are selectively employed by a practitioner to support a ligating device.

In a further aspect of the present disclosure, an edgewise bracket is provided having a single pair of tie wings defining an archwire slot therebetween, and an integral T-shaped hook extending gingivally/occlusally (typically only gingivally) from one tie wing, and in perpendicular relation to the longitudinal center axis of the archwire slot, wherein traction devices (e.g., rubber bands, springs, etc.) can be readily attached from a plurality of directions so as to accommodate plural modalities for treatment. The T-shaped hook is centered upon the gingival-occlusal center axis of the bracket, and is preferably provided as a cantilevered extension of the center leg of a T-shaped tie wing so as to communicate external force moments created by inter-connected traction devices close to a tooth's root center of resistance. Preferably, the T-shaped hook is generally flat as viewed from the mesial and distal aspects. Further, as viewed from the labial aspect, the T-shaped hook preferably comprises a tapered portion contiguous to the center leg of the T-shaped tie wing, an arcuate neck portion contiguous thereto, and a head portion contiguous thereto the tapered portion, wherein a traction device may be reliably maintained in the neck portion. That is, the tapered portion serves to restrict movement of the traction device towards the archwire slot of the bracket, and the head portion serves to restrict disconnection of the traction device from the T-shaped hook. The integral T-shaped hook preferably comprises a malleable material so as to allow for selective pivotal movement of the T-shaped hook by the orthodontic practitioner as may be desirable for soft tissue clearance and patent comfort.

In yet another aspect of the present disclosure, an edgewise bracket is provided having at least one pair of tie wings defining an archwire slot therebetween, wherein when viewed from mesial/distal aspects, the gingivally/occlusally facing outer sidewalls of the tie wing pair define a trapezoid (although rounded and/or curved sidewalls are also contemplated). One outer sidewall is disposed at an angle relative to the longitudinal center plane of the archwire slot, wherein the sidewall extends labially away from such center plane. The other sidewall is disposed substantially parallel to the archwire slot center plane. The angled sidewall is typically disposed gingivally in both maxillary and mandibular applications. By way of example, use of the described configuration and positioning allows for enhanced, early treatment of partially erupted upper bicuspids, wherein the archwire slot will be acceptably, gingivally positioned upon full eruption of the bicuspid. This enhances treatment and reduces demands upon the practitioner time. Further, bracket systems of this design will generally reduce bracket/tooth contact between the upper and lower arches. Bracket profile and strength can also be acceptably maintained using the described configuration. The benefits associated with this trapezoidal configuration may be extended to orthodontic treatment applications requiring positive, negative, or no torque by appropriately configuring/contouring the occlusal/gingival extent of the bracket base or bottom.

In another aspect of the present disclosure, an edgewise bracket is provided having one tie wing pair defining an archwire slot therebetween and at least one auxiliary slot extending from a gingival edge to the occlusal edge, or vice versa, wherein the slot and shaft of the auxiliary device to be inserted into the slot have complimentary configurations to restrict rotational movement therebetween. By way of example, the auxiliary slot may have adjoining flat inner sidewalls (e.g., defining square corners), and the auxiliary shaft may have complimentary flat outer sidewalls (e.g., defining square corners), wherein rotational movement therebetween is desirably restricted.

In a related aspect of the present disclosure, an edgewise bracket is provided having a single tie wing pair defining an archwire slot therebetween, at least one convex portion extending labially and transversely across the floor of the archwire slot, and at least one auxiliary slot extending gingivally/occlusally and positioned under the convex slot floor portion. By positioning the auxiliary slot under the convex slot floor portion, bracket height can be advantageously conserved, and therefore reduced, so as to enhance patient comfort. When two convex slot floor portions are provided, one on each of the mesial/distal sides, twin auxiliary slots may be advantageously positioned so that one passes under each of the convex slot floor portions. In addition to the above-noted advantages, this bracket yields significant tooth rotation capabilities. For example, in early treatment stages, the twin auxiliary slots can be utilized with a steel ligature to achieve rapid gross tooth rotation. As can be appreciated, complementary auxiliary slot/auxiliary shaft configurations of the above-described nature can also be employed.

In one embodiment of the present disclosure, an edgewise bracket is provided having a single set of opposing T-shaped tie wings with ligating support notches defined on each side (i.e., mesially and distally) of the center leg of each tie wing. The sidewalls defining the archwire slot are provided to present two sets of opposing convex sidewall portions, one set on each of the mesial and distal sides of the bracket. Similarly, the floor of the archwire slot is provided to present two convex portions extending labially and transversely across the slot, one on each of the mesial and distal sides of the bracket. By virtue of this arrangement, the bracket yields desirable tooth rotation and alignment capabilities with reduced archwire/archwire slot frictional engagement and selectively reduced archwire/ligating device frictional engagement. Further, this configuration defines a dynamic archwire slot, wherein the archwire is allowed to maintain a "memory" of its slot entry angle, as is now desirable. The notches each comprise a portion that extends labially outwardly from the gingival/occlusal periphery towards the archwire slot and presents concave, curvilinear surfaces to reduce ligature binding. The gingival/occlusal edges of the center legs and wing tip portions of the opposing T-shaped tie wings define an elliptical configuration when viewed labially so as to reduce bracket size and advance patient comfort/appearance. All prominent edges exposed to soft tissue are preferably rounded for patient comfort.

An integral T-shaped hook of the above-described nature may be optionally provided as a cantilevered gingival/occlusal extension of the center leg of either T-shaped tie wing. The T-shaped hook preferably comprises a malleable material and preferably comprises flat lingually and labially facing surfaces, wherein the hook can be manually pivoted to a limited extent by a practitioner relative to the center leg of the tie wing.

An auxiliary slot may also be optionally provided and disposed within the gingival-occlusal center plane of the bracket, underlying the center leg portions of the opposing T-shaped tie wings. Alternatively, twin auxiliary slots may be provided, one on each side of the gingival-occlusal center plane of the bracket (i.e., mesially and distally positioned), such slots passing under the mesial and the distal convex slot floor portions of the archwire slot. Whether a single or twin auxiliary slot arrangement is provided, each slot preferably has an inner-configuration which will restrict rotation of complimentary auxiliaries inserted thereto, as described above.

The T-shaped tie wings of the bracket may also be optionally defined so that the outer gingival/occlusal facing sidewalls of the tie wing pair define a trapezoid when viewed from the mesial or distal aspects. More particularly, one of the outer sidewalls is disposed at an angle relative to the longitudinal center plane of the archwire slot, and may be perpendicular to the tie wing base surface or base/bottom surface of the bracket. The other outer sidewall is disposed in parallel relation to the center plane of the archwire slot.

In combination with the above-described trapezoidal configuration, the base surface of the bracket, namely its gingival/occlusal extent, may be provided for generating "positive torque," "negative torque," and "no torque." "Positive torque" is applied to a tooth having a tooth-long axis which projects the crown outwardly from a plane which is perpendicular to the occlusal plane and which coincides with the respective arch (e.g., mandibular or maxillary) (e.g., when the tooth root is tipped lingually). "Negative torque" is applied to a tooth having a tooth-long axis which projects the crown inwardly from the above-described plane (e.g., when the tooth root is tipped buccally). "No torque" is applied to a tooth having a tooth-long axis which is properly within the above-described plane.

The configuration of the base surface of the bracket, namely its occlusal/gingival extent, may be defined in relation to a reference plane which coincides with that portion of the floor or bottom of the archwire slot which engages the archwire when positioned therein (e.g., a plane which is tangent to the two convex portions on the floor of the slot). As an example of the foregoing trapezoidal configuration and base variations, with the "angled" outer sidewall being gingivally positioned in a maxillary application, the base may be configured to generally extend from its gingival edge to its occlusal edge generally toward the noted reference plane to provide for a "positive torque" on the tooth. Moreover, the base may be configured to generally extend from its gingival edge to its occlusal edge generally away from the noted reference plane to provide for "negative torque" on the tooth. Furthermore, the base may be configured to generally extend from its gingival edge to its occlusal edge generally parallel to the noted reference plane to provide for "no torque" on the tooth. With the "angled" outer sidewall being gingivally positioned in a mandibular application, the above-described non-parallel configurations of the base would provide negative and positive torque, respectively.

The center leg of each T-shaped tie wing may also be optionally disposed at an acute angle relative to the longitudinal center axis of the slot. Such angling may be desired in applications wherein the central axis of the clinical crown is positioned at an acute angle relative to the occlusal plane in normal occlusion. Such angling correspondingly facilitates the practitioner's placement of the bracket on a tooth, wherein the axes of the center legs may be disposed along a tooth long axis, and wherein the center axis of the bracket slot may be disposed parallel to the occlusal plane. Preferably, the mesial/distal facing edges of the center leg of each T-shaped tie wing are also parallel to the axes of the center legs to further facilitate accurate placement on a tooth. It is also preferable for the center axes of opposing ligating support notches to be disposed parallel to the gingival-occlusal center plane of the bracket. Relatedly, for rotational purposes, it is preferable for the apices of the opposing convex slot sidewall portions and a convex slot floor portion correspondingly positioned on the same mesial or distal side to lie within a common plane that is disposed substantially perpendicular to the longitudinal center plane of the archwire slot.

The present disclosure further includes a method for manufacturing and distributing embodiments of the novel orthodontic appliance to orthodontists and other trained personnel for the application of such an orthodontic appliance to a patient's tooth. In particular, such orthodontic appliances may be injection molded with the embedding of encoded information molded into the base of each such appliance. However, other techniques for embedding the encoded information into the base are also within the scope of the present disclosure, including: metal injection mold (MIM) techniques, plastic injection mold (PIM) techniques, ceramic injection mold (CIM) techniques, casting techniques and/or machining techniques as one of skill in the art will understand.

Still other embodiments are included within the scope of the present disclosure. For example, in one embodiment, rotating portions reversibly secure an archwire in the slot and rotate between a freely rotating position and a reversibly anchored position. In one embodiment the anchored position involves a separate vertical or lateral movement of the rotating portion with respect to the remainder of the bracket so as to achieve a locking function. In other embodiments, at least two pivot pins are employed, each positioned one opposite side of the bracket, and in one embodiment, on different sides of the archwire slot. Still other embodiments involve rotation of a pivot pin having a pivot axis that is oriented in a non-perpendicular orientation to the archwire slot and/or in a position that is not substantially normal to the tooth surface.

In still other embodiments, the self-ligating orthodontic bracket includes a bracket body with an archwire slot, at least two, but in other embodiments four or more, spaced apart mounting arms having mounting slots, and a mounting pin permanently or removably mounted in the mounting slots. A closure member may be mounted to the body of the bracket and movable between a reversibly closed position in which at least a portion of the archwire slot is covered and an open position, in which the archwire slot is uncovered. The closure member may have various elements that slide, rotate, pivot, and/or enclose that can be mounted to the body of the bracket.

Yet another embodiment provides a self-ligating orthodontic bracket that includes a mounting base for attachment to a tooth surface, an archwire slot formed upon the base and sized for receiving an orthodontic archwire, a rotary ligating cover selectively rotatable between an open position permitting access to the archwire slot and a closed position covering the archwire slot, and one or more locking features for holding the rotary cover in a closed position. Such locking feature may be positioned and designed to cooperatively mate with other designated portions of the bracket so as to achieve desired reversible engagement and open-retention features may also be provided that facilitate the purposeful opening of the locking feature to permit manipulation of the bracket, archwire, etc. as deemed appropriate by either the orthodontist or the patient.

Other embodiments are directed towards an orthodontic self-ligating bracket provided with a cover that can be rotated over an arch wire slot in the base portion to close when a frangible portion is severed upon initiating rotation of the cover. Such cover rotates about a hinge, which may include a pin or axle that can be moved laterally and/or vertically after the frangible portion is severed and preferably is manufactured to form one piece, such as using an injection molding, machining, or casting process, thus avoiding additional subsequent assembly to attach a cover to a base.

Some embodiments employ a self-ligating orthodontic bracket clip slidably engagable with the bracket to allow the clip to slidably move between an open position and a closed position in which the clip extends across the archwire slot to retain the archwire in the archwire slot.

Other embodiments employ a replaceable closing spring member detachably connected to a base member to maintain pivoting engagement of such spring member when desired and easy removal of the spring members when desired.

Other self ligating bracket designs include a latching member having a hinge pin made of a flexible material so that a portion of the latching member is engagable with the bracket.

In some embodiments, a range of adjustability is provided in the range of motion of a closing or locking member, thus limiting the forces encountered by an archwire held in the archwire slot, thus permitted desired sliding of the archwire in the slot. To accomplish this end, a camming mechanism can be employed. The bracket body may be formed from a non-metallic material, such as a polymer, a filled polymer composite, or a ceramic, and the self-ligating mechanism may be formed from a metal. A resilient engagement member with a detent positioned to engage an aperture can be employed to achieve secure closure.

To further an appreciation of the various designs of the present disclosure and to assist in providing requisite support of written description and enablement of the various features of the present disclosure, the following references are hereby incorporated herein by reference in their entries: 20110081622 to Mashouf; U.S. Pat. No. 7,695,277 to Stevens; 20100203463 to Huff; U.S. Pat. No. 7,780,443 to Hagelganz; 20110076633 to Bryant; 20100285421 to Heiser; 20100159411 to Oda; and 20100062387 to Hilliard.

Various embodiments of the present disclosure are set forth in the attached figures and in the detailed description as provided herein and as embodied by the claims. It should be understood, however, that this Summary section may not contain all of the aspects and embodiments claimed herein. Additionally, the disclosure herein is not meant to be limiting or restrictive in any manner, and is directed to be understood by those of ordinary skill in the art. Moreover, the present disclosure is intended to encompass and include obvious improvements and modifications of embodiments presented herein.

Additional advantages of the present disclosure will become readily apparent from the following discussion, particularly when taken together with the accompanying drawings.

BRIEF DESCRIPTION OF THE DRAWINGS

FIGS. 4A-E illustrate labial, side and end views of a modified version of said first embodiment having outer tie wing sidewalls that define a trapezoid therebetween, the end views illustrating various alternative configurations of the base to provide for positive, negative, and no torque on a tooth.

FIGS. 5A-C illustrate labial, side and end views of the modified version of the first embodiment illustrated in FIGS. 4A-C, with a central auxiliary slot.

FIGS. 6A-C illustrate labial, side and opposing end views of the modified version of the first embodiment illustrated in FIGS. 4A-C, with an angulated gingival-occlusal center axis and twin auxiliary slots.

FIGS. 7A-B illustrate two views of an exemplary auxiliary device useable with the auxiliary slots of, e.g., the embodiment of the orthodontic bracket shown in FIG. 6B.

FIGS. 28 through 41 show various orthodontic appliances with bases 16 having encoded information embedded or formed therein, wherein the characters 94 are on the recessed surface(s) 90 (e.g., as shown in FIGS. 9A and 9B), and the intermediary space 96 between the characters is provided on the projected surface(s) 92 (e.g., as shown in FIGS. 9A and 9B). Note that for a given figure number, whenever there are figures A and B for the figure number, such figures A and B are different views of the same orthodontic appliance; e.g.

FIGS. 67A and 67B show views of a further embodiment of a self-ligating orthodontic bracket 404g with a slot covering rotatable member 456g, wherein this bracket is in the open configuration allowing easy insertion and/or extraction of an archwire 504 from the bracket slot 428. In particular, FIG. 67A shows a top (slightly oblique) view of the orthodontic bracket 404g, and FIG. 67B shows a corresponding side view of the bracket 404g.

FIGS. 68A and 68B show views of the self-ligating orthodontic bracket 404g, wherein this bracket is in the passively closed configuration such that insertion and/or extraction of an archwire 504 from the bracket slot 428 is prevented by rotatable member 456g. However, the archwire 504 is relatively loosely confined to the slot 428. In particular, FIG. 68A shows a top (slightly oblique) view of the orthodontic bracket 404g in the closed passive configuration, and FIG. 68B shows a corresponding side view of the bracket 404g.

FIGS. 69A and 69B show views of the self-ligating orthodontic bracket 404g, wherein this bracket is in the actively closed configuration such that insertion and/or extraction of an archwire 504 from the bracket slot 428 is prevented by rotatable member 456g, and the archwire 504 is relatively firmly secured to the slot 428 to thereby prevent (or substantially inhibit) archwire movement therein. In particular, FIG. 69A shows a top (slightly oblique) view of the orthodontic bracket 404g in the closed active configuration, and FIG. 69B shows a corresponding side view of the bracket 404g.

The drawings provided herewith are not necessarily to scale. However, the drawings are believed to be proportionately accurate.

DETAILED DESCRIPTION

In the various embodiments of orthodontic brackets, and components thereof described hereinbelow, different embodiments of features or elements having a same general functionality will typically be identified by a label having a same numerical portion of the label, but a different letter as a suffix. Thus, for example, various embodiments of a self ligating orthodontic bracket are disclosed hereinbelow, and identified by the numerical label "404", but at least some of these different embodiments are distinguished from one another by different letters such that different bracket embodiments are identified below as "404", "404a", "404b", etc.

Figure 42:
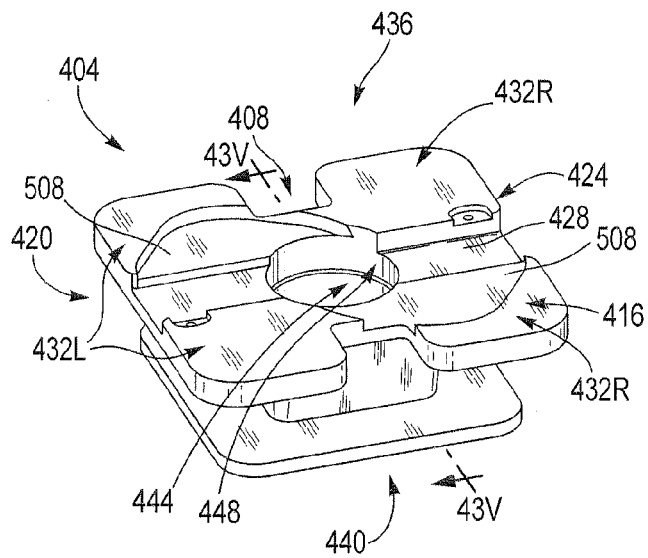
FIG. 42 is a top perspective view the body of the self-ligating orthodontic bracket 404.
Figure 43:
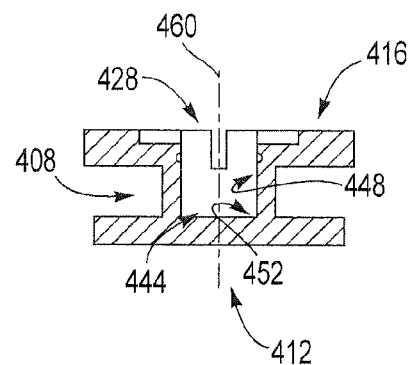
FIG. 43 is a cross sectional view of the body 408 of the self-ligating orthodontic bracket 404.

A self-ligating orthodontic bracket 404 is shown in FIG. 42 having a bracket body 408 with a back 412 and a front surface 416. The bracket body 408 has a left side 420 and right side 424. An archwire slot 428 that has a length generally spanning the extent between the left side 420 to the right side 424 in the front surface 416. Attached to the bracket body 408 are tie wings 432L and 432R, wherein the tie wings 432L are on (or adjacent to) the left side 420 and tie wings 432R are on (or adjacent to) the right side 424. The tie wings 432L and 432R extend outwardly from the body 408, wherein one pair of tie wings 432L and 432R extends away from the body on a generally gingival side 436 (when the bracket 404 is positioned on a patient's tooth), and another pair of tie wings 432L and 432R extends away from the body on a generally acclusal side 440 (when the bracket 404 is positioned on a patient's tooth). The front surface 416 of the bracket body 408 has a generally cylindrical recess 444 therein which extends into the body 408. The cylindrical recess 444 may be substantially defined by a generally circular wall 448 extending into the body 408, wherein the cylindrical recess terminates in a circular floor 452 (FIG. 43). FIG. 43 shows the bracket 404 in cross section.

Figure 44:
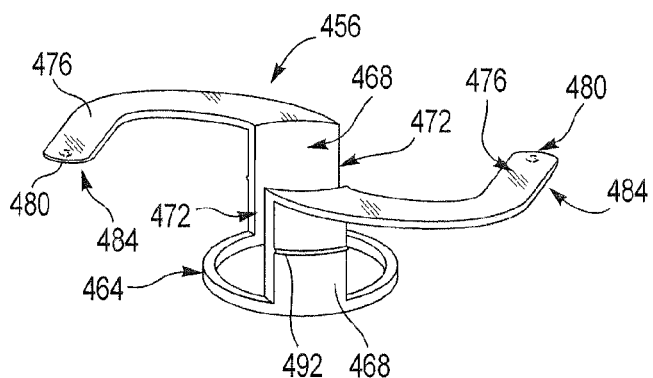
FIG. 44 is a perspective view of the rotatable member of the self-ligating orthodontic bracket 404.

FIG. 44 discloses a rotatable member 456 which, when operably provided in the bracket 404, resides in the cylindrical recess 444 (FIGS. 42 and 43) so that the rotatable member is able to rotate about the central axis 460 (FIG. 43) of the cylindrical recess as described hereinbelow. The rotatable member 456 has a cylindrical portion 464 attached to opposing columns 468 extending at right angles to the cylindrical portion 464. Each of the opposing columns 468 includes an interior column side 472. Attached to each opposing column 468 end that is opposite the cylindrical portion 464 is a C-shaped slot coverable extension 476 (also referred to as merely an "extension"). The extensions 476 each extend perpendicularly from the column 464 to which an end of the extension 476 is attached. Each slot coverable extension 476 also has a free end 480 and an underside 484. The opposing columns 468 have an outer curved surface 488 shaped which fits to the contour of the circular wall 448 of the cylindrical recess 444. Each of the curved surfaces 488 contains a circular groove 492. As an aside, note that the cylindrical portion 464 need not be necessarily cylindrical or circular. Indeed, the cylindrical portion 464 can have various shapes (e.g., hexagonal, octagonal, etc.) as long as it is able to rotate within the cylindrical recess 44 about the central axis 460 of this recess.

Figure 45:
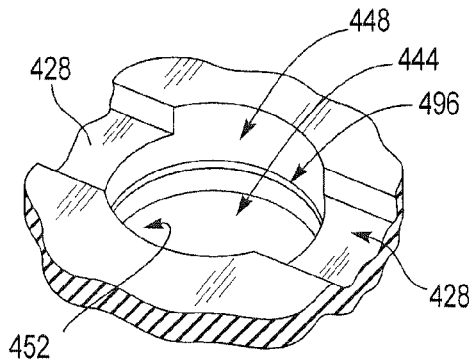
FIG. 45 is a top perspective cutaway view of the body recess of the self-ligating orthodontic bracket 404.

FIG. 45 is an enlarged view of the cylindrical recess 444 disclosing the recess circular wall 448 and a circular protruding ring 496 which seats into the circular grooves 492 (FIG. 44) of the rotatable member 456. In particular, the circular protruding ring 496 and the circular grooves 492 mate together for allowing the rotatable member 456 to be secured in the cylindrical recess 444 and still rotate about the axis 460 (FIG. 43).

Figure 46:
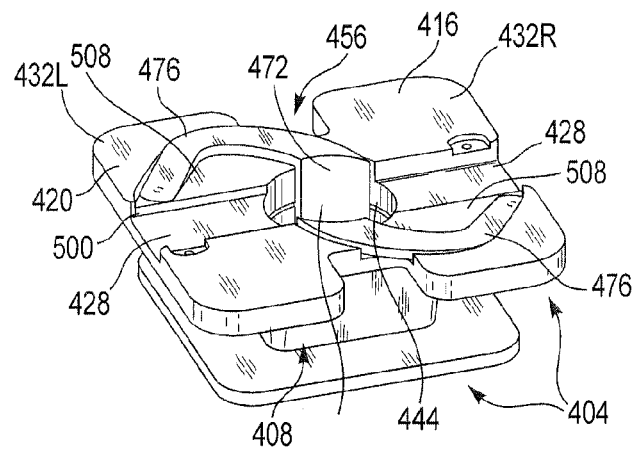
FIG. 46 is a top perspective view of the self-ligating orthodontic bracket 404 in an open position.

FIG. 46 discloses an assembled bracket 404, wherein the rotatable member 456 is inserted in the cylindrical recess 444 of the bracket body 408, and wherein the cylindrical portion 464 is seated against the circular floor 452 (FIG. 43). When the rotatable member 456 is operably coupled to the bracket body 408, one of the slot coverable extensions 476 is positioned on each of the left side 420 and right side 424 of the front surface 416 of the bracket body 408. As shown in FIG. 46, the interior column sides 472 sufficiently align with the archwire slot 428 side walls 500 for allowing an archwire 504 (FIG. 50) to be received within the slot 428 (e.g., to travel continuously from the left end 8 of the archwire slot 428 to the right end 9 of the archwire slot 428, or vice versa). Moreover, note that FIG. 46 also shows the extensions residing in corresponding recesses 508 of the front surface 416 in a manner wherein an archwire 504 to be readily inserted into the slot 428.

Figure 47:
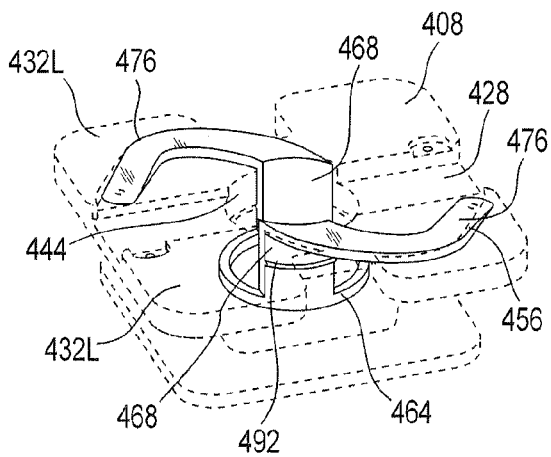
FIG. 47 is a top perspective internal view of the rotatable member resting within a cutout view of the body of the self-ligating orthodontic bracket 404.

FIG. 47 discloses the rotatable member 456 as it sits within the bracket body 408. The circular groove 492 is shown on the outer surface of one of the attached opposing columns 468. FIGS. 46 and 47 show the rotatable member 456 in the open position wherein the C-shaped extensions 476 do not extend over the archwire slot 428. In this open position an archwire 504 (FIG. 50) may be inserted and removed from the archwire slot 428.

Figure 48:
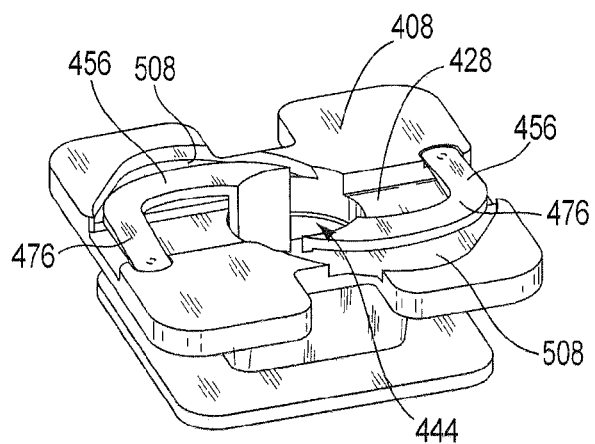
FIG. 48 is a top perspective view of the self-ligating orthodontic bracket 404 with the rotatable member in a closed position.

In FIG. 48 the rotatable member 456 is shown in a counterclockwise rotated configuration, wherein the slot coverable extensions 476 extend over (and partially spans) the archwire slot 428 such that an archwire 504 is restrained to remain within the archwire slot 428. The configuration of the rotatable member 456 shown in FIG. 48 is referred to herein as being in a "closed position", wherein this term refers to the extensions spanning the slot 428.

Figure 49:
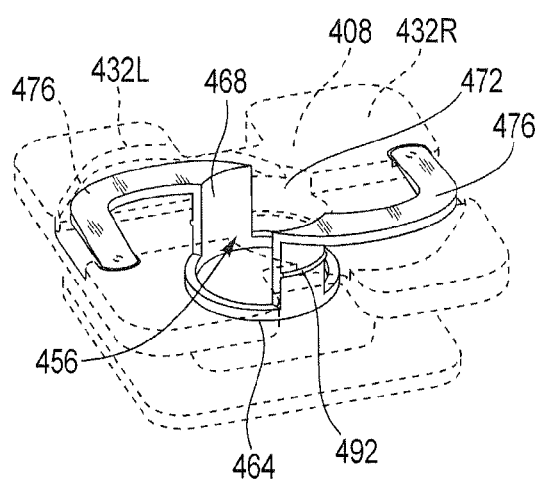
FIG. 49 is a top perspective internal view of the self-ligating orthodontic bracket 404 with the rotatable member in a closed position.

FIG. 49 discloses details of the rotatable member 456 when operably provided within the bracket body 408. The opposing interior column sides 472 allow an archwire 504 to reside therebetween in the archwire slot 428.

Figure 50:
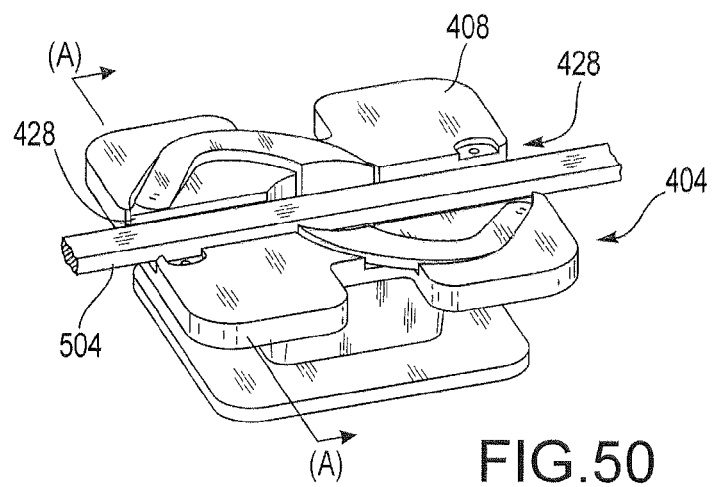
FIG. 50 is a top perspective view of the self-ligating orthodontic bracket 404 with an archwire.
Figure 51A:
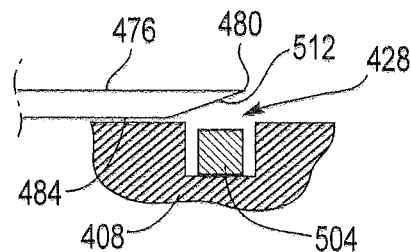
FIGS. 51A, and 51B each show: (a) a same fragmentary cross section of the body 408 of the self-ligating orthodontic bracket of FIG. 50, wherein the cross section is from a sectioning plane (not shown) corresponding to line segment A-A, and (b) a beveled leading edge 512 of the C-shaped slot coverable extension 476.
Figure 51B:
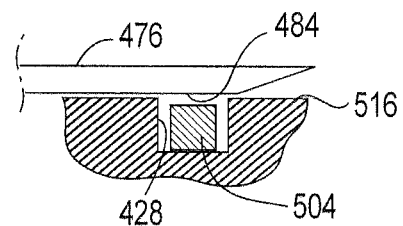

FIG. 50 discloses the rotatable member orthodontic bracket 404 with the rotatable member 456 in the open position and an archwire 504 in the archwire slot 428. FIGS. 51A and 51B are cross sections of the bracket body 408 and the archwire 504 of FIG. 50, wherein the cross section is obtained from a sectioning plane (not shown) containing the line segment identified by the end letters A, wherein the sectioning plane is also perpendicular to the view arrows at the ends of the line segment. In FIG. 51A, a slot coverable extension 476 (extending through the sectioning plane but not cross sectioned) rests upon the bracket body 408 entirely on one side of the slot 428. The free end 480 of this extension 476 includes a beveled leading edge 512 as part of the underside 484, wherein this beveled leading edge 512 facilitates the extension 476 sliding over the archwire 504 to, e.g., obtain the configuration as shown in FIG. 51B wherein this extension spans the slot 512 and also extends over the opposite side 516 of the slot. Note that in the embodiment shown in FIGS. 51A and 51B, the underside 484 is substantially flat or planar such that the extension 476 holds the archwire 504 only loosely within the archwire slot 428; e.g., the extension 476 does not cause or force the archwire into contact with the surfaces of the slot 428 with sufficient force to induce frictional forces therebetween that (for orthodontic purposes) would effectively inhibit movement of the archwire in a direction along the length of the slot.

Figure 52A:
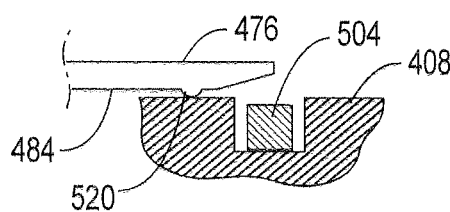
FIGS. 52A and 52B each show: (a) a same fragmentary cross section of the body 408 of the self-ligating orthodontic bracket of FIG. 50 wherein the cross section is from a sectioning plane (not shown) corresponding to line segment A-A, and (b) a protrusion 520 on the underside 484 of the C-shaped slot coverable extension 476.
Figure 52B:
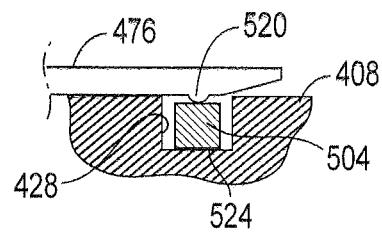

An alternative embodiment of the C-shaped slot coverable extension 476 (from that shown in FIGS. 51A and 51B) is shown in FIGS. 52A and 52B. In particular, FIGS. 52A and 52B show a protrusion 520 that extends outwardly from the underside 484 of the C-shaped extension 476, wherein this protrusion 520 may be used to cause or force the archwire 504 into contact with the surfaces of the slot 428 with sufficient force to induce frictional forces therebetween such that (for orthodontic purposes) such frictional forces effectively inhibit movement of the archwire in a direction along the length of the slot. More particularly, referring to FIG. 52A, this figure discloses the cross-section of FIG. 50 wherein the underside 484 of the extension 476 has the protrusion 520 positioned to the left of the slot 428 in a manner that allows insertion or removal of an archwire 504 from the slot. However, in FIG. 52B, the extension 476 has been moved (e.g., via rotation of the rotatable member 456) such that when the extension 476 restrains the archwire 504 from disengaging from the slot 428, the protrusion 520 contacts the archwire for holding the archwire in place due to pressing the archwire against, e.g., the floor 524 of the slot.

Figure 53A:
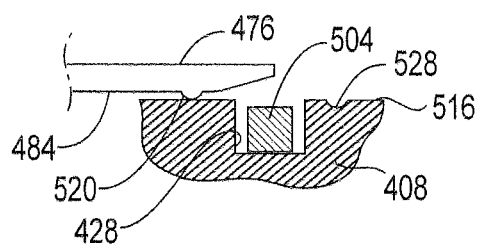
FIGS. 53A and 53B each show: (a) a same fragmentary cross section of the body 408 of the self-ligating orthodontic bracket of FIG. 50 wherein the cross section is from a sectioning plane (not shown) corresponding to line segment A-A, and (b) a protrusion 520 on the underside 484 of the C-shaped slot coverable extension 476 wherein the protrusion is able to mate with a depression or dimple 528.
Figure 53B:
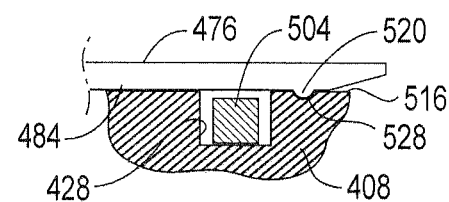

In FIGS. 53A and 53B, the alternative embodiment of the C-shaped slot coverable extension 476 of FIGS. 52A and 52B is shown with the front surface 416 of the bracket having a depression or dimple 528 in the opposite side 516 for loosely securing the archwire 504 in the slot 428. In particular, when the extension 476 is fully rotated counterclockwise to span the slot 428 (FIG. 53B), the protrusion 520 mates with the depression 528 for further securing the rotatable member 456 in its fully rotated position.

Figure 54:
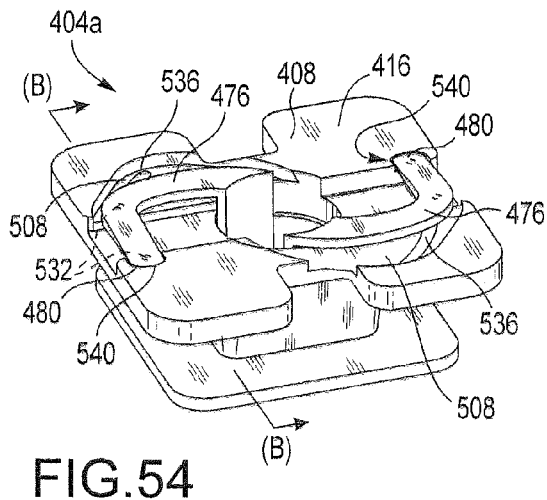
FIG. 54 shows a top perspective view of the self-ligating orthodontic bracket 404 with cutout channels.
Figure 55:
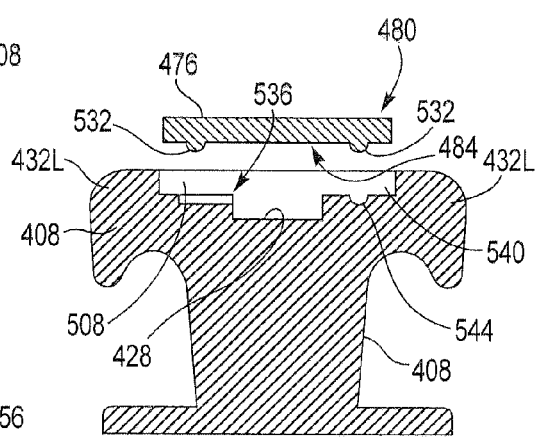
FIG. 55 is a cross section of the body 408 of the self-ligating orthodontic bracket of FIG. 54 wherein the cross section is from a sectioning plane (not shown) corresponding to line segment B-B.

FIGS. 54 and 55 show another embodiment of a self-ligating orthodontic bracket (identified by the label 404a), wherein the cross section of FIG. 55 is obtained from a sectioning plane (not shown) containing the line segment identified by the end letters B of FIG. 54, wherein this sectioning plane is also perpendicular to the view arrows at the ends of this line segment, and wherein the cross sectioned extension 476 is separated from the bracket body 408 to more clearly show the features thereof. In particular, FIGS. 54 and 55 show a pair of protrusions 532 on the underside 484 of each of the extensions 476 and near the free end 480 thereof. These paired protrusions 532 fit into a corresponding recess channel 536 on the bracket front surface 416, and slide in this recess channel when the rotatable member 456 is rotated such that the protrusion of the pair that is closest to the free end 480 of the extension 476 (having the protrusion pair thereon) may exit/enter this recess channel and enter/exit the slot 428. Thus, for each of the recess channels 536 there is a corresponding pair of protrusions 532 that slide therein, during the rotation of the rotatable member 456.

When the rotatable member 456 (of the embodiments of, e.g., FIGS. 46, 48, 50, 54 and 55) is fully rotated in the counterclockwise direction, for each extension 476, the free end 480 thereof enters a cutout 540 on the opposing side of the slot 428, and the protrusion 532 closest to this free end 480 enters (and seats with) a dimple 544 for further securing the rotatable member 456 in its fully rotated position.

Figure 56:
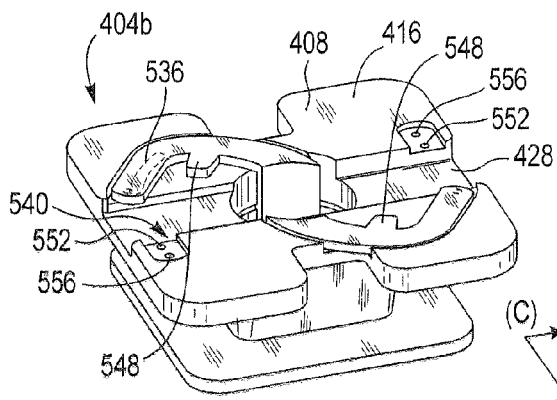
FIG. 56 shows a top perspective view of the self-ligating orthodontic bracket with slot coverable extension tabs in an open position.
Figure 57:
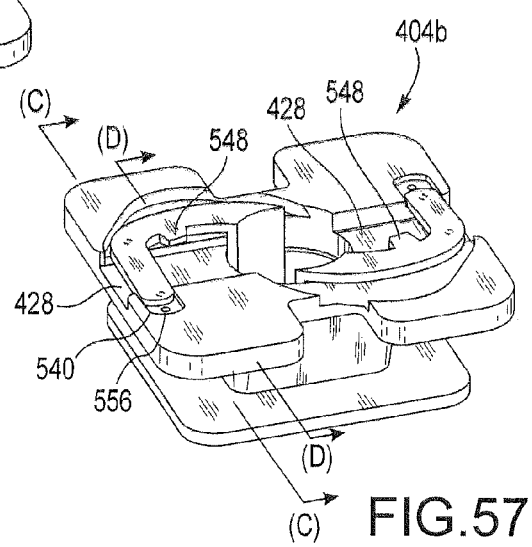
FIG. 57 shows a top perspective view of the self-ligating orthodontic bracket with slot coverable extension tabs in a closed position.

FIGS. 56, 57, 58A, 58B, 59A, and 59B show another embodiment of a self-ligating orthodontic bracket (identified by the label 404b), wherein the C-shaped extensions 476 include corresponding pairs of protrusions 532 as described with reference to FIGS. 54 and 55. FIGS. 56 and 57 show a tab 548 on each extension 476 such that the tab extends towards the archwire slot 428. The surface of each tab 548 facing the front surface 416 of the bracket body 408 may be smooth or may contain a protrusion 550 (FIGS. 59A, 59B) for contacting the archwire (in the slot 428), e.g., so that such contact induces frictional forces between the archwire 504 and one or more of the slot surfaces for effectively inhibiting movement of the archwire in a direction along the length of the slot. FIG. 56 further shows recess channels 536. However, the channels 536 are optional and not shown in FIGS. 58A, 58B, 59A, and 59B. FIG. 57 shows the extensions 476 is in a first of two closed positions wherein the extensions 476 span the slot 428. In the first closed position of FIG. 57, for each pair of protrusions 532, the protrusion nearest its corresponding free end 480 (this protrusion referred to hereinbelow as the "terminal protrusion") is seated in a depression or dimple 552 closest to the archwire slot 428 (FIG. 56). FIG. 57 further discloses that the tabs 548 do not extend into the archwire slot 428. When the rotatable member 456 is rotated further in the counterclockwise direction (to a "second closed position"), each of the two terminal protrusions (one per extension 476) may enter (and seat therewith) a second dimple or depression 556. In the second closed position, the tabs 548 at least extend over the slot 428, and in at least one embodiment span the slot.

Figure 58A:
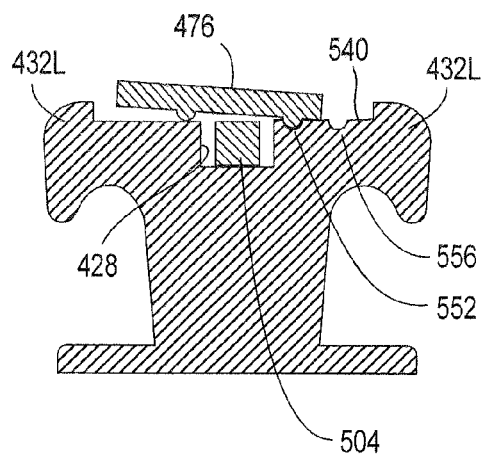
FIGS. 58A and 58B are cross-sectional views of FIG. 57 through the line segment C-C.
Figure 58B:
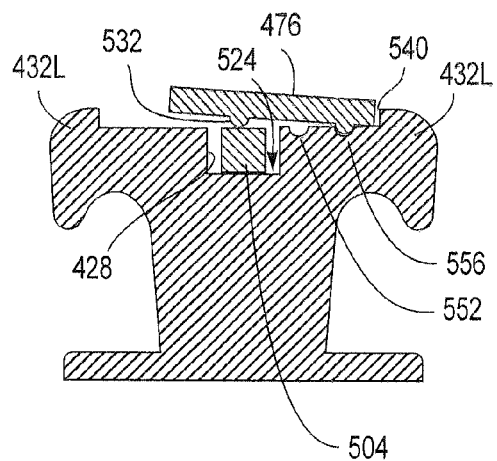

FIG. 58A shows a cross-section of FIG. 57, wherein this cross section is obtained from a sectioning plane (not shown) containing the line segment identified by the end letters "C", and wherein this sectioning plane is also perpendicular to the view arrows at the ends of this line segment. FIG. 58B is a cross-section related to FIG. 57. That is, FIG. 58B is a cross-section of FIG. 57 through the line segment identified by the end letters "C", but with the rotatable member 456 in the second closed position rather than the first closed position. Note that in the second closed position illustrated in FIG. 58B, the protrusion 532 contacting the archwire 504 causes or forces the archwire into contact with the surfaces of the slot 428 (e.g., the floor 524 thereof) with sufficient force to induce frictional forces therebetween such that (for orthodontic purposes) such frictional forces effectively inhibit movement of the archwire in a direction along the length of the slot.

Figure 59A:
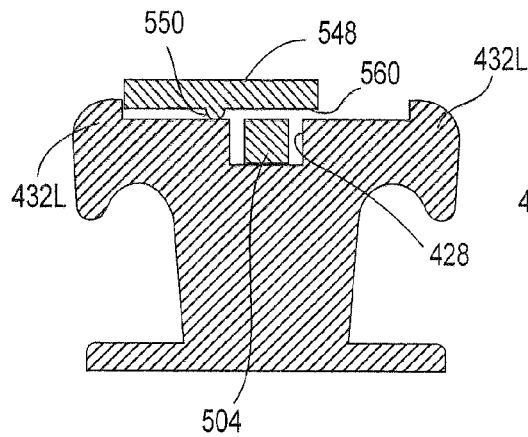
FIGS. 59A and 59B are cross-sectional views of FIG. 57 through the line segment D-D.
Figure 59B:
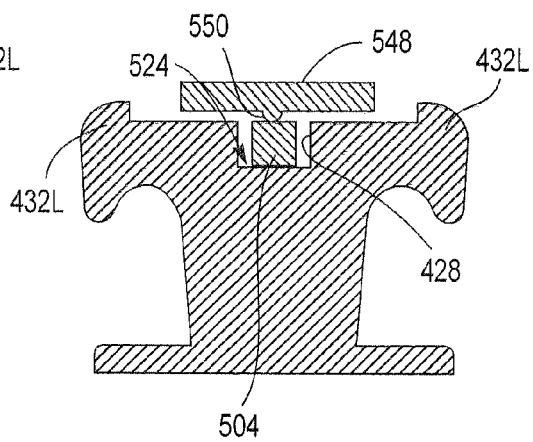

FIGS. 59A and 59B, respectively, correspond to FIGS. 58A and 58B except that the sectioning plane of FIG. 57 is through the line segment D-D. In particular, FIGS. 59A and 59B are cross-sections of the embodiment of FIG. 57 in, respectively, the first closed position and the second closed position, wherein these cross sections are obtained from a sectioning plane (not shown) containing the line segment identified by the end letters "D" (FIG. 57), and wherein this sectioning plane is also perpendicular to the view arrows at the ends of this line segment. Note that in the second closed position illustrated in FIG. 59B, the protrusion 532 contacting the archwire 504 causes or forces the archwire into contact with the surfaces of the slot 428 (e.g., the floor 524 thereof) with sufficient force to induce frictional forces therebetween such that (for orthodontic purposes) such frictional forces effectively inhibit movement of the archwire in a direction along the length of the slot. In particular, FIG. 59A discloses the tab 548 with a smooth portion of underside 560 of the tab spanning the slot 428 opening for thereby holding the archwire 504 loosely therein. FIG. 59B shows the tab 548 further rotated in the counterclockwise direction so that the protrusion 550 contacts the archwire 504 causing or forcing the archwire 504 into contact with the surfaces of the slot 428 (e.g., the floor 524 thereof) with sufficient force to induce frictional forces therebetween such that (for orthodontic purposes) such frictional forces effectively inhibit movement of the archwire in a direction along the length of the slot.

When an orthodontic bracket is placed on a tooth, it is ideally positioned with a slot of the bracket at a predetermined distance from the incisal edge or occlusal surface of the tooth. In addition, the lengthwise direction of the bracket slot may be placed at a right angle to the long axis of the tooth. FIGS.

Figure 60:
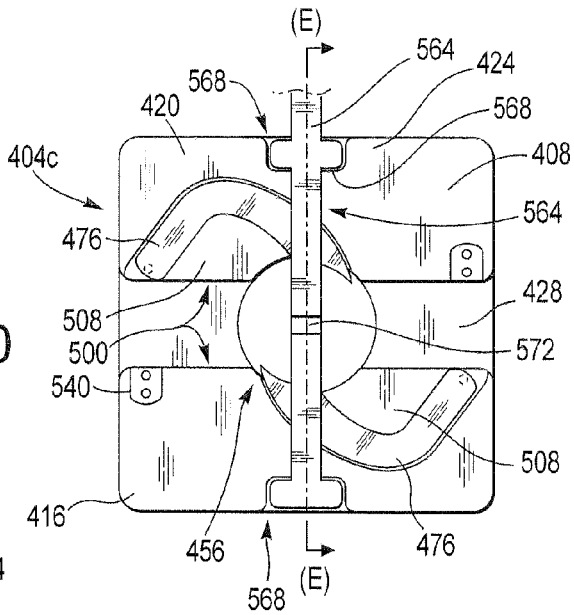
FIG. 60 shows a top perspective view of the self-ligating orthodontic bracket with an index pin.
Figure 61:
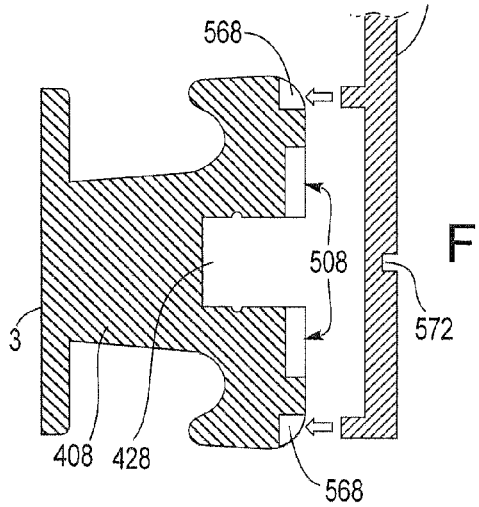
FIG. 61 shows a cross-sectional view of the self-ligating orthodontic bracket of FIG. 60 through the line segment E-E.

60 and 61 show another embodiment of a self ligating orthodontic bracket (identified by the label 404c) having a rotatable member 456. FIG. 61 is a cross section of FIG. 60, wherein this cross section is obtained from a sectioning plane (not shown) containing the line segment identified by the end letters "E" (FIG. 60), and wherein this sectioning plane is also perpendicular to the view arrows at the ends of this line segment. FIGS. 60 and 61 also show an index pin 564 attached to the orthodontic bracket 404c, wherein this pin assists an orthodontist (or technician) in visualizing the correct placement of the bracket 404 on a patient's tooth, and in particular, relative to the tooth's longitudinal axis (extending from the tooth's incisal edge or occlusal surface toward the root of the tooth as one skilled in the art will understand), and additionally, relative to a distance from the tooth's incisal edge or occlusal surface as one skilled in the art will also understand. The index pin 564 is attached to the bracket 404c, e.g., by the use of a pair seats 568 in the front surface 416 of the bracket 404c, wherein the seats may be substantially midway between the left side 420 and the right side 424 of the bracket. FIGS. 60 and 61 further show a measuring notch 572 substantially midway between the slot side walls 500 for thereby assisting the orthodontist (or technician) in the positioning of the bracket 404c so that the slot 428 is properly longitudinally positioned relative to the incisal edge or occlusal surface of the tooth upon which the bracket 404c is to be placed.

Figure 62:
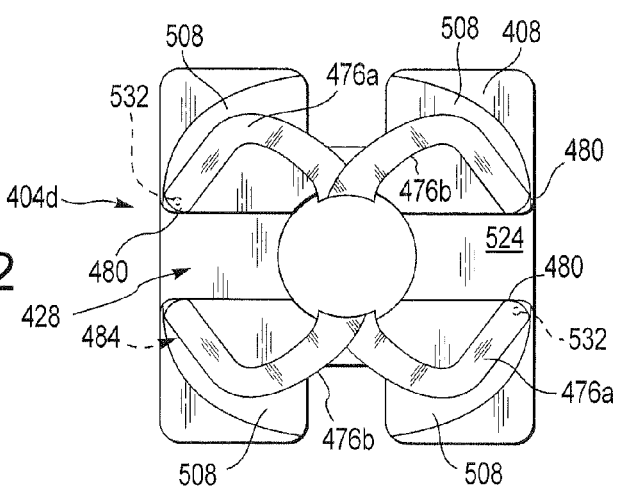
FIG. 62 shows a top perspective view of the self-ligating orthodontic bracket with a second pair of C-shaped slot coverable extensions 476, all such extensions in the open position.
Figure 63:
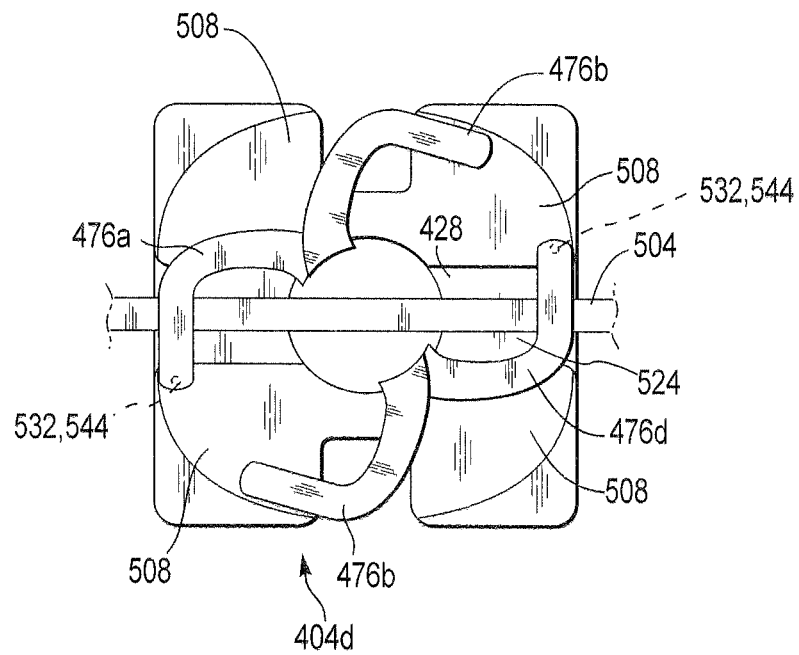
FIG. 63 shows a top perspective view of the self-ligating orthodontic bracket with a second pair of C-shaped slot coverable extensions 476 wherein the rotatable member is turned counterclockwise into a closed position.
Figure 64:
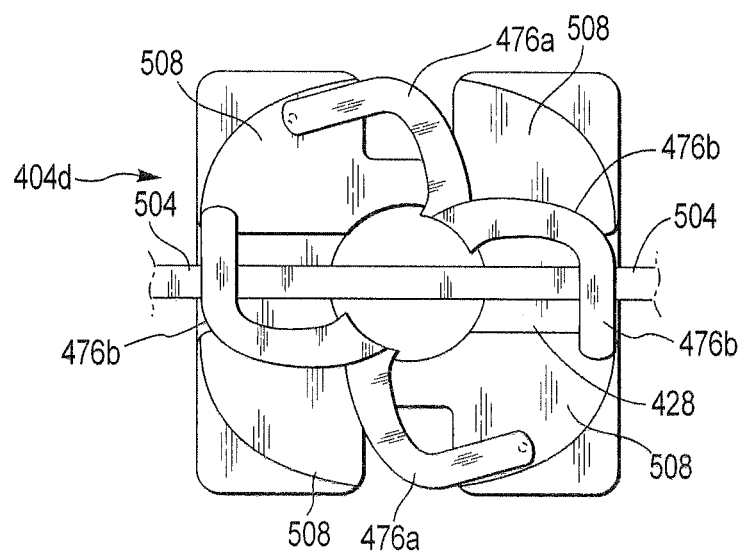
FIG. 64 shows a top perspective view of the self-ligating orthodontic bracket with a second pair of C-shaped slot coverable extensions 476 wherein the rotatable member is turned clockwise into a closed position.

FIGS. 62-64 disclose another self ligating bracket embodiment 404d, wherein there are two pairs of C-shaped slot coverable extensions 476a and 476b. FIG. 62 shows the bracket 404d in an open position, wherein an archwire 504 may be readily inserted into the slot 428. The first pair of extensions 476a have protrusions 532 on the under side near their free ends 480. The second pair of extensions 476b have a flat underside 484 not including a protrusion 532. FIG. 63 shows the rotatable member 456d having the extensions 476a rotated counterclockwise wherein the underside protrusions 532 engage a depression or dimple 544 (for thereby holding the archwire 504 within the slot 428, wherein the undersides that contact the archwire include a depression, dimple or other thickness (not shown) that is able to cause or force the archwire into contact with the surfaces of the slot 428 (e.g., the floor 524 thereof) with sufficient force to induce frictional forces therebetween such that (for orthodontic purposes) such frictional forces effectively inhibit movement of the archwire in a direction along the length of the slot. FIG. 64 shows the rotatable member 456 rotated clockwise wherein the second extensions 476b have a flat undersides that contact and hold the archwire 504 loosely in the slot 428 so that, e.g., the archwire is able to slide within the slot (under typical orthodontic forces) substantially parallel to the length of the slot.

Figure 65:
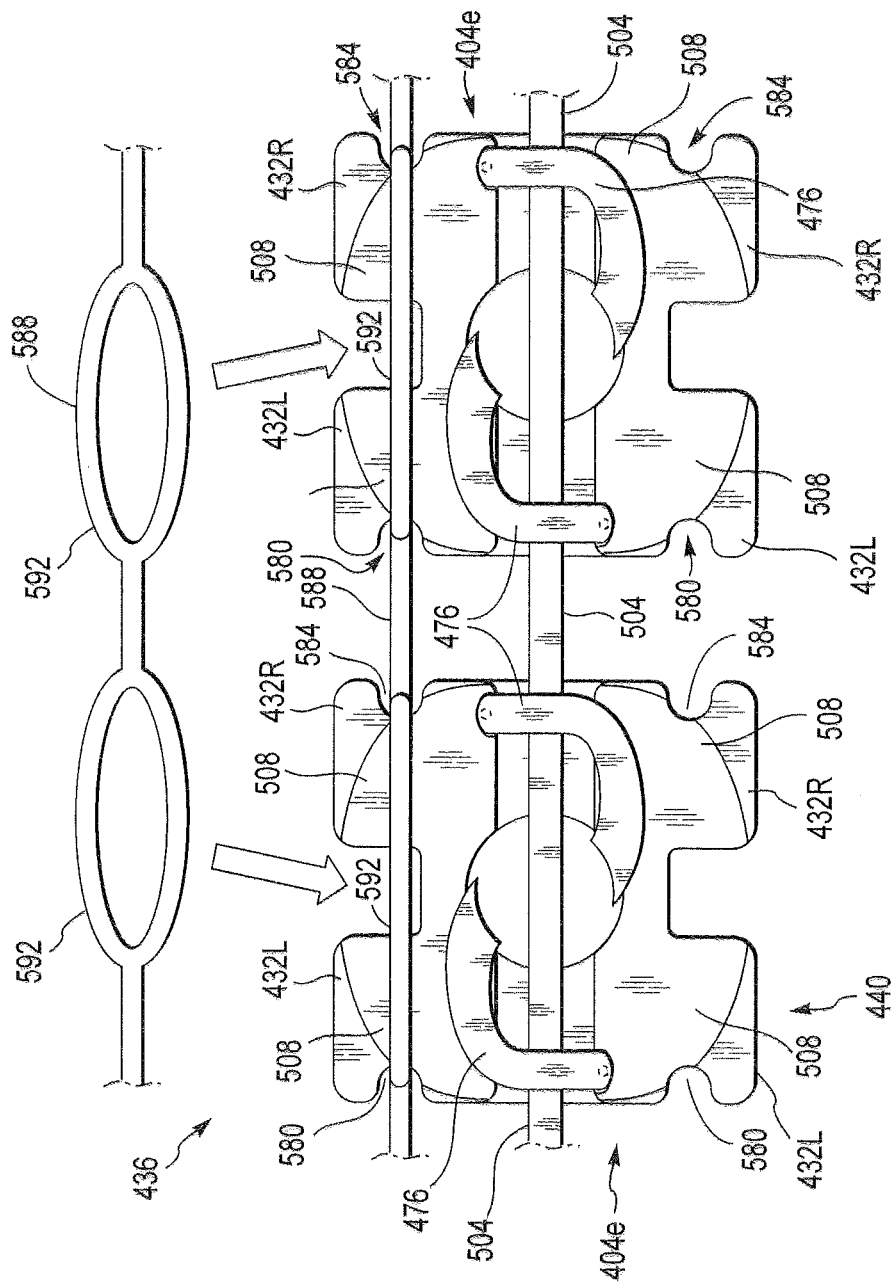
FIG. 65 shows top perspective views of a pair of self-ligating orthodontic brackets with notches and attached elastomeric chains.

FIG. 65 discloses bracket 404e embodiment. The bracket 404e includes a modification of the bracket tie wings wherein the upper and lower left tie wings 432L have notches 580 and the upper and lower right tie wings have notches 584. The notches 580 and 584 allow attachment of orthodontic elastomeric chains 588 to the tie wings 432L and 432R on the gingival side 436 and/or to the tie wings 432L and 432R on the occlusal side 440. Elastomeric chains 588 include a series of connected islets 592 made from an elastic material. The elastomeric chains 588 are normally used to close spaces between teeth, rotate teeth, and/or maintain the lack of spacing between teeth. The elastomeric chains 588 may circle all four tie wings 432L and 432R of the bracket 404e for securing the archwire 504 in the archwire slot 428. In FIG. 65, the elastomeric chain 588 encircles only a gingival pair of tie wings 432L and 432R. The elastomeric chain 588 can be changed without disturbing the archwire 508 or, conversely, the archwire 508 can be changed without disturbing the elastomeric chain 588.

The bracket embodiments described hereinabove may include integral hooks for rubber band wear by a patient. Channels may be in such brackets to receive removable hooks for rubber band and other attachments.

Figure 66:
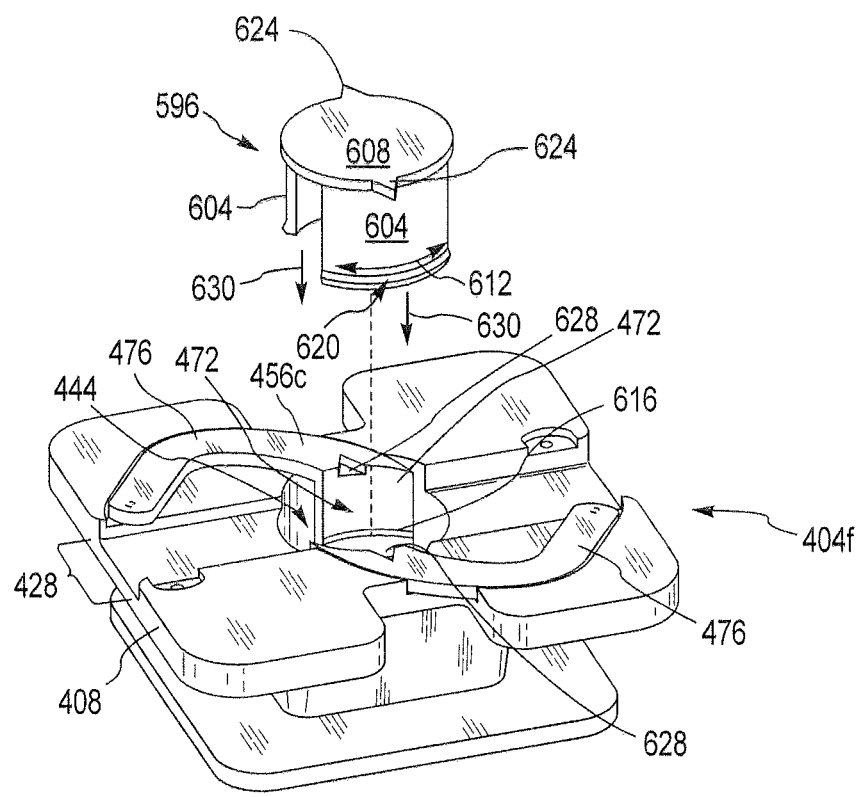
FIG. 66 shows a top perspective view of the self-ligating orthodontic bracket with an attachable rotatable member.

FIG. 66 shows a further bracket embodiment 404f, wherein an attachable cover 596 for locking into the cylindrical interior of the rotatable member 456f. In particular, the attachable cover 596 includes arcuate shaped columns 604 extending from a slot covering 608. Each of the arcuate columns 604 has an arcuate extent 612 that is for mating with a corresponding one of the interior column sides 472 of the rotatable member 456f, wherein when mated, each arcuate extent 612 is substantially coextensive with a corresponding extent of its mated interior column side 472. Each of the interior column sides 472 includes a recess 616 (alternatively ridge) for mating with a corresponding ring 620 on the exterior surface of one of the arcuate shaped columns 604 for securing this arcuate shaped column to the rotatable member 456f. Additionally, the attachable cover 596 includes alignment appendages 624 for mating with alignment recesses 628 so that when the arcuate shaped columns 604 are inserted into the cylindrical recess 444 of the bracket body 408 (as arrows 630 so indicate), an orthodontist (or technician) can be confident that the arcuate shaped columns align with interior columns sides 472 for properly mating the rings 620 with the recesses 616. Accordingly, after an archwire 504 (not shown in FIG. 66) is provided in the slot 428, the attachable cover 596 can be inserted into the cylindrical recess 444 and mated with the rotatable member 456f (via both the rings 620 and the alignment appendages 624) for thereby causing the portion of the slot 428 extending across the cylindrical recess to be covered by the slot covering 608. Subsequently (or prior to), assembly of the combination of the rotatable member 476a and the attachable cover 596, this assembly can be rotated, e.g., counter clockwise, within the bracket body 408 so that the C-shaped slot coverable extensions 476 also cover the slot 428 and archwire 504 therein as described hereinabove.

Figure 70:
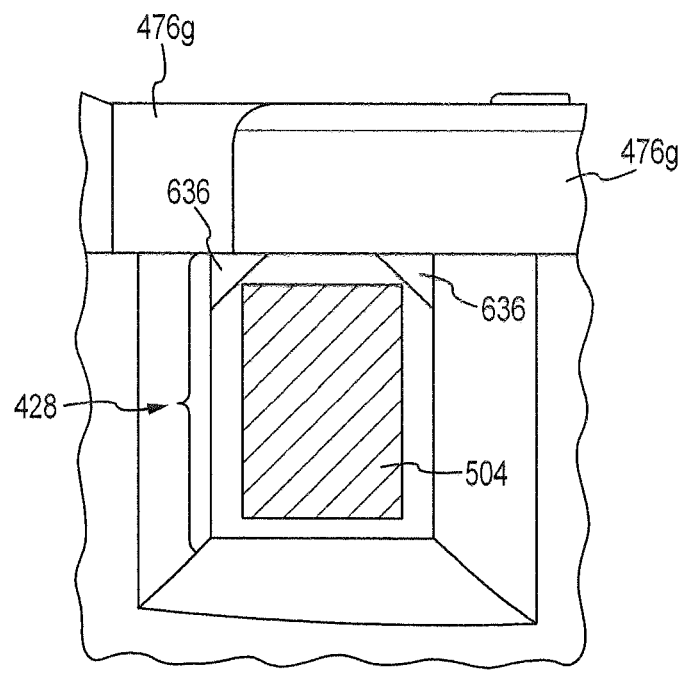
FIG. 70 shows a detailed end view of the slot 428 of the bracket 404g when the bracket is in the closed passive configuration.
Figure 71:
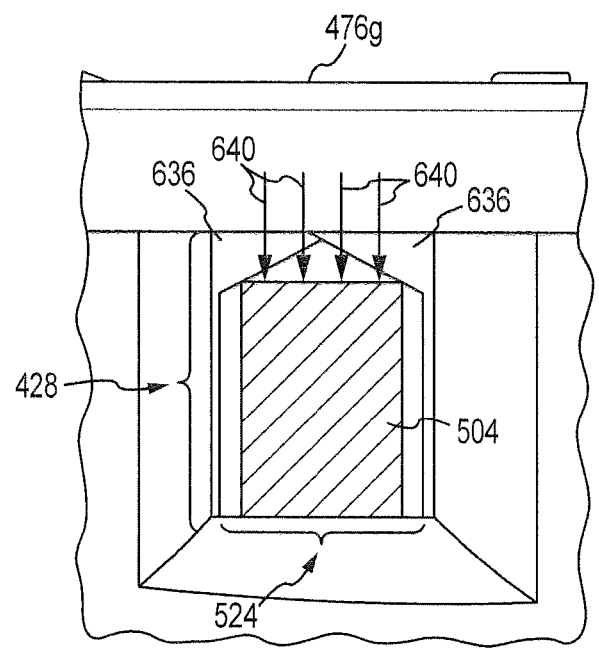
FIG. 71 shows a detailed end view of the slot 428 of the bracket 404g when the bracket is in the closed active configuration.
Figure 72:
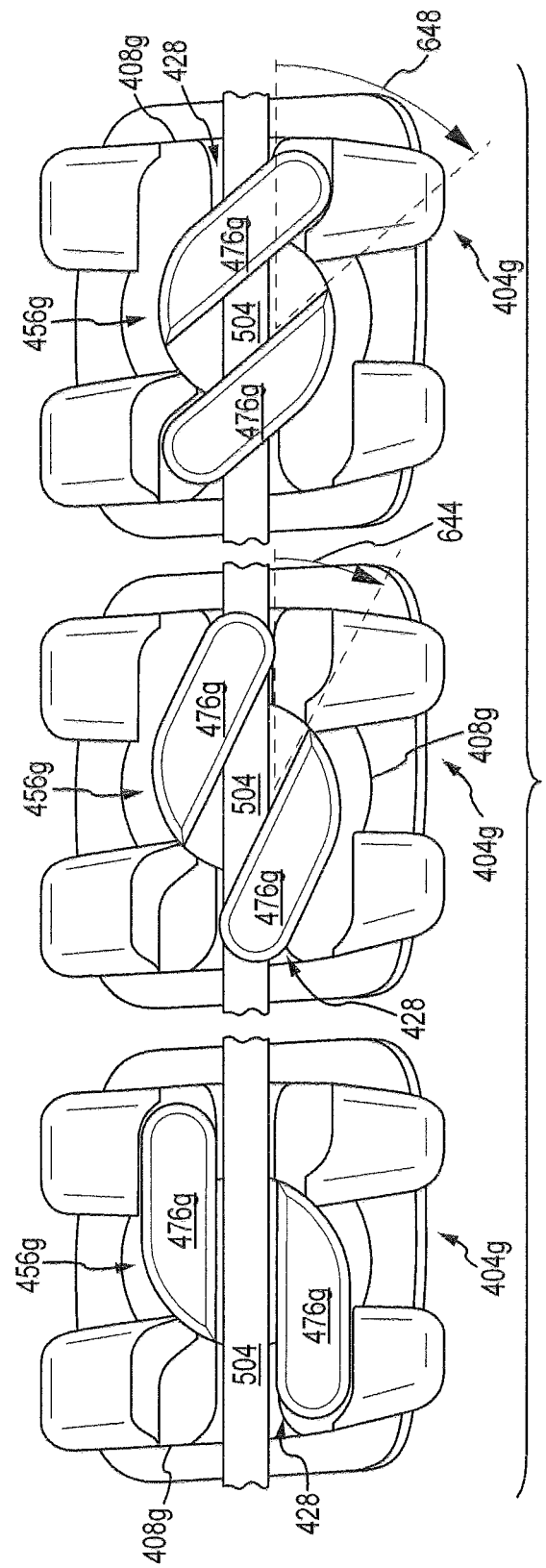
FIG. 72 shows the bracket 404g in side by side configurations of open, passively closed, and actively closed.
Figure 73:
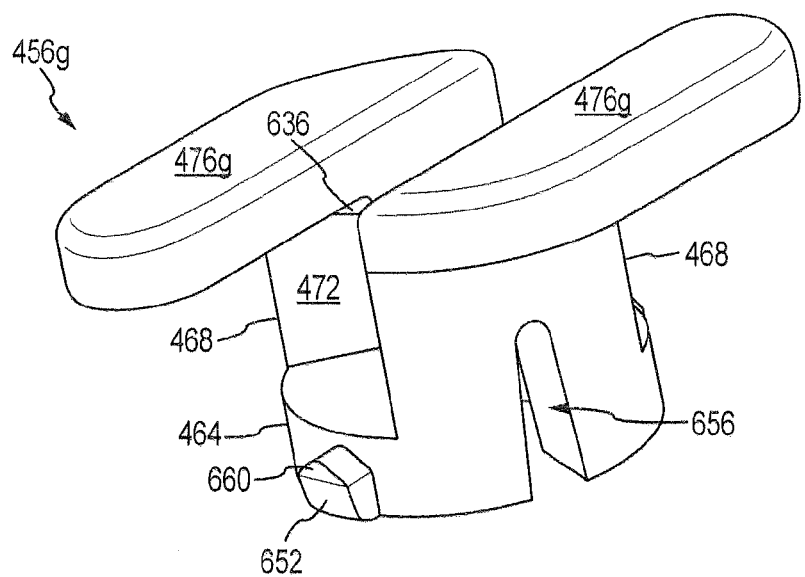
FIG. 73 shows an embodiment of the slot coverable rotatable member 456g for the bracket 404g.

FIGS. 67-75 show an alternative embodiment of a bracket 404g having a rotatable member 456g which, in turn, includes slot coverable extensions 476g that are substantially straight and bar shaped. FIGS. 67A and 67B show the rotatable member 456g in the open position wherein the archwire 504 is not secured in the slot 504 by the extensions 476g. Alternatively, FIGS. 68A and 68B show the rotatable member 456g in a first closed position, wherein the archwire 504 is passively restrained to the slot 504. Additionally, FIGS. 69A and 69B show the rotatable member 456g in a second closed position, wherein the archwire 504 is actively restrained to reside in the slot 504. Note that FIGS. 70 and 71 show magnified views of the archwire 504 being restrained to the slot 428, respectively, in a passive configuration (as in FIG. 68), and in an active configuration (as in FIG. 69). In particular, FIGS. 70 and 71 more clearly show archwire restraining wedges 636 attached to the slot facing side of each of the extensions 476g, wherein in the active configuration of FIG. 71, these wedges exert a force(s) (indicated by arrows 640) for pressing the archwire 504 against the slot floor 534. Note that such a wedge 636 also shown in FIG. 73, and FIG. 76 showing an alternative embodiment of the rotatable member as described hereinbelow.

In FIG. 72, all three bracket 404g configurations: open, passively closed, and actively closed are shown from left to right, wherein the difference these configurations is primarily the rotation of the rotatable member 456g relative to the bracket body 408g. In particular, relative to the (left most) open bracket configuration in FIG. 72, the passively closed (middle) bracket configuration has the rotatable member 456g rotated through an angle 644, and the actively closed (right most) bracket configuration has the rotatable member rotated through an angle 648. Note that the angle 644 may be in a range of 20° to 45°, and the angle 648 may be in a range of 30° to 90°.

Figure 74:
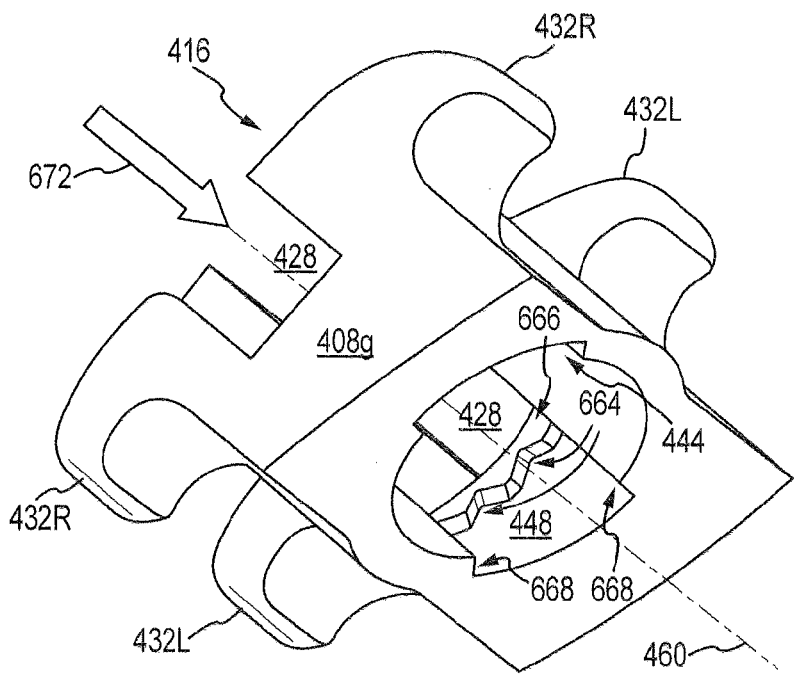
FIG. 74 shows an embodiment of the bracket body 408g of the bracket 404g.
Figure 75:
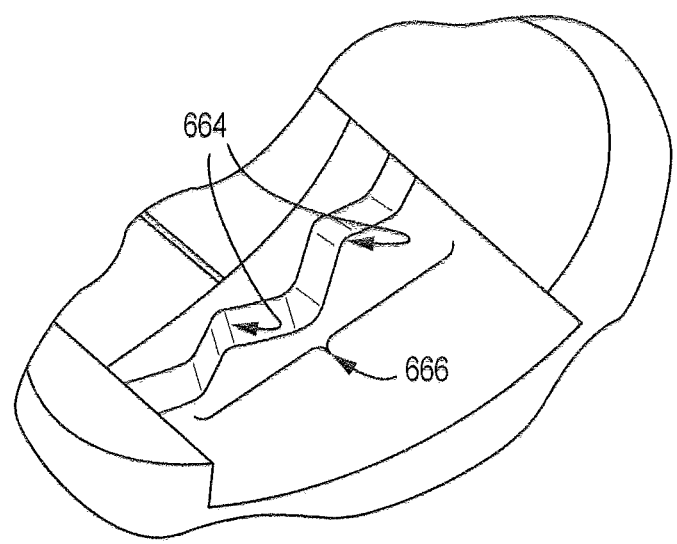
FIG. 75 is an enlarged view of a portion of FIG. 74.

FIGS. 73 and 74, respectively, show an embodiment of the rotatable member 476g, and a corresponding bracket body 408g for the bracket 404g. The rotatable member 476g includes at least one tab 652 extending outwardly from the cylindrical portion 464, and a gap 656. When the rotatable member 476g is operably assembled with the bracket body 408g of FIG. 74, the peak 660 of the tab 652 is moveable from one notch 664 (FIG. 74) to another such notch of a bank 666 of notches provided on the wall 448 of the cylindrical recess 444. Note that although only two notches 664 are shown, three, four or more notches may be provided for rotating the rotatable member 456g in discrete increments within the body 408g. Additionally, the notches 664 may vary in their extent directed forward the central axis 460 so that, e.g., the peak 660 seats in the notches by pressing radially outward from the central axis 460 as shown in FIG. 75. Moreover, stop walls 668 prevent the tab 652 from rotating beyond the extent of the notches 664. Note that in one embodiment, there may be at least two such tabs 652 provided, e.g., on opposite sides of the perimeter of the cylindrical portion 464 and a corresponding set of notches The rotatable member 476g may be provided in the recess 444 by insertion from the front surface 416 of the body 408g as indicated by the arrow 672 (FIG. 74). The gap 656 in the rotatable member 456g allows the cylindrical portion 464 and the columns to compress sufficiently for the tab 652 to be inserted into the recess 444 beyond the notches 664. Accordingly, once the cylindrical portion 464 is sufficiently inserted into the recess 444 so that the tab(s) 652 pass the bank(s) 666 of notches, the cylindrical portion expands so that at least one tab enters a recessed area of the wall 448 bounded by two of the stop walls 668 and one of the banks 666 therebetween. Thus, once a tab 652 enters such a recessed area, the bank 666 acts as a ledge for securing or locking the cylindrical portion 464 into the recess 444, but also has a range of rotation (about the axis 460) corresponding to the separation between the stop walls 668 bounding the tab's recessed area. In particular, the bank In one embodiment, a resilient component (e.g., a spring) may bias the tab 652 toward the notches 664 so that the peak 660 seats within one of the notches. In another embodiment, the gap 656 may be configured so that when a rotational force is applied to the rotatable member 456g, the tab 652 moves from one of notches to another.

Figure 76:
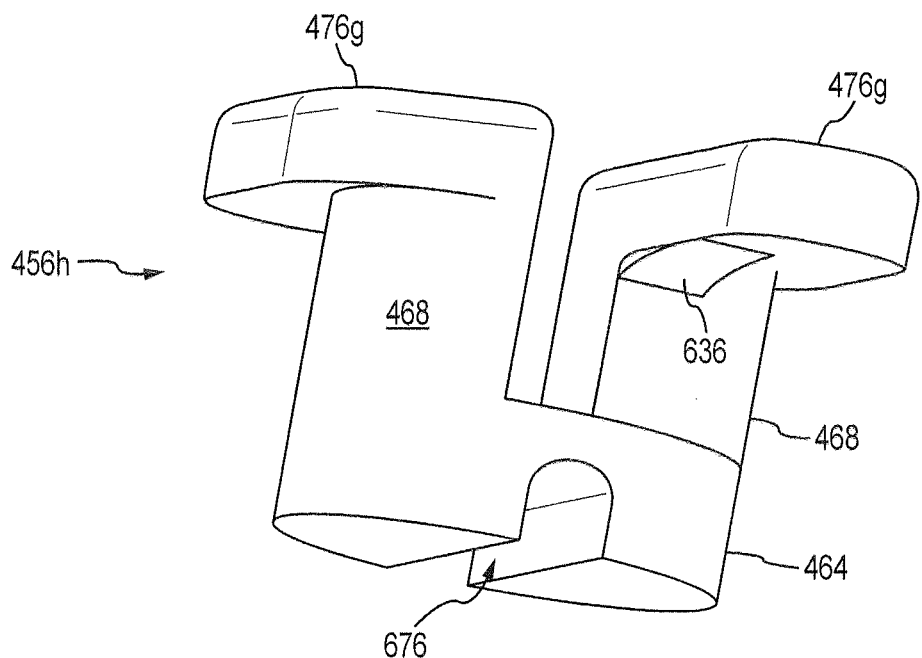
FIGS. 76 and 77 show another embodiment of the rotatable member (labeled 476h) for the bracket 404g.
Figure 77:
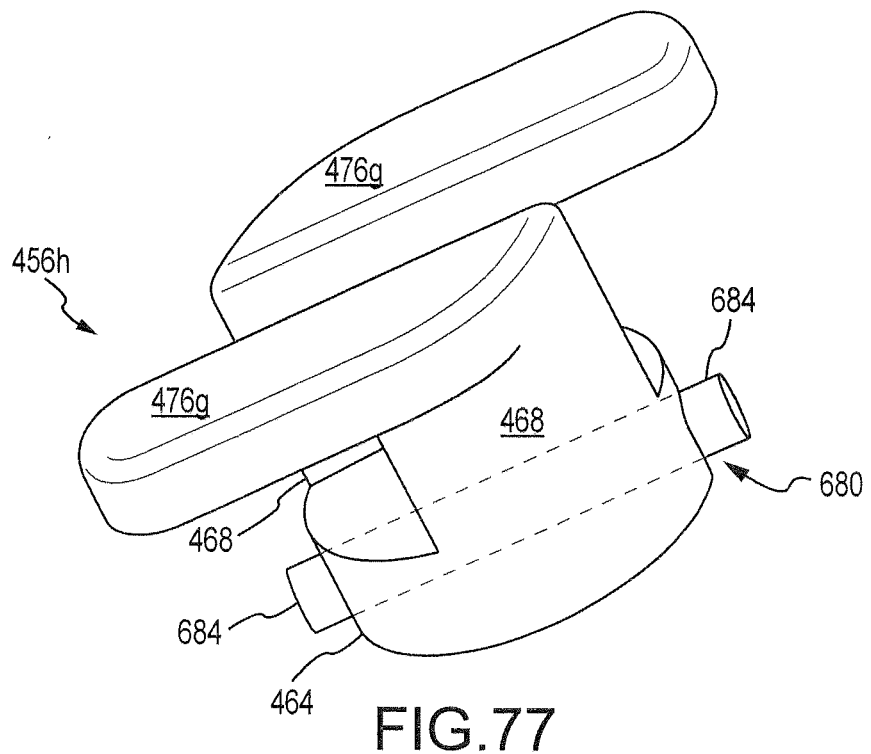

FIGS. 76 and 77 show an alternative embodiment of the rotatable member (denoted 456h), wherein the tab 652 and the gap 656 may be replaced by notch 676 in the base of the cylindrical portion 464, and a pin 680 (FIG. 77) that is provided in the notch 676. The rotatable member 465h, minus the pin 680, is inserted into the body 408g (FIG. 74) in the direction as shown by the arrow 672. However, since there is no tab (or other projection) extending outwardly beyond the perimeter of the cylindrical portion 464, the rotatable member 456h slides into the body recess 444 without substantial compression (if any). Subsequently, once the rotatable member 456h (minus the pin 680) is provided in the recess 444, the pin is welded (or otherwise secured, e.g., by fusing, gluing, etc.) into the notch 676. Accordingly, each of the pin extensions 684 that extend outwardly from the perimeter of the cylindrical portion 464 and operate within the recess 444 of the body 408g substantially as a tab 652 of FIG. 73 in that each such pin extension may seat in one of the notches 664 of a corresponding bank 666 of such notches. Note that the pin 680 is shown as cylindrical in FIG. 77, and in one embodiment may be a small round niti or stainless steel wire. However, the pin 680 (or at least the extensions 684 thereof) may have various shapes, including a cross section substantially identical to the tab 652, and/or a rounded end for more readily sliding from one notch 664 to another.

Figure 78:
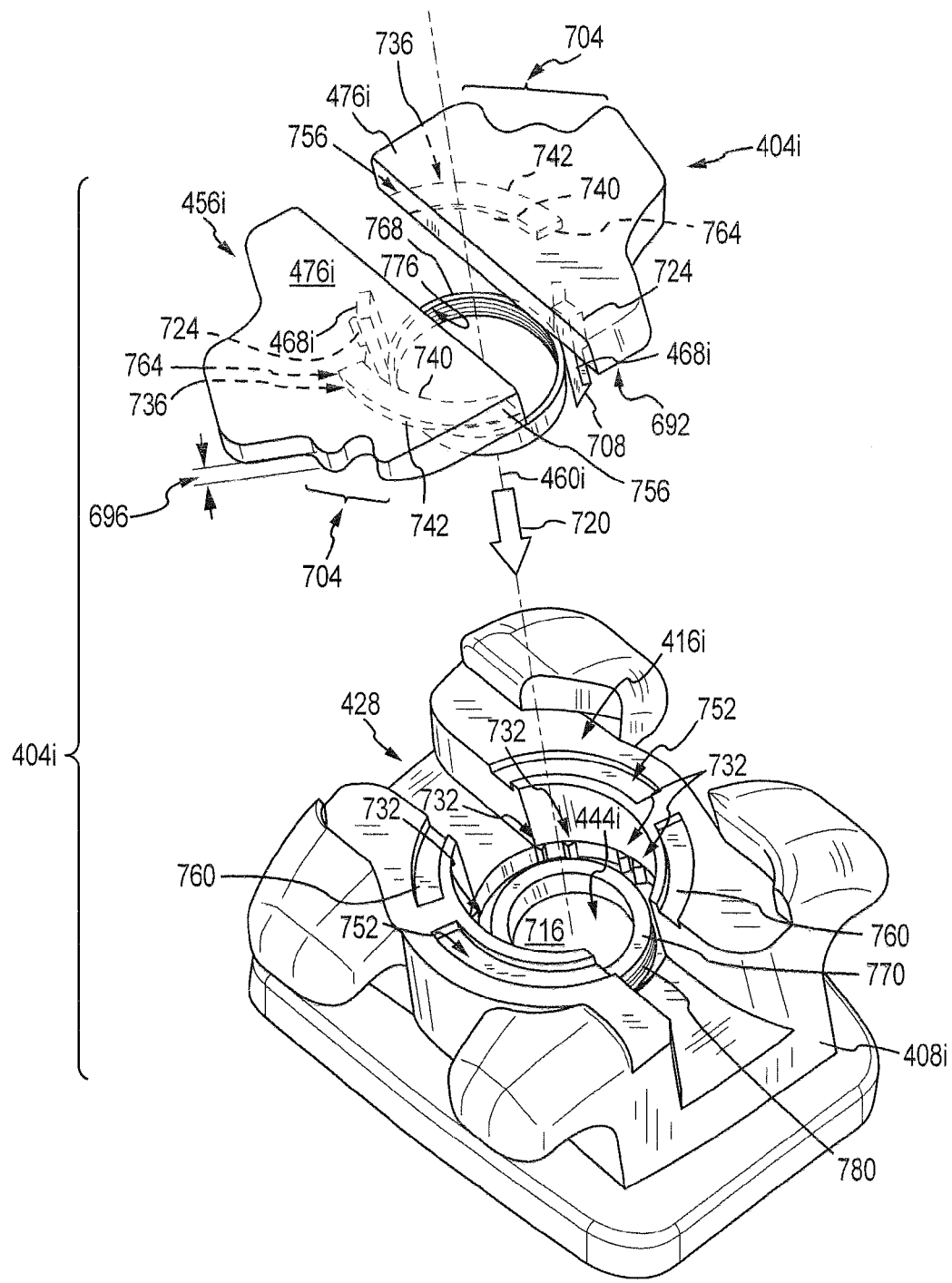
FIG. 78 is a perspective view of another embodiment of a self-ligating orthodontic bracket (404i) with a slot covering rotatable member 456i, wherein the rotatable member is separated from the bracket body 404i to more clearly show internal bracket features.
Figure 79:
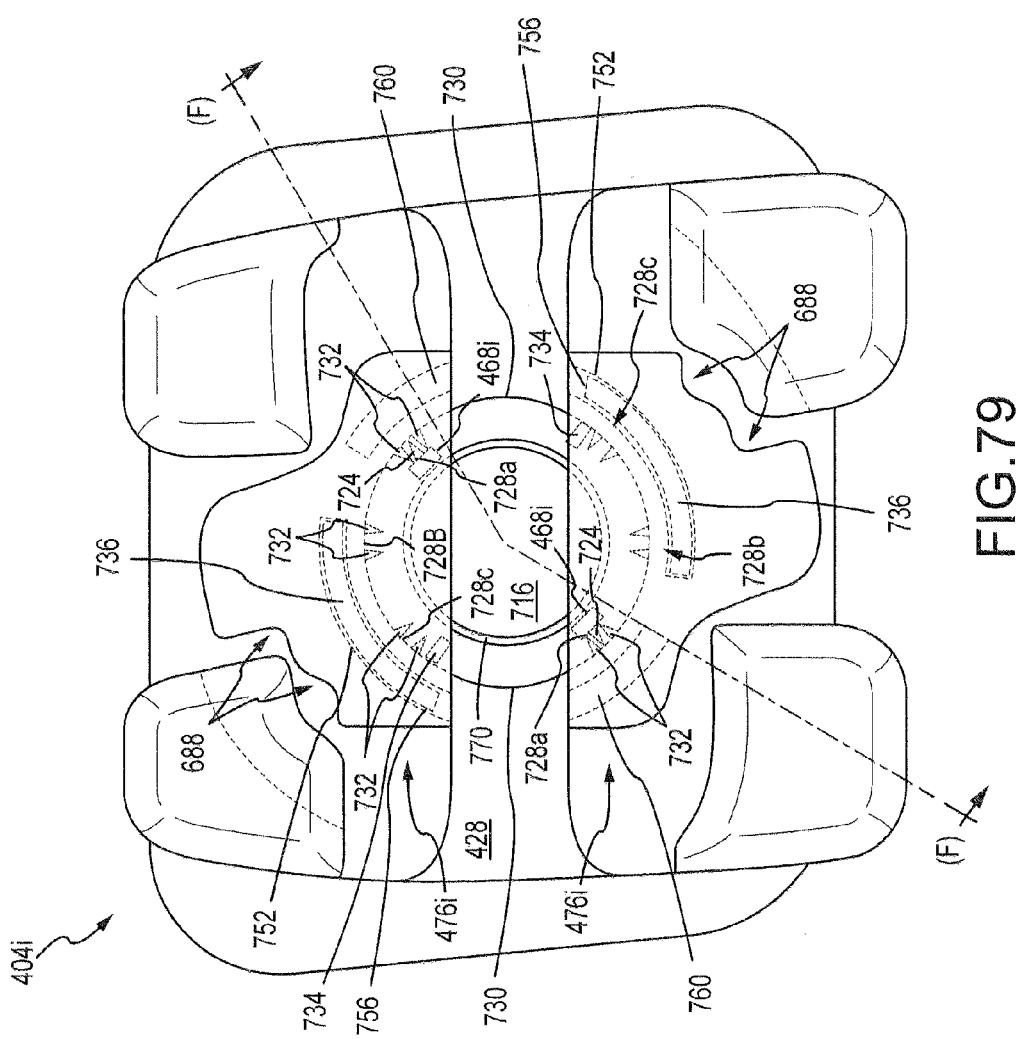
FIG. 79 is a plan view of the bracket 404i in the open configuration.

FIGS. 78 through 82 show additional embodiments of a self ligating bracket with a rotatable member. Referring to FIG. 78, this figure shows various embodiments of a bracket 404i, wherein the rotatable member 456i is shown separated from the remainder of the bracket to more clearly illustrate the features of the bracket. As can be seen, the slot coverable extensions 476i are irregularly shaped. The shape of the extensions 476i provides for orthodontic tool receiving attachment areas 688 for grasping the rotatable member 456i, e.g., with a pair of prongs or a tweezer-like tool (not shown) for simultaneously attaching to at least two opposing (non-adjacent) areas 688 and rotating the rotatable member. Additionally, the irregular shape of the extensions 476i has the advantages that when rotated into the passive closed configuration of FIG. 81 there is a relatively small surface area of these extensions constraining an archwire 508 to remain within the slot 504. Moreover, since the underside 692 of these extensions 476i that face the slot 428 (and the bracket front face 416i) can be convexly curved so that the thickness 696 (FIG. 78) of the extensions in the regions 704 becomes thinner, and since the regions 704 are the outer most portions of the extensions that cover the slot in the passive configuration of FIG. 81, the result of such convexity is that the slot covering portion of the extensions 476i is fluted. Accordingly, due to this fluting, it is less likely that an archwire 504 in the slot 428 will bind on contacting an edge of the extensions 476i extending over the slot 428. This may be particularly important for the bracket 404i in the passive configuration of FIG. 81 since the passive configuration is intended to allow slippage of the archwire 504 in the slot 428, and the archwire may (purposely or inadvertently during treatment) exert nontrivial orthodontic forces in contacting the extension underside 692.

Figure 82:
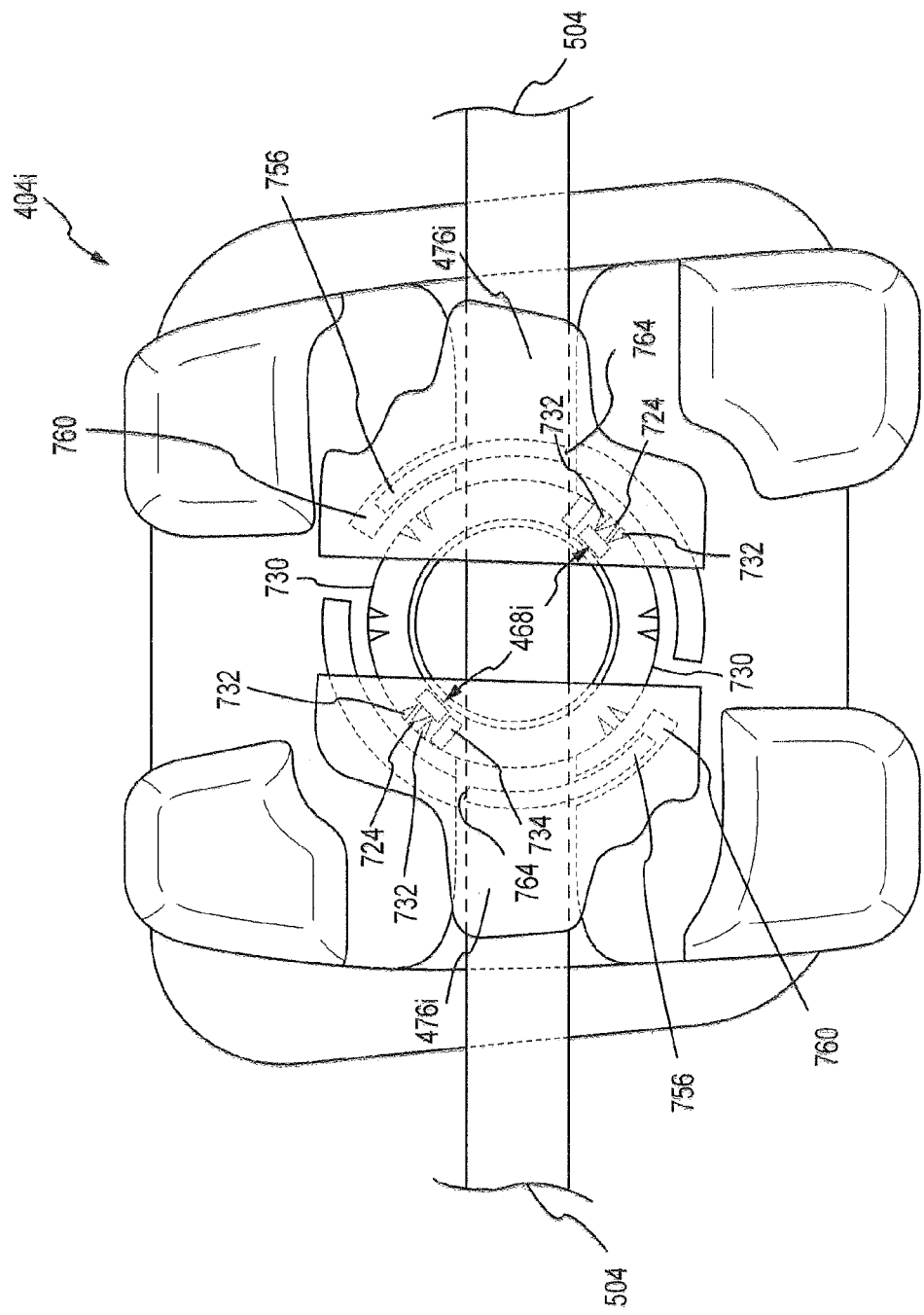
FIG. 82 is a plan view of the bracket 404i in the closed active configuration.
Figure 83:
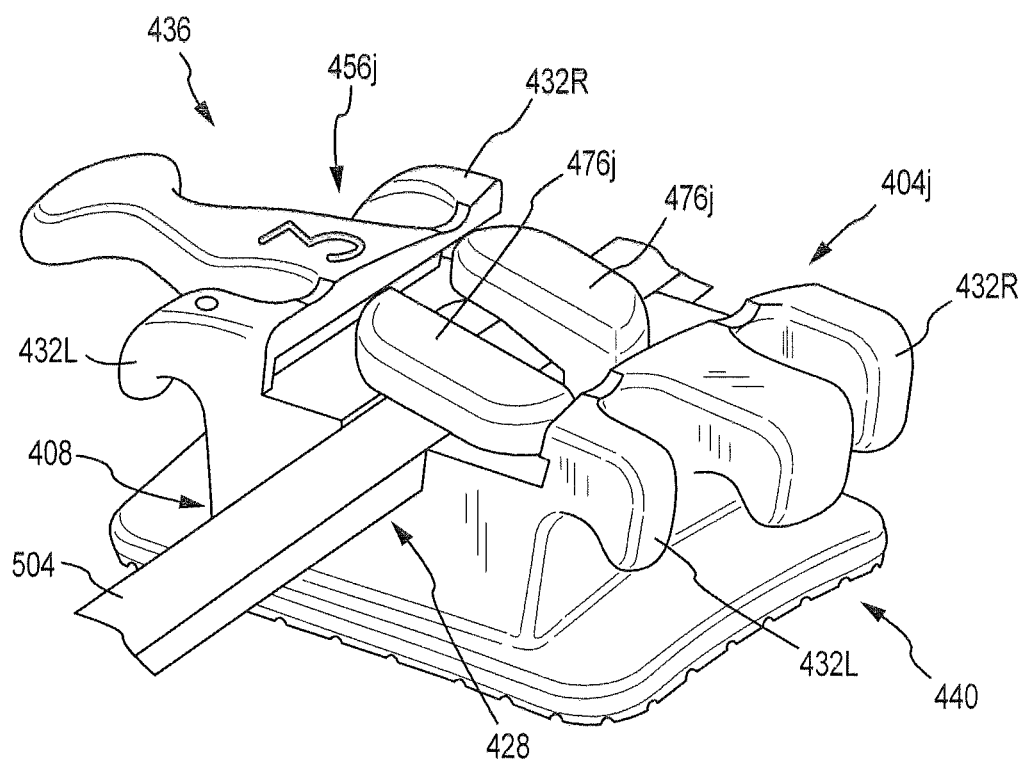
FIG. 83 shows an embodiment of a self ligating bracket 404j with a rotatable member 456j that is similar the embodiment of FIG. 73 or 77.

A further advantage of the irregular shape of the extensions 476i is that when the rotatable member 456i is rotated into the active closed position of FIG. 82, there is a substantial increase in the extent of the slot 428 covered by the extensions. In particular, there is approximately twice the amount of slot 428 opening covered by the extensions 468i in the active configuration, but such a change in the slot opening coverage may be in a range from, e.g., 20% more slot coverage in the active closed position (than in the passive closed position) to over 100% more slot coverage in the active closed position (than in the passive closed position), and more preferably in a range of at least 40% more slot coverage in the active closed position (than in the passive closed position) to over 100% more slot coverage in the active closed position (than in the passive closed position). Accordingly, since the active closed position is generally used during orthodontic treatment when it is desirable for the archwire 504 to remain substantially fixed relative to the slot (and/or move only small amounts in orthodontic terms), the increased length of the slot being covered by the extensions 476i assists in maintaining a desired alignment of the archwire relative to the bracket 404i. Moreover, even thought the archwire 504 may be firmly biased into contacting the slot floor 534 (FIG. 80) at one or more locations along the slot 428 length in the active configuration, the archwire may also angle away from the slot floor as the archwire extends to the ends of the slot, and the lengthened slot coverage in this active configuration may further constrain the archwire from changing shape or orientation thus providing better control over the alignment of the archwire relative to the bracket 404i.

Figure 80:
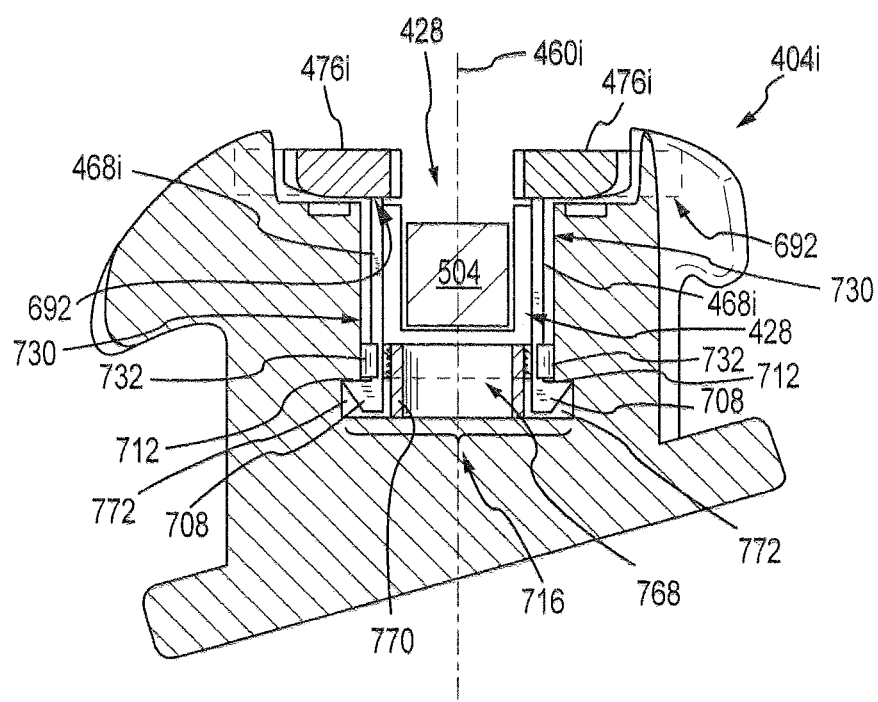
FIG. 80 is a cross sectional view of the bracket 404i produced by cutting through the bracket along two cutting planes associated with line segments identified by "F". In particular, the cutting planes cut the bracket perpendicularly to the drawing of FIG. 79.
Figure 81:
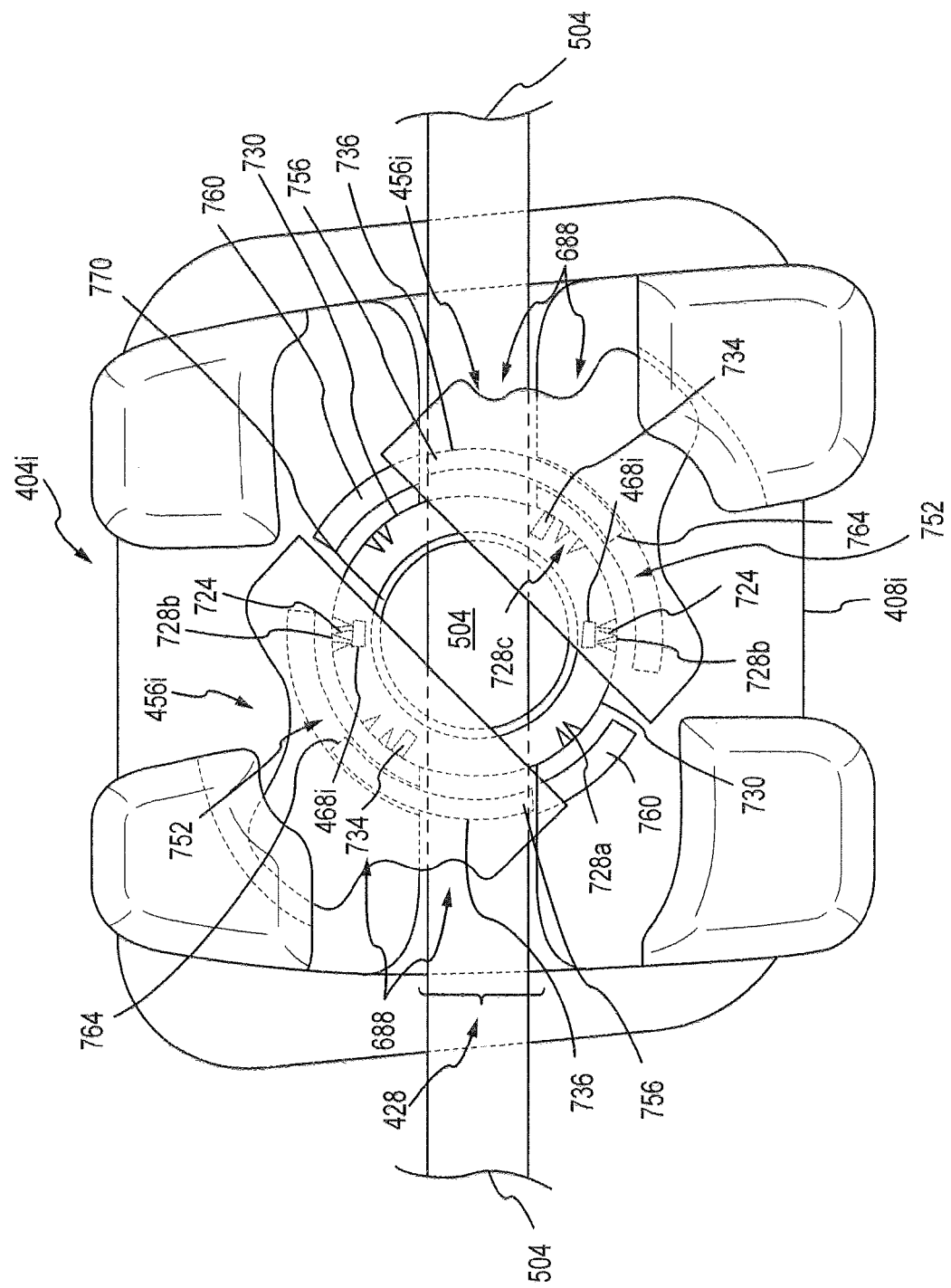
FIG. 81 is a plan view of the bracket 404i in the closed passive configuration.

Referring again to FIG. 78, the bracket body 408i includes a generally cylindrical recess 444i substantially in the center of the slot 428 for rotatably attaching the rotatable member 456i to the bracket body 408i. The interworking features and elements of the cylindrical recess 444i and rotatable member 456i are best described with reference to both FIGS. 78 and 80. Accordingly, it is noted that FIG. 80 is a cross section of bracket 408i according to the sectioning planes corresponding with the line segments identified by "F" in FIG. 79.

The rotatable member 456i includes columns 468i, one such column attached to the underside 692 of each of the extensions 476i. Each of the columns 468i includes a wedge 708 at its free end for interlocking with a ledge 712 (FIG. 80) of an expanded diameter base portion 716 (FIG. 80) of the recess 444i. Accordingly, when the rotatable member 456i is inserted into the bracket body 408i (as indicated by arrow 720, FIG. 78), the wedges 708 initially compress inwardly toward the central axis 460i (FIGS. 78 and 80), but then expand outwardly when the expanded diameter base portion 716 is encountered thereby securing the rotatable member 456i in the recess 444i.

Each of the columns 468i may also include a locking tab 724 (FIG. 78) for engaging (and entering into) notches 728a-c (FIGS. 79-82) defined by pairs of closely spaced ridges 732 distributed about the circumference wall 730 of the recess 444i. In particular, there is a pair of ridges 732 (and a notch 728a-c between the ridges of each pair) for securing the rotatable member 456i in each one of its open, passively closed, and actively closed positions. Accordingly, there are three pairs of ridges 732 for each of the two locking tabs 724 such that the locking tabs synchronously lock into a corresponding notch 728. In particular, the locking tabs 724 lock into the notches 728a for securing the rotatable member 456i in the open position (FIG. 79); the locking tabs lock into the notches 728b for securing the rotatable member in the passively closed position (FIG. 81); and the locking tabs lock into the notches 728c for securing the rotatable member in the actively closed position (FIG. 82). Note that there is a stop 734 attached to, e.g., the wall 730 for preventing each of the columns 468i from rotating into slot 428.

The rotatable member 456i also includes variable thickness archwire stabilizers 736 on the underside 692 of each of the extensions 476i. Each stabilizer 736 is arcuately shaped such that its inner lengthwise side 740 is uniformly radially offset from the central axis 460i, and the stabilizer's outer lengthwise side 742 is uniformly radially offset a larger amount from the central axis 460i. Moreover, for each stabilizer 736, as its arcuate length is traversed from first end 744 clockwise to its second end 748, the thickness of the stabilizer increases thereby extending progressively further in the direction of bracket body 408i and away from at least the immediately surrounding portion of the underside 692 surface. When the bracket 404i is assembled, and the rotatable member 456i is in the open position (FIG. 79), each stabilizer 736 substantially resides in a corresponding arcuate bay 752 which is deeper than the maximal thickness of the stabilizer. When the rotatable member 456i is rotated into the closed passive position (FIG. 81), each of the stabilizers 736 extends partially into the slot 428. However, since the portion of each stabilizer 736 extending into the slot 428 has a relatively thin thickness, the archwire 504 in the slot is not pressed against the slot floor 534 (FIG. 80) by the stabilizer. However, when the rotatable member 456i is rotated into the closed active position (FIG. 82), the thickest part of the each of the stabilizers 736 extends into the slot 428, and accordingly, the archwire 504 in the slot 428 is firmly pressed against the slot floor 534 by the stabilizer. Note that as the rotatable member 456i is rotated into the closed active position, the leading thin portion 756 (FIG. 82) of each stabilizer 736 is received into a corresponding bay 760.

In one embodiment, each of the stabilizers 736 may be shaped so that although its thickness increases along a clockwise traversal of its length from the leading portion 756 to near the trailing edge 764. However, just before trailing edge is reached, the thickness of the stabilizer rapidly (but smoothly) tapers off and merges with the surrounding underside 692 surface. Accordingly, rotatable member 456i will readily move in both the clockwise and counter clockwise directions, and the stabilizers 736 will not bind on entering or exiting their corresponding pair of bays 752 and 760.

The rotatable member 456i also includes a ring 768 (FIGS. 78 and 80) that connects to each of the columns 468i generally between just above their wedges 708. When the bracket 404i is fully assembled, the ring 768 assists in maintaining proper orientation of the columns 468i as these columns are angularly moved about the central axis 460i when the rotatable member 456i is rotated between the open, passively closed, and actively closed positions. In particular, when the bracket 404i is assembled, the ring 768 fits over an alignment cylinder 770 (FIGS. 78-82) attached to the base 716. Accordingly, when the rotatable member 456i is rotated about the central axis 460i, the ring 768 rotates about the exterior surface of the alignment cylinder 770, and assists in preventing the wedges 708 from binding in the annular passageway 772 (FIG. 80) between the annular ledge 712 and the base 716. In one embodiment, the ring 768 may be very flexible thereby allowing the columns 468i to resiliently move radially relative to the central axis 460i and thereby accommodate corresponding radial movement of the locking tabs 724 in and out of the notches 728a-c.

In one embodiment, the rotatable member 456i may also include a cap (not shown) that substantially encloses the recess 444i at or about the level of the slot floor 534. Such a cap would typically be parallel the underside 692, attached to the columns 468i, and generally circular for fitting in the circular opening just above, e.g., the ridges 732 (FIG. 78).

In other embodiments of the rotatable member 456i, this member may be configured in a manner similar to the extension of 456, FIG. 44, in that the cylindrical portion 464 and/or the columns 468, respectively, may replace the ring 768 and/or the columns 468i. The rotatable member 456i may also be configured similarly to rotatable member 456g (FIG. 73) or 476h (FIGS. 76, 77), wherein the alignment cylinder 770 may be removed from the recess 444i, and each pair of ridges 732 being replaced by at least one notch 666.

Note that although the alignment cylinder 770 is shown as hollow in, e.g., FIG. 78, embodiments of the alignment cylinder may be solid as well. Moreover, a solid alignment cylinder 770 may have advantages in enhancing the strength of the bracket 404i, providing easier manufacturability, and providing fewer areas where bacteria, calculus and the like may build up.

In one embodiment of the rotatable member 456i, the ring 768 may cooperate with the stabilizers 736 to fix the archwire 504 in the slot 428. In particular, the ring 768 may be a cylinder and have threads 776 on its inner cylindrical surface wherein such threads mate with threads 780 on the exterior surface of the alignment cylinder 770. Such mating threads will, within a 90° counter clockwise rotation, mesh together to tighten the extensions 476i onto the archwire 504, and subsequently (if desired) loosen the extension 476i from actively closing on the archwire when the mated threads are (at partially) unmeshed by a 90° clockwise rotation. Note that although the embodiments of FIGS. 79-82 show such mating threads 776 and 780, such threads may be only optionally provided in embodiments of the bracket 404i, and accordingly, the surfaces described as being threaded hereinabove may instead be smooth.

Note that, in one embodiment, the locking tabs 724 may be provided on columns or posts separate from the columns 468i.

It is noteworthy that the bracket 404i includes the following distinctions in comparison to at least the bracket embodiments of FIGS. 41-66 described above:
  (i) No portion of the bracket 404i fits into or is adjacent to the floor (e.g., 716) of the recess 444i as comparable elements do in the bracket embodiments of FIGS. 41-66.
  (ii) The extensions 476i are not "C" shaped as disclosed in the description of the bracket embodiments of FIGS. 41-66.
  (iii) The extensions 476i cover the slot 428 with different coverage amounts of coverage depending on whether the bracket is in a closed passive configuration or a closed active configuration. In particular, a lesser extent of slot coverage is provided for the closed passive configuration so that the archwire is allowed more movement in the slot, and a greater extent of slot coverage is provided for the closed active configuration.
  (iv) The underside (692) of the extensions 476i are tapered or fluted at their boundaries (particularly, the boundaries that can connect the archwire and potentially bind thereon if not tapered or fluted).
  (v) The mechanism(s) for securing the rotatable member 456i in the positions: open, passively closed, and actively closed are internal to the recess 444i, whereas in the embodiments of FIGS. 41-66, such securing features reside in interactions between the front surface 416 and the facing side of the extensions where these securing features can be more easily disengaged.
  (vi) The extensions 476i provide features for attaching an orthodontic tool thereto for rotating the rotatable member 456i. No such tool attachment features are available in the embodiments of FIGS. 41-66.

The description hereinbelow describes the encoding of information on the tooth facing side of an orthodontic bracket base as well as associated techniques for providing enhanced adhesion of the bracket to its tooth. It is within the scope of the present disclosure to use the techniques disclosed hereinbelow with the various embodiments of self ligating brackets 404, and 404a through 404i described hereinabove.

One embodiment of the body 8 of an edgewise bracket 10 of the present disclosure is illustrated in FIGS. 1A-C and 2A-D, with various modifications, modalities and an exemplary auxiliary reflected by FIGS. 3A-C, 4A-E, 5A-C, 6A-C and 7A-B, and with various base structures and as illustrated in FIGS. 8-18 and 20-59. Corresponding features are referenced by common reference numerals.

The edgewise bracket 10 comprises two integral, opposing T-shaped tie wings 12 and 14 having a common base portion and base surface 16, and defining an archwire slot 18 therebetween. By way of example only, a flange 32 may be adjoined to the bracket 10 for subsequent attachment to a band. Alternatively, the bracket may be adjoined to a bonding pad (not shown).

Two sets of opposing ligating support means 20 and 22, are provided, each set comprising a gingivally disposed notch and occlusally disposed notch on the gingival and occlusal edges of tie wings 12, 14, respectively. Each ligating support means has a sloped portion 24 and top land portion 26. The sloped portions 24 have concave, curvilinear surfaces.

Each of the T-shaped tie wings 12, 14 comprises a cantilevered central leg portion 28 centered upon the gingival-occlusal center axis (lying within plane AA) of the bracket 10 and cantilevered mesial/distal wing tip portions 30, with the above-noted top land portions 26 integral-therebetween. The gingival/occlusal extremes of the center leg 28 and mesial/distal wing tip portions 30 of the tie wings 12, 14 define, from the labial aspect, an elliptical configuration E. In this regard, cantilevered wing tip portions 30 extend a sufficient distance d outward from the outer sidewalls 34, 36 of the tie wings 12, 14, respectively, to retain a ligating device in an arcuate seat 38 formed under the cantilevered tie wing tip portions 30 and center legs 28. Relatedly, the cantilevered center leg 28 of each T-shaped tie wing 12, 14, extends a distance f beyond the outer gingival/occlusal extreme of the ligating support means 20 adjacent thereto, such distance f being at least approximately as great as the distance d.

Figure 1A:
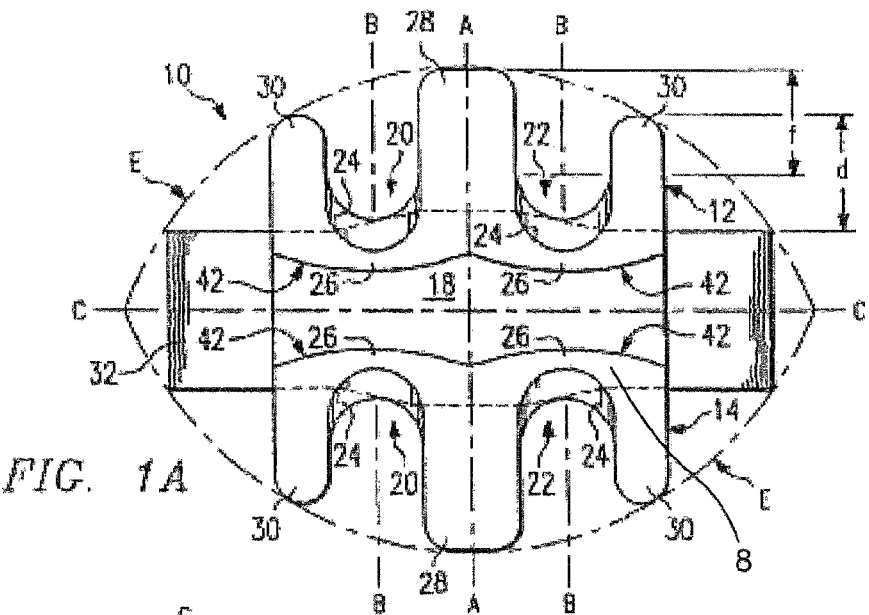
FIGS. 1A-C illustrate labial, side and end views of a first embodiment of an orthodontic bracket.
Figure 1C:
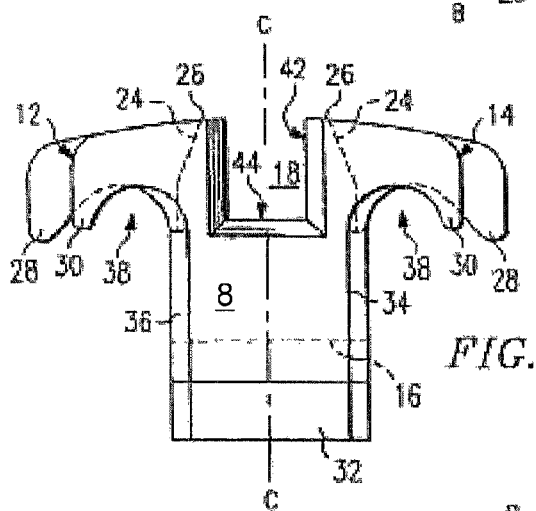
Figure 1B:
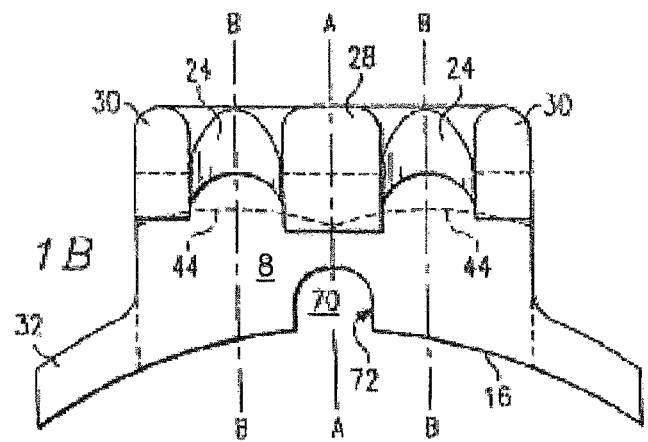

The sidewalls defining the archwire slot 18 comprise two sets of opposing convex portions 42 to reduce frictional engagement with an archwire. Similarly, the floor of archwire slot 18 is provided with two convex portions 44 extending transversely across the archwire slot 18 to reduce frictional engagement with an archwire. As illustrated in FIGS. 1A-C, the ligating support means 20, convex slot sidewall portions 42, and convex slot floor portion 44 disposed on the same side of the gingival-occlusal center plane AA may have a common center axis (lying within plane BB). As such, frictional engagement between an archwire and the slot walls and base, and between an archwire and ligating device supported on ligating support means 20 occurs in a limited region about plane BB.

An optional auxiliary slot 70 may be provided to receive a complimentary auxiliary device, such as the exemplary auxiliary 74 illustrated in FIGS. 7A and 7B. The inner sidewalls of auxiliary slot 70 and interfacing shaft portion 76 of the exemplary auxiliary 74 are preferably configured to restrict rotational movement therebetween. As illustrated, a complimentary square-angled configuration may be employed. Additionally, the auxiliary 74 preferably comprises an extending portion 78 having an outer configuration which will not fit into auxiliary slot 70, thereby facilitating placement and removal.

Figure 2A:
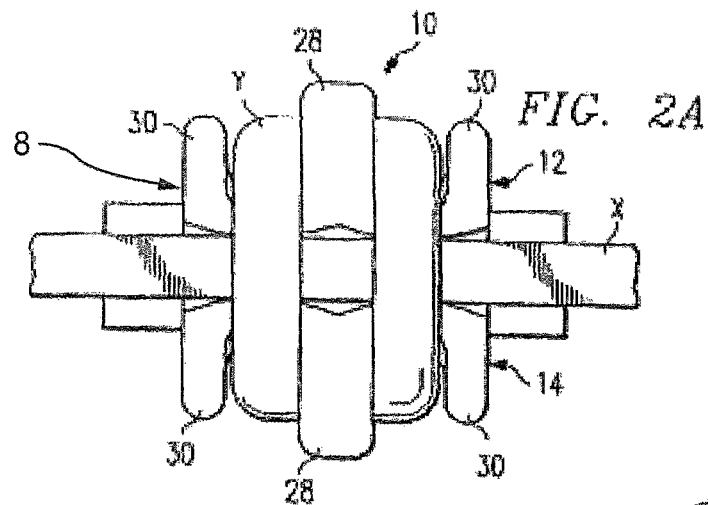
FIGS. 2A and 2B, illustrate labial and end views of the first embodiment of FIGS. 1A-C when ligating support means are employed to support an elastomeric ligature.
Figure 2B:
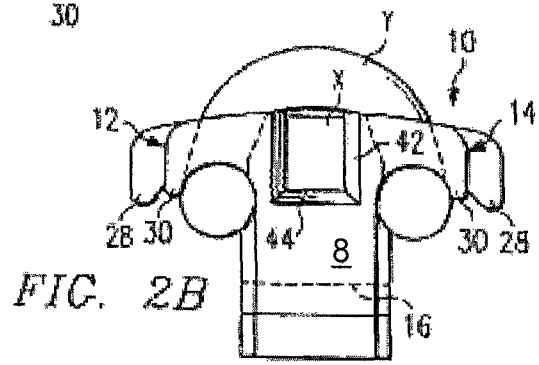
Figure 2C:
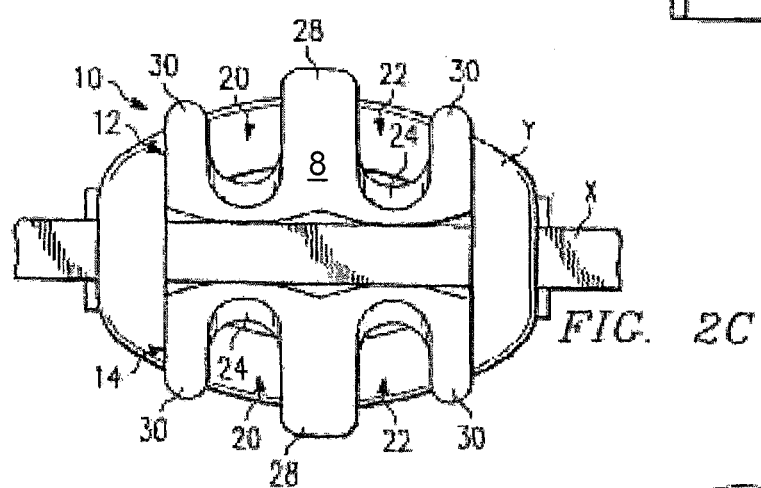
FIGS. 2C and 2D illustrate labial and end views of the first embodiment of FIGS. 1A-C when ligating support means are not employed to support an elastomeric ligature, respectively.
Figure 2D:
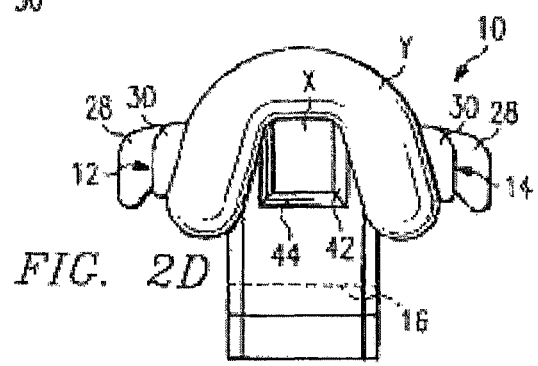

FIGS. 2A-B illustrate the interface between an archwire X and elastomeric ligating device Y when both sets of the ligating support means 20 of the embodiment illustrated in FIGS. 1A-C are utilized. FIGS. 2C-D illustrate the interface between an archwire X and elastomeric ligating device Y when neither of the ligating support means 20 of such embodiment are utilized. As will be appreciated by those in the art, there are different treatment situations where each of these modalities may be desired. Additionally, the provision of a set of ligating support means 20 on each of the mesial and distal sides of the bracket 10 allows a practitioner to utilize one set but not the other, as may be desirable.

Figure 3A:
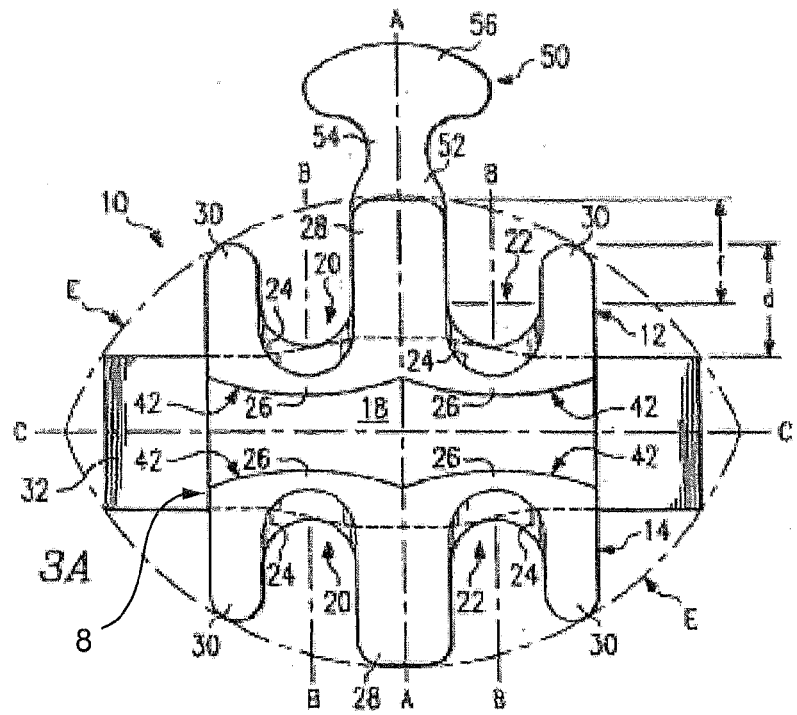
FIGS. 3A-C illustrate labial, side and end views of a modified version of said first embodiment having an integral T-shaped hook and twin auxiliary slots.
Figure 3C:
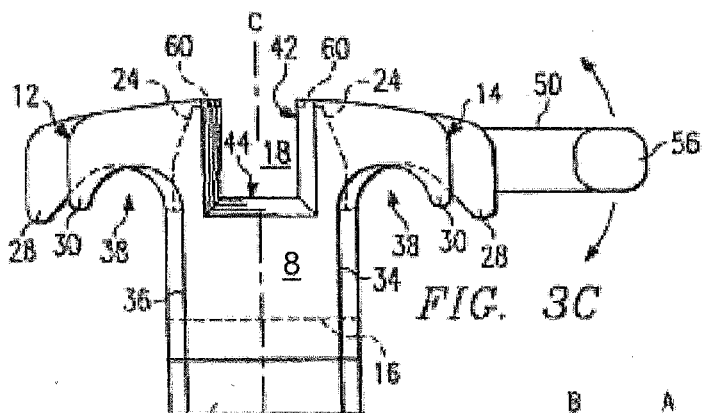
Figure 3B:
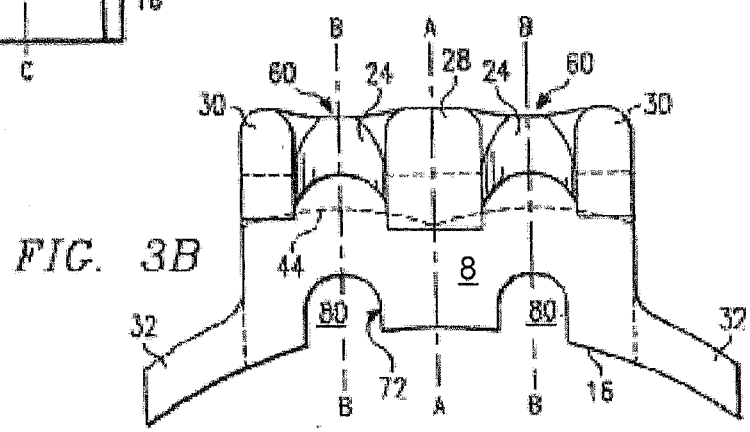

In FIGS. 3A-C an integral T-shaped hook 50 is provided as an extension to the center leg 28 of one of the T-shaped tie wings 12. The T-shaped hook 50 preferably comprises flat lingual and labial surfaces (see FIG. 3C), and is preferably malleable to allow for pivotal movement relative to center leg 20. The T-shaped hook 50 preferably comprises a tapered portion 52, arcuate neck portion 54 and head portion 56, whereby retention of a traction device in neck portion 54 is enhanced.

Twin auxiliary slots 80 may be optionally provided for receipt of an auxiliary device, such as the exemplary auxiliary 74 shown in FIGS. 7A-B. The twin auxiliary slots 80 are beneficially disposed under the convex slot floor portions 44. The configuration of slots 80 and exemplary auxiliary 74 may be as described above to restrict rotational movement therebetween and facilitate placement/removal.

FIGS. 3A-C also illustrate optional saddles 60 which can be provided in the support landing portions 26 for receiving a ligating device. It is believed that such saddles 60 may be beneficial in certain early treatment situations for purposes of retaining an undersized archwire in the desired position for rotational purposes.

In FIGS. 4A-E, the outer sidewall 34 of tie wing 12 and outer sidewall 36 of tie wing 14 define a trapezoid therebetween. Specifically outer side wall 34 is angled relative to the longitudinal center plane CC of the archwire slot 18, and the outer tie wing sidewall 36 is disposed in parallel relation to the center plane CC of the archwire slot 18. By virtue of this arrangement, the outer sidewall 34 may be, for example, advantageously disposed gingivally on partially erupted upper bicuspids. Further, bracket systems employed by this configuration will generally reduce bracket/tooth contact between upper and lower arches.

Figure 4D:
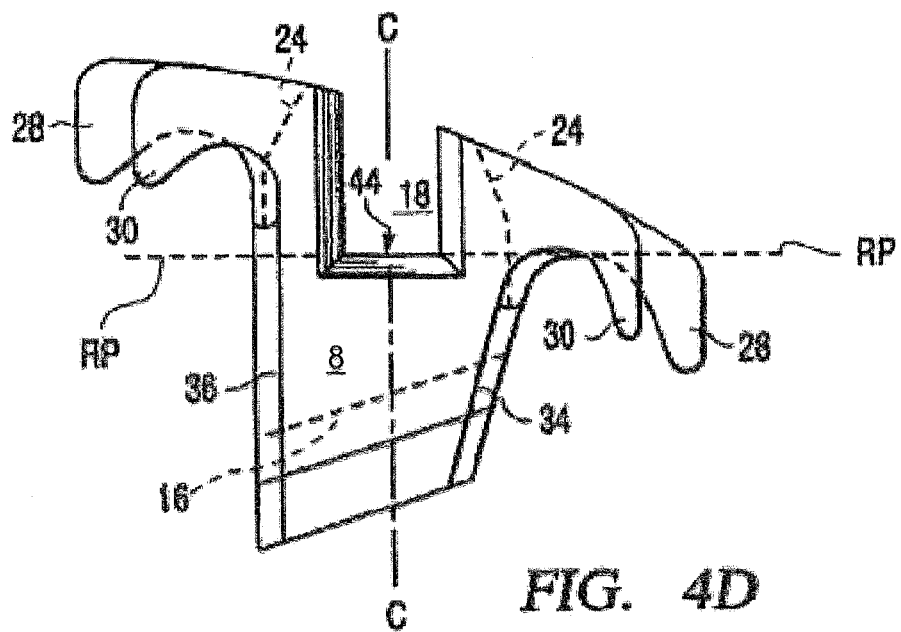
Figure 4E:
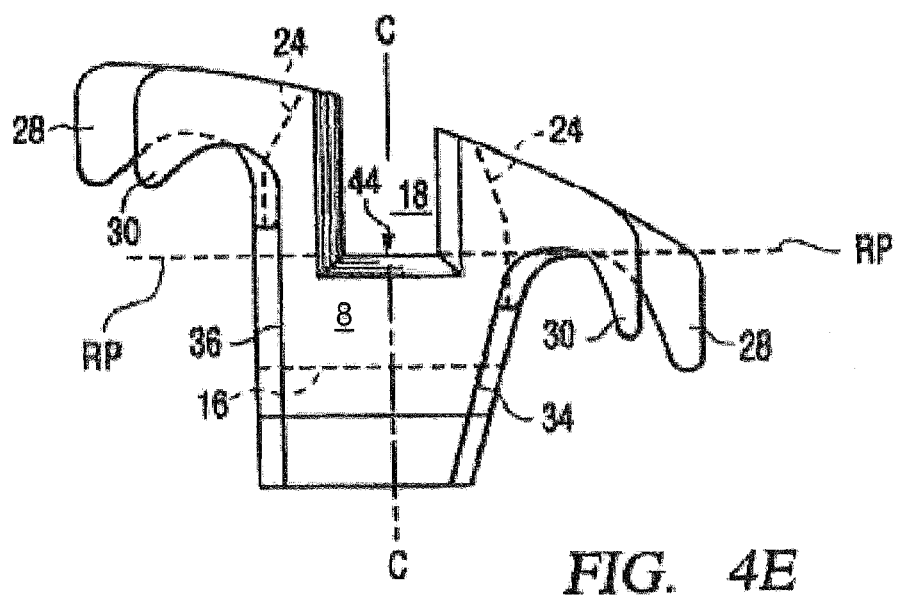

Referring in more detail to FIGS. 4C-E, the trapezoidal configuration of the bracket 10 is illustrated with three alternate configurations for the base portion 16. Generally, the configuration of the base portion 16, namely its occlusal/gingival extent, may be defined in relation to the reference plane RP. As can be seen in FIGS. 4B-E, the reference plane RP coincides with that portion of the bottom or floor of the archwire slot 18 which engages the archwire when positioned therein (e.g., a plane which is tangent to the two convex slot floor portions 44.

The configurations of base portion 16 in FIGS. 4C-E allow a practitioner to provide positive, negative, and no torque on a tooth of a particular orientation. Initially, with the tie wing 34 being gingivally positioned in a maxillary application, the base portion 16 of FIG. 4C would be used to provide for "positive torque" on a tooth, the base portion 16 of FIG. 4D would be used to provide for "negative torque" on a tooth, and the base portion 16 of FIG. 4E would be used to provide for "no torque" on a tooth. More particularly, in the case of the bracket 10 of FIG. 4C the base portion 16 would thereby extend from its gingival edge to its occlusal edge generally toward the reference plane RP in order to properly orient the archwire slot 18 on the orthodontic patient. Moreover, in the case of the bracket 10 of FIG. 4D the base portion 16 would thereby extend from its gingival edge to its occlusal edge generally away from the reference plane RP in order to properly orient the archwire slot 18 on the orthodontic patient. Furthermore, in the case of the bracket 10 of FIG. 4E the base portion 16 would thereby extend from its gingival edge to its occlusal edge generally parallel with the reference plane RP in order to properly orient the archwire slot 18 on the orthodontic patient.

In the event that the tie wing 36 is gingivally positioned in a mandibular application, the base portion 16 of FIG. 4C would provide for "negative torque" on the tooth, the base portion 16 of FIG. 4D would provide for "positive torque" on the tooth, and the base portion 16 of FIG. 4E would provide "no torque" on the tooth.

The modified embodiment illustrated in FIGS. 4A-C is shown with additional features in FIGS. 5A-C and 6A-C, although the bracket 10 of FIGS. 4D-E could be similarly modified as well. In FIGS. 5A-C, a central auxiliary slot 70 is provided. However, such an auxiliary slot 70 need not be centrally located along the mesial-distal extent of the bracket. Instead, the auxiliary slot 70 more to the mesial side of the bracket, or more to the distal side of the bracket.

FIGS. 6A-C illustrate the inclusion of twin auxiliary slots 80 for receiving of auxiliary devices. The twin vertical slots 80 are disposed so that each passes under one of the convex slot floor portions 44.

In the version shown in FIGS. 6A-C, it should also be appreciated that the gingival-occlusal center axis of the bracket (lying within plane AA) can be disposed at an acute angle relative to center axis of archwire slot 18 (lying within plane CC). More particularly, center legs 28 may be centered upon the gingival-occlusal center axis and may be provided with distal/mesial surfaces 84 which are parallel to the gingival-occlusal center axis thereby facilitating placement of the bracket. In this modified version, it should be recognized that while the center plane BB of the ligating support means 20 is also disposed parallel to the gingival-occlusal center axis, the apices of the convex slot sidewall portions 42 and convex slot floor portion on each of mesial and distal sides lie in a plane which is perpendicular to the archwire slot center plane CC. Relatedly, it should be appreciated that, when a T-shaped hook is utilized (such as the T-shaped hook 50 illustrated in FIGS. 3A-C above), the center axis thereof will be disposed perpendicularly to the center axis of the archwire slot 18 and at an angle relative to the gingival-occlusal center axis of the bracket 10.

Figure 8:
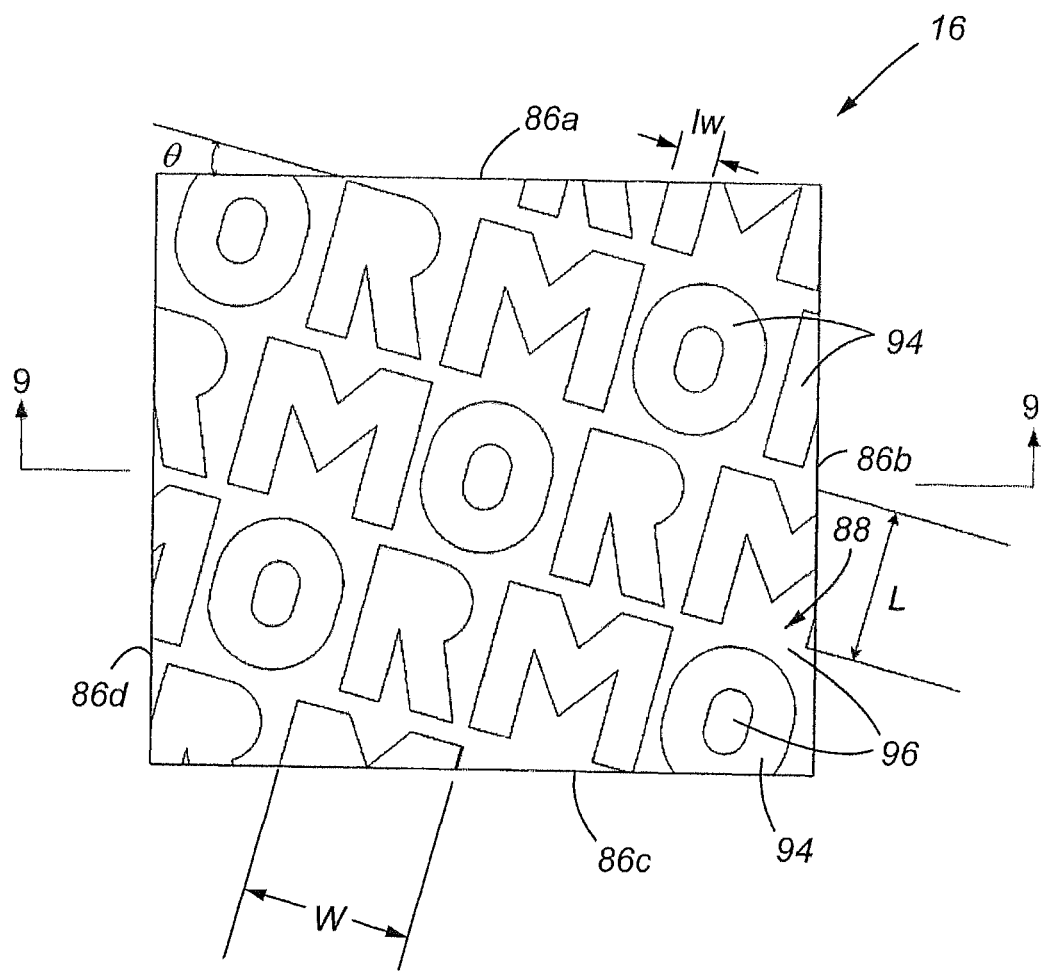
FIG. 8 is a rear view of the base of the orthodontic appliance, e.g., as shown in FIG. 4B without the flanges, and including a character base pattern embedded into the base 16 of the bracket.
Figure 9A:
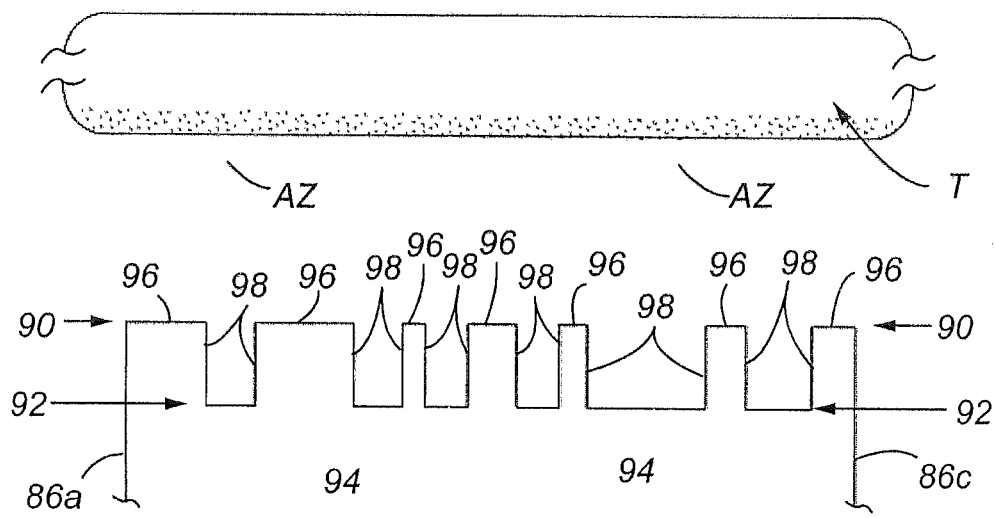
FIG. 9A-B are cross-sections taken along line 9-9 of FIG. 8.
Figure 9B:
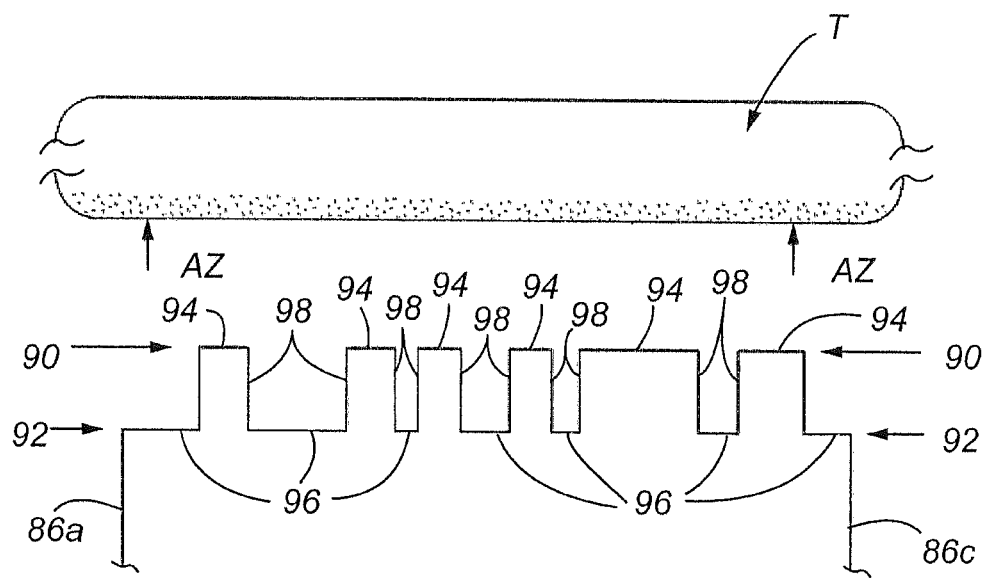

Referring now to FIG. 8, another aspect of the present disclosure is shown. FIG. 8 depicts an enlarged rear elevation view of the rear surface or base 16 of an orthodontic appliance, e.g., the bracket 10, as shown in FIG. 4B, but without flanges 32. Base 16 includes gingival edge 86a, distal edge 86b, occlusal edge 86c, and mesial edge 86d. Within the interior of edges 86a, 86b, 86c, and 86d is interior region 88. As depicted in FIGS. 9A and 9B, interior region 88 includes at least one projected surface 90 and at least one recessed surface 92. The projected surface 90 of the interior region 88 is a surface that is both substantially parallel to the tooth's surface and closest to the tooth's surface upon attachment of the orthodontic appliance, e.g., the bracket 10 to the tooth. The recessed surface 92 is a surface of the interior region 88 that is also substantially parallel to the tooth's surface, but is further away from the tooth's surface than the projected surface 90 upon attachment of the orthodontic appliance, e.g., the bracket 10 to the tooth. The recessed surface 92 is preferably recessed between about 0.009 to 0.012 inches relative to the projected surface 90, and more preferably, the recessed surface is recessed about 0.010 inches relative to the projected surface 90.

Characters 94 (e.g., FIG. 8) and intermediate space 96 extend substantially continuously within interior region 88, between edges 86a, 86b, 86c, and 86d. The pattern of characters 94 may be repeating, such as the letters "RMO" ® shown in FIG. 8, or they may be a non-repeating series of characters 94. Alternately, the characters may be a set of information regarding the orthodontic appliance, such as:

(i) its intended installation location such as characters representing tooth location, e.g., the characters "CENT" for identifying the installation location as a central tooth, "BIC" for identifying the installation location as a cuspid tooth, "MOL" for identifying the installation location as a molar; alternatively/optionally, such tooth locations may be identified by tooth number such as the number "8" identifies the maxillary right central tooth; alternatively/optionally, such tooth locations may be identified by Palmer Location, e.g., the symbols identify the maxillary left cuspid, (ii) its manufacturer,
(iii) its date of manufacturer,
(iv) its model number,
(v) its location of manufacture,
(vi) instructions or suggestions regarding use of the orthodontic appliance,
(vii) a patent number for the orthodontic appliance,
(viii) a logo, a trademark for the orthodontic appliance,
(ix) a pattern that may be optically scanned for obtaining information on the orthodontic appliance (e.g., any of the informational items (i) through (viii) hereinabove), etc.

Figure 21:
FIG. 21 shows the base 16 of an orthodontic application having a body 8, wherein information is encoded into the base by, e.g., molding, and in particular, providing the characters 94 as raised or projected portions of the base 16.
Figure 22:
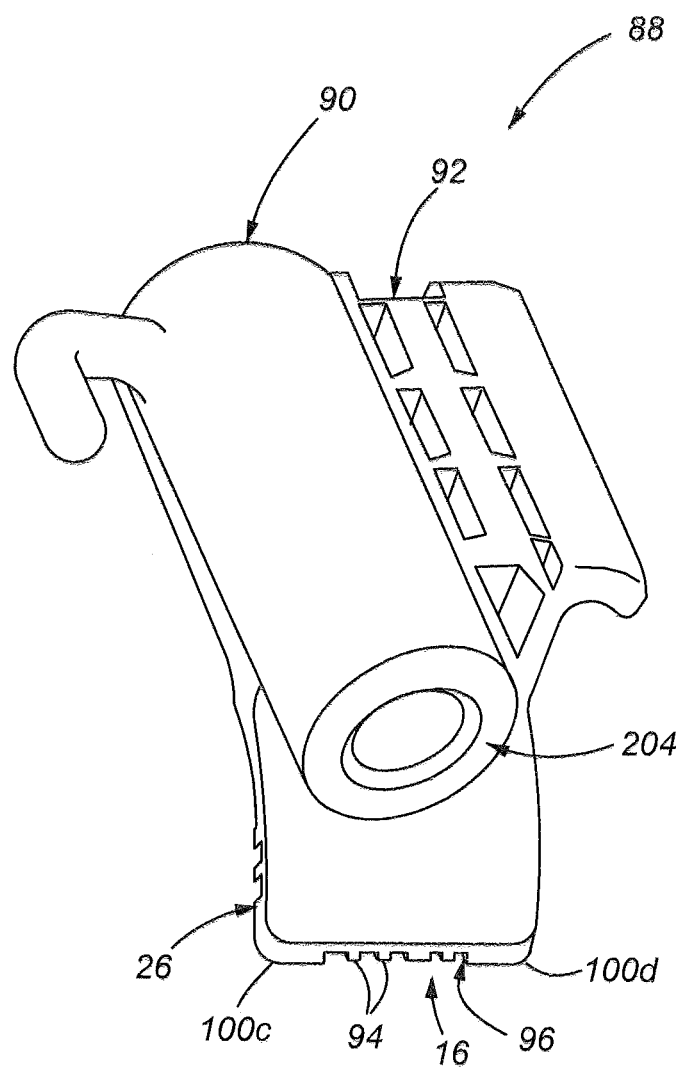
FIGS. 22 through 27 show various orthodontic appliances with bases 16 having encoded information embedded or formed in the bases, wherein the characters 94 are on the projected surface(s) 90 (e.g., as shown in FIGS. 9A and 9B), and the intermediary space 96 between the characters is provided on the recessed surface(s) 92 (e.g., as shown in FIGS. 9A and 9B).
Figure 23:
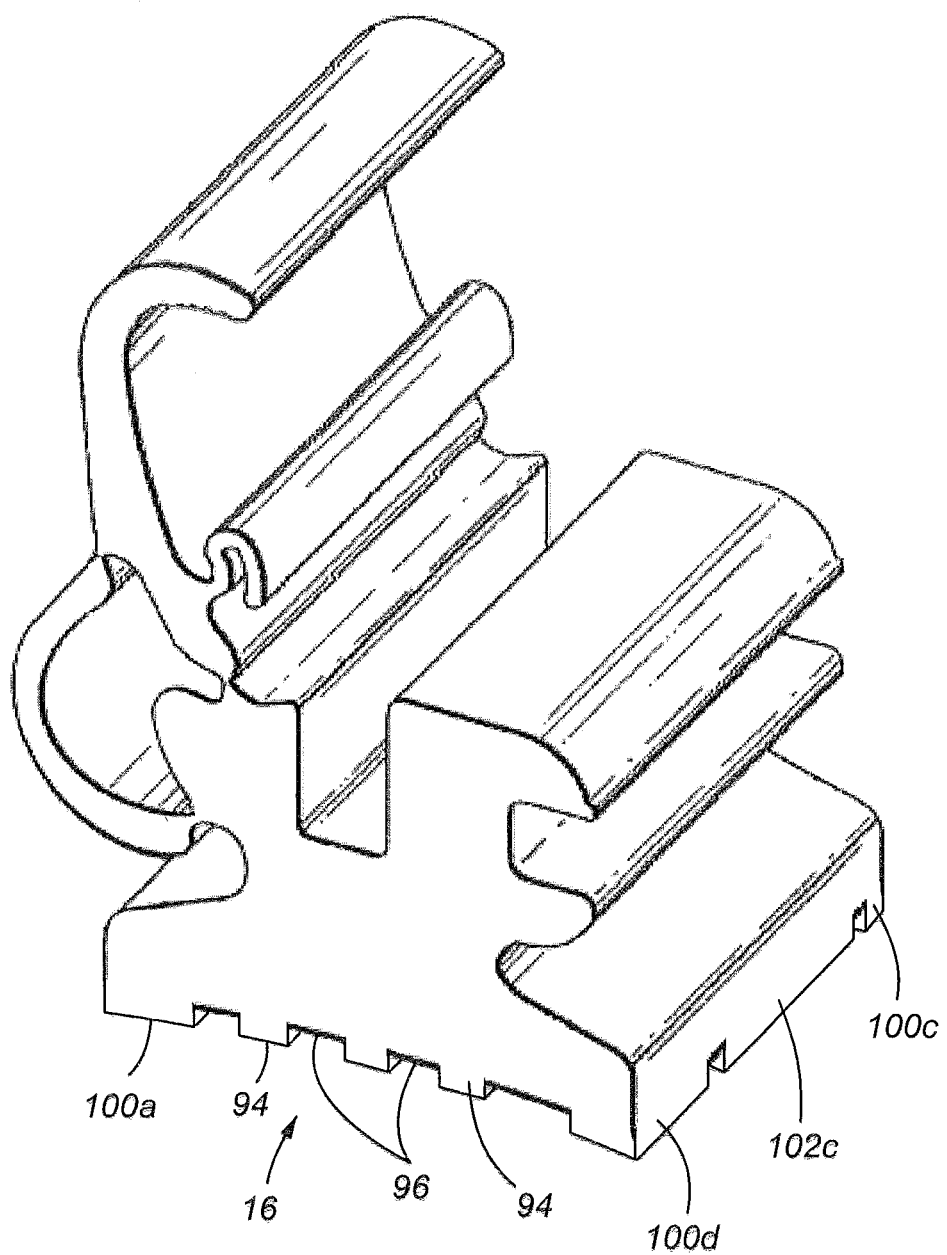
Figure 24:
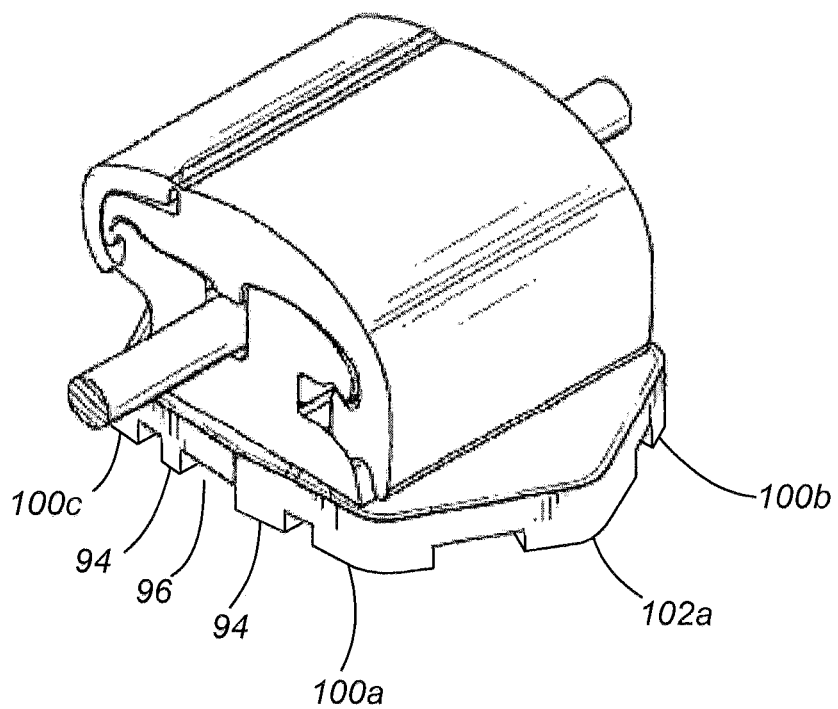
Figure 25:
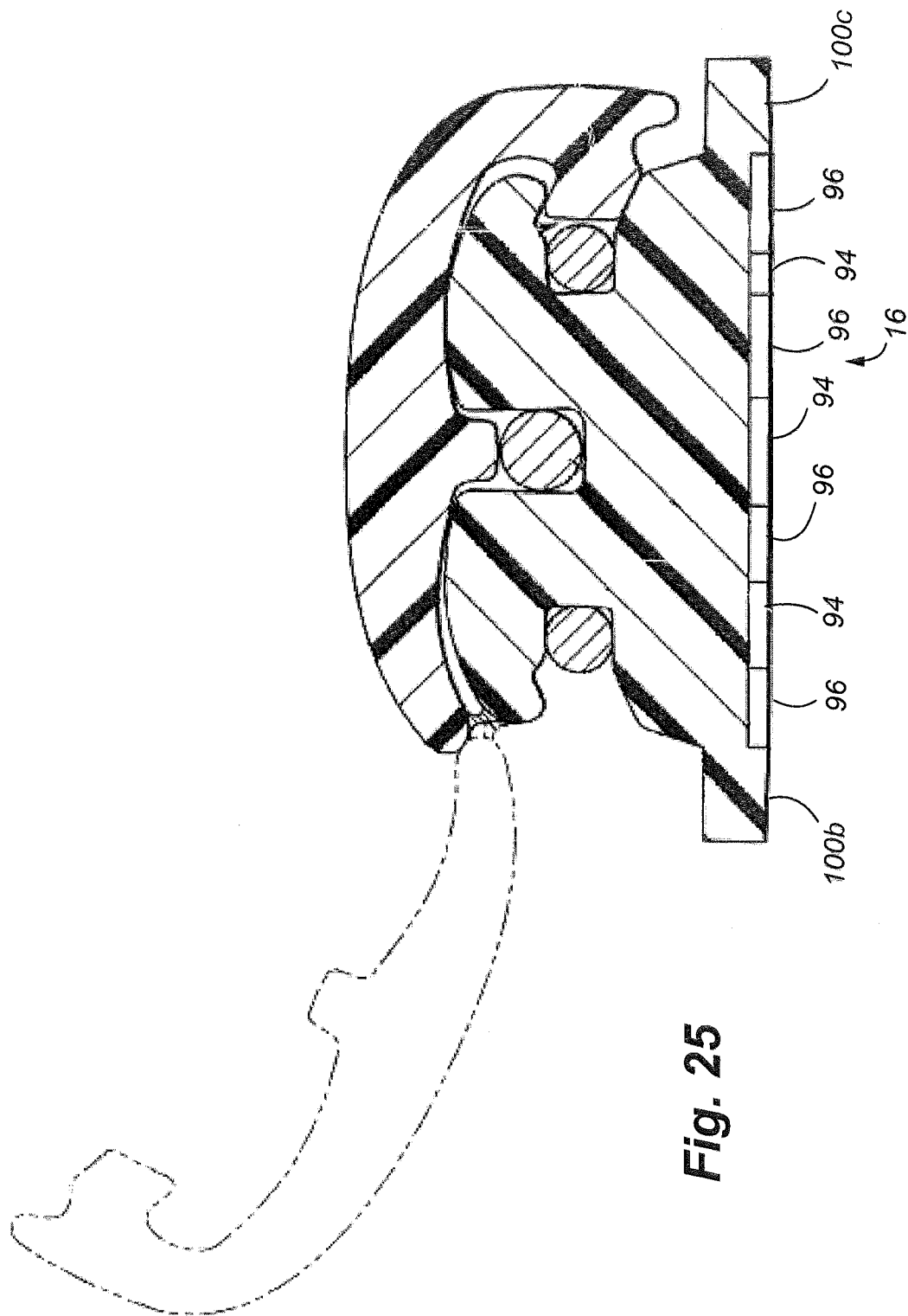
Figure 26:
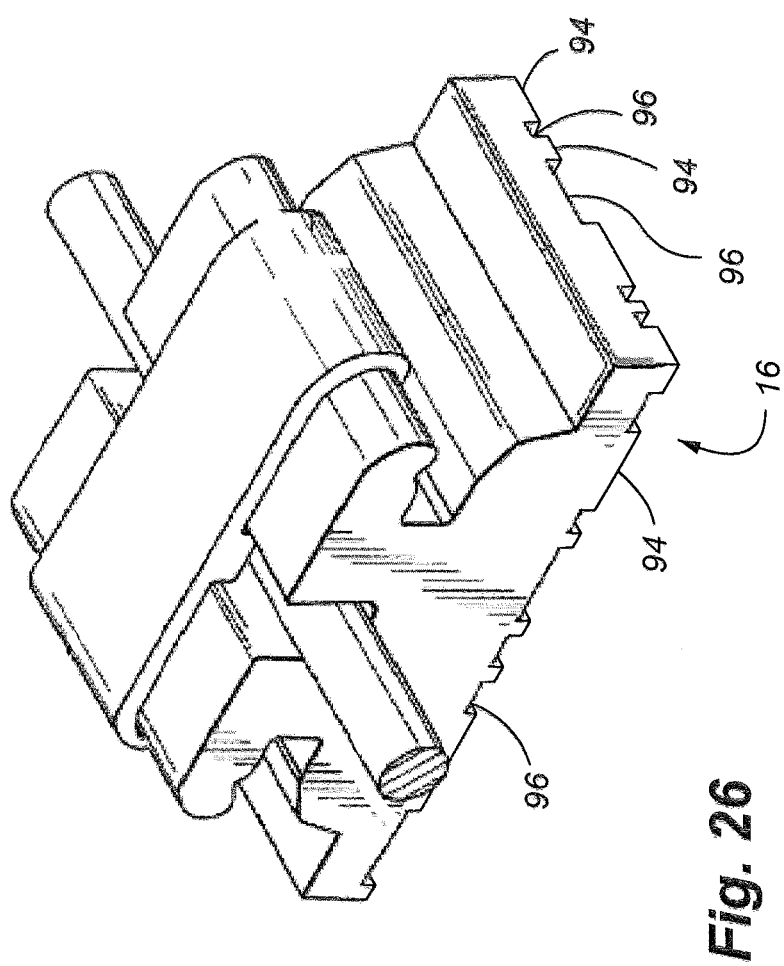
Figure 27:
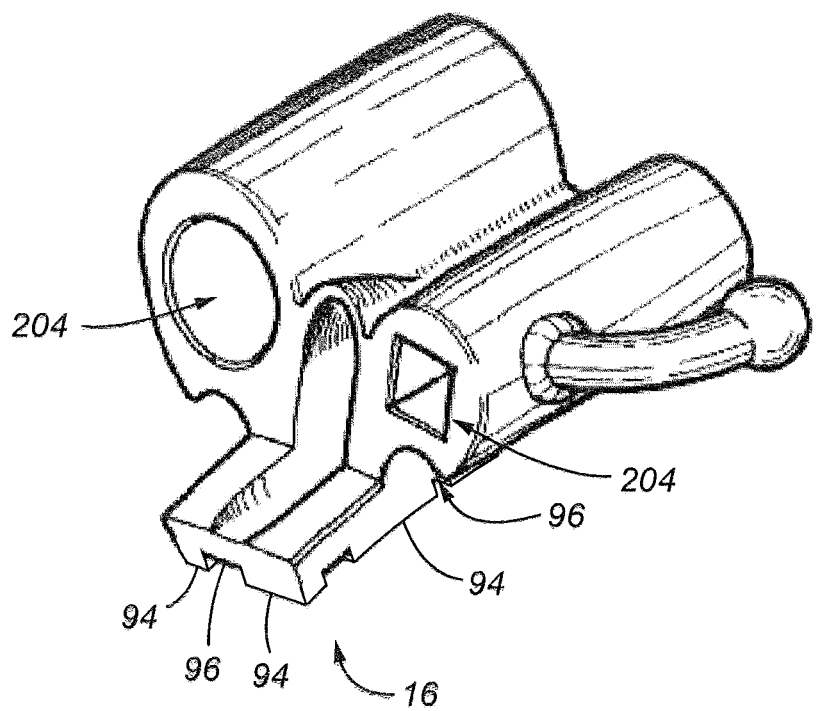

An example, of such a set of information is illustrated in FIG. 21, wherein the base 16 of the orthodontic appliance shown in this figure includes a series of projected characters 94 providing the following information encodings (from left to right and top to bottom):

the characters "RMO" identify the supplier of the orthodontic appliance as RMO, Inc.,
the "X" is a separation character,
the characters "TS54" identify model of an orthodontic tube,
the characters "072407" identify the date of manufacture,
the characters "CUS" identify the location of manufacture as Colorado in the U.S.,
the characters "B46" identify the batch of material(s) from which the orthodontic appliance was created, and
the "X" is a separation character, and
the characters "IV6" identifies the version of the documentation that is to be supplied to an orthodontist with the appliance.

As one of skill in the art will appreciate, the provision of such information on the base of an orthodontic appliance performs a useful function with respect to the use of the device, and tracing the source and time of manufacturer in the event of a defective appliance, and/or a recall may be necessary.

Note that the separation character (e.g., "X" hereinabove) may be optionally used or not used depending the amount of information to be embedded in the base 16. If, e.g., only the first row of information in FIG. 21 were to be embedded in a base 16 of an orthodontic appliance, then the separation character may be used to fill up any additional space remaining on the base 16. That is, an important aspect of such embedding of information is to not only provide information on the appliance, but also substantially increase the base area (such area including the areas of the walls 98 (e.g., FIG. 15A described hereinbelow) separating the projected portions of the base 16 from the recessed portions of the base) to which an adhesive can adhere. Accordingly, it can be important that such characters be chosen so that the base area increases, e.g., at least 30% and preferably 40% or more over a substantially two dimensional, e.g., flat or convex, base 16. Thus, a character such as "X" provides more wall 98 surface area for adhesive adherence than, e.g., the hyphen symbol "-", and accordingly "X" is generally preferable.

Figure 28:
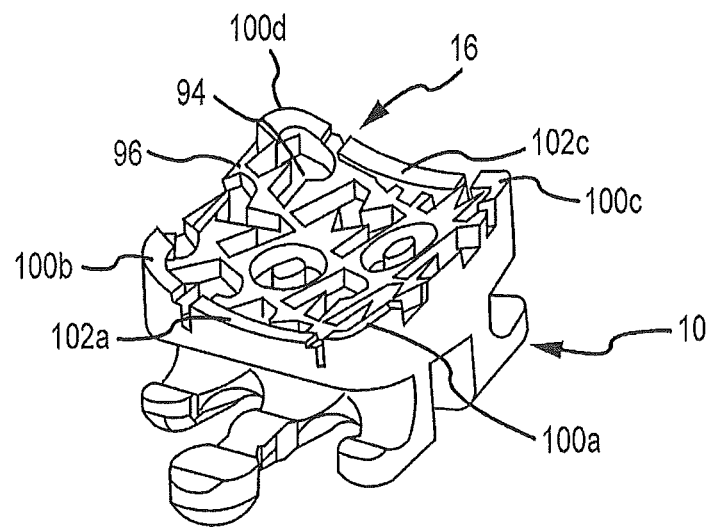
Figure 29:
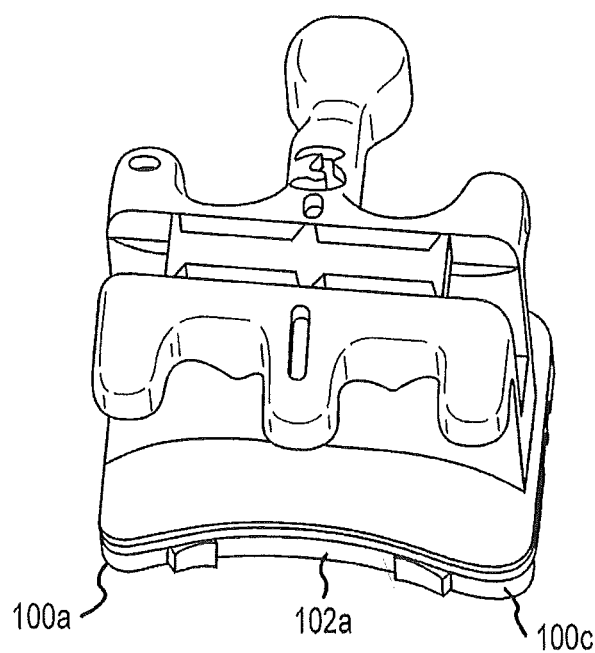
Figure 30:
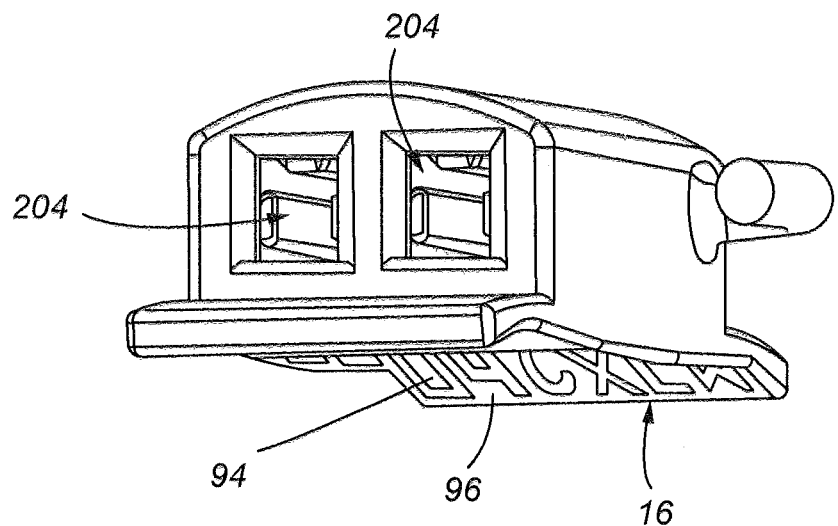
Figure 31:
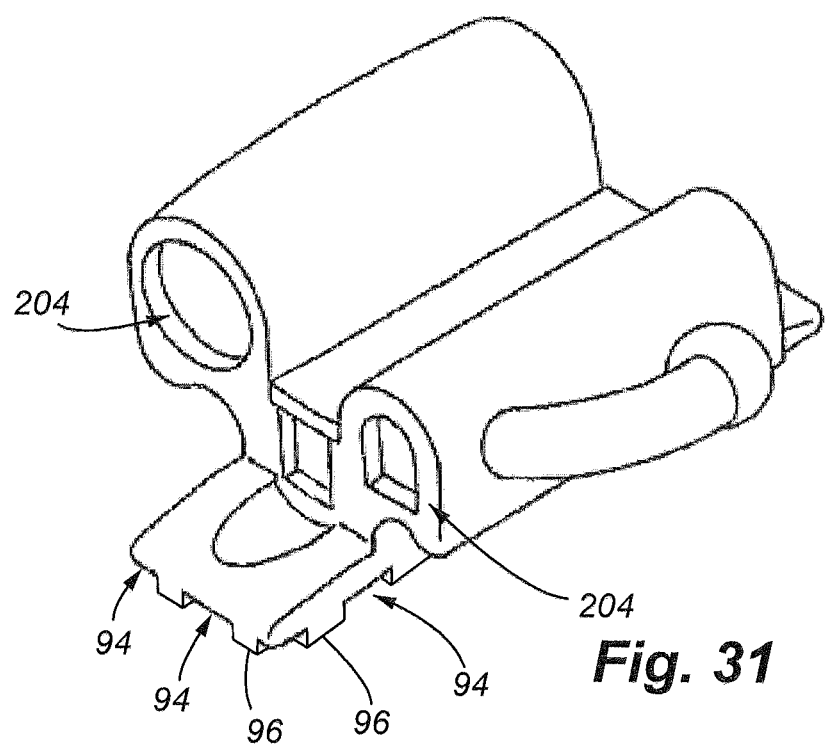
Figure 32:
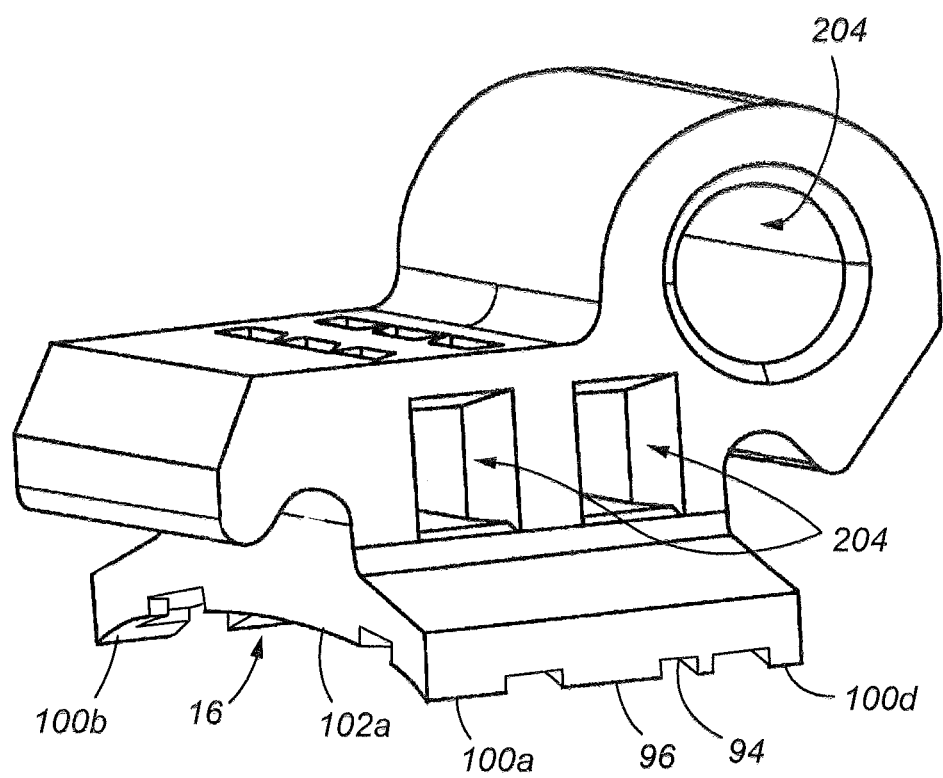
Figure 33:
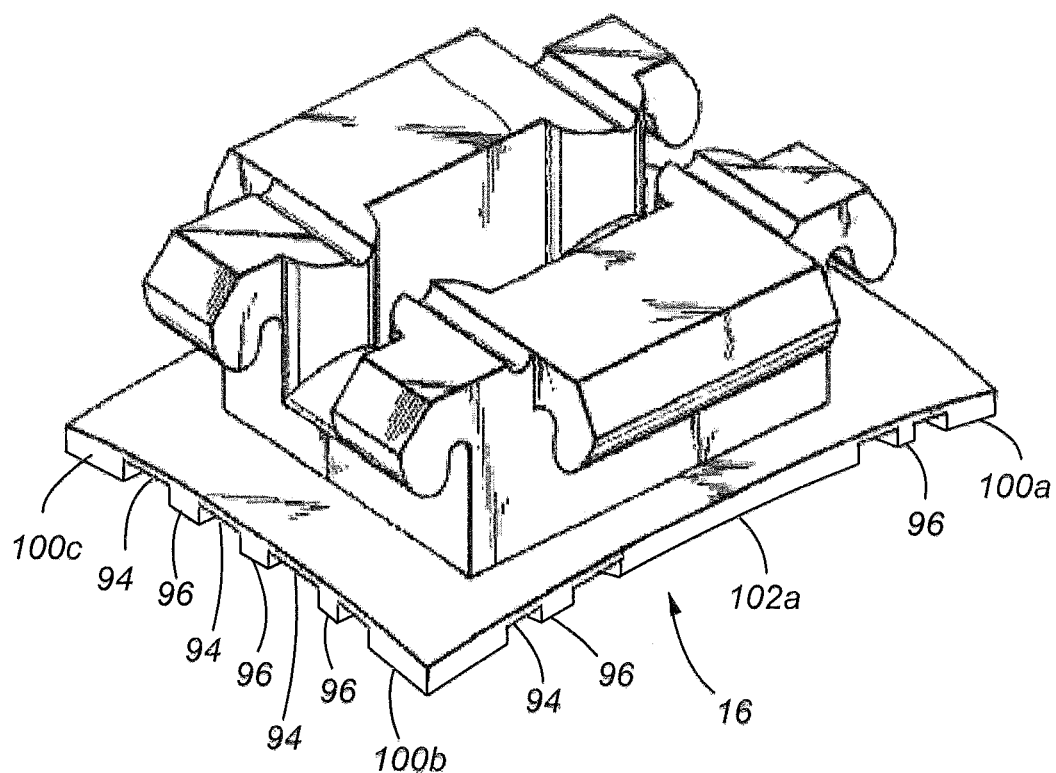
Figure 34:
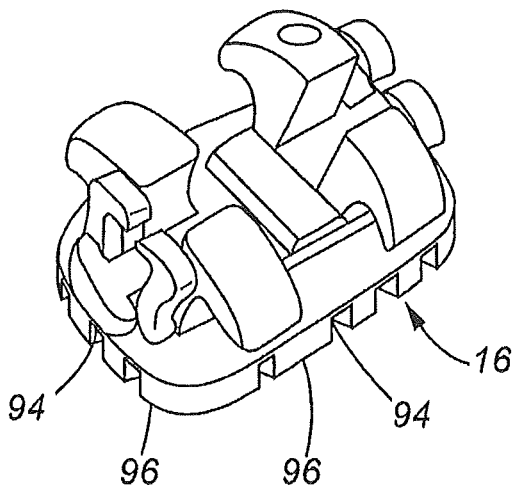
Figure 35B:
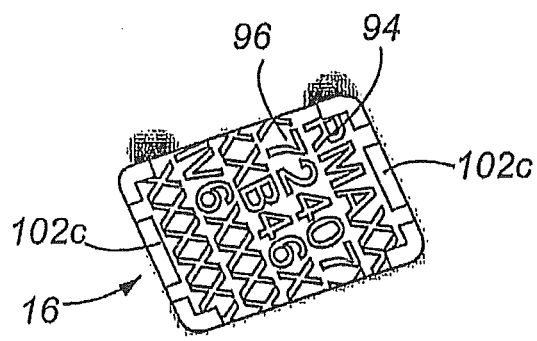
Figure 35A:
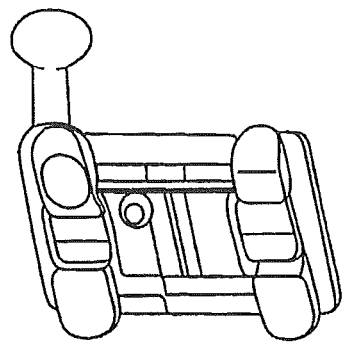
Figure 36:
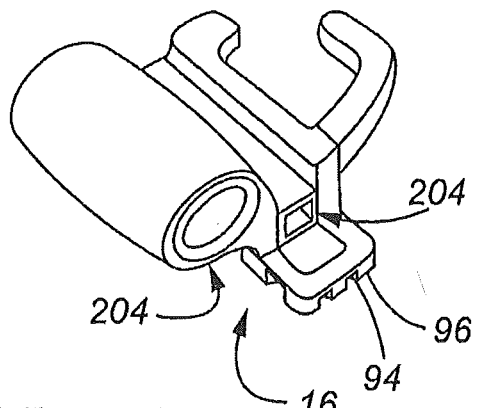
Figure 37:
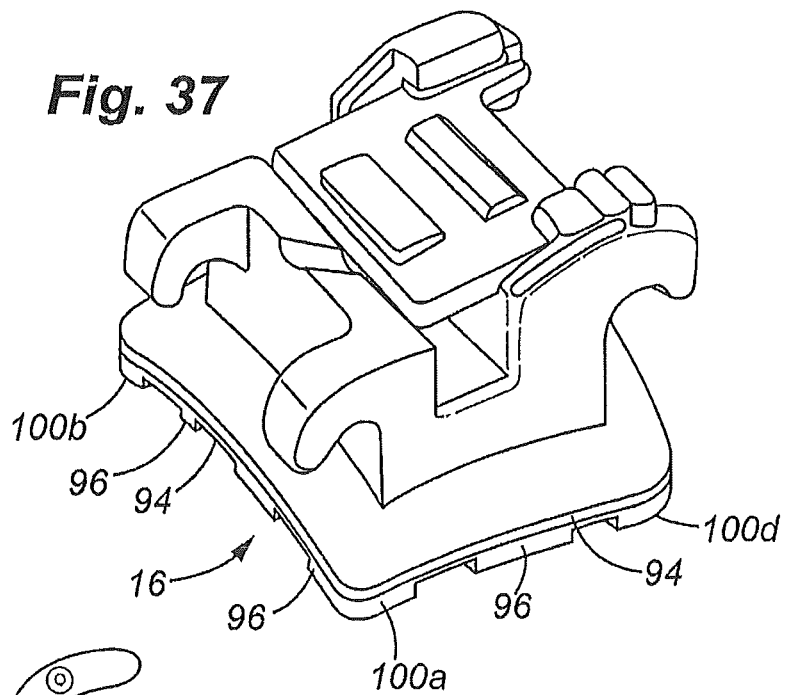
Figure 38:
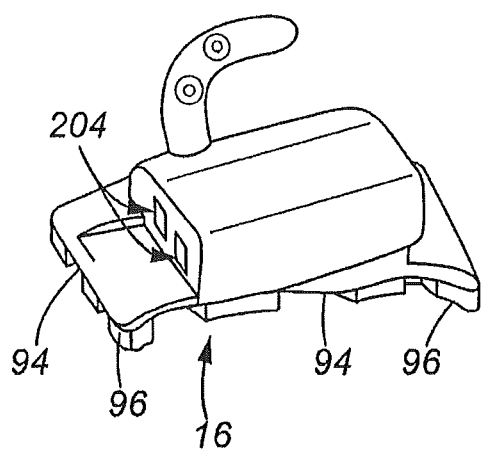
Figure 39:
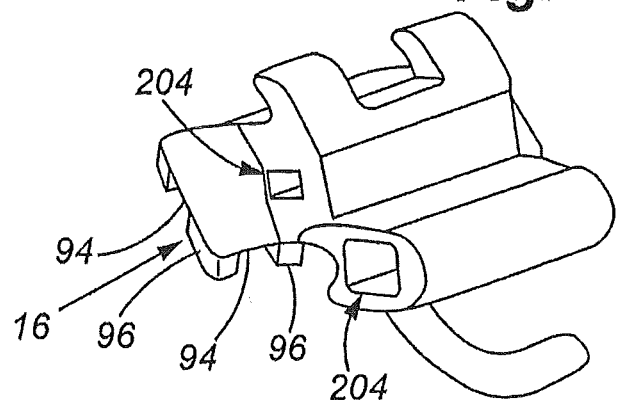

It is also important to bear in mind that there is a limitation on the depth of the most recessed base surface 92 relative to the more projected surface 90 (correspondingly, the extent of the walls 98 spanning between base surface levels), is limited in that as this depth increases, if the thickness of the body 8 of the orthodontic appliance extending away from its attached tooth does not correspondingly increase, then the orthodontic appliance can weaken. Accordingly, for at least most of the walls 98, the extent of the wall is between about 0.009 to 0.011 inches in depth, and more preferably, such walls span between the projected surface 92 and the recessed surface in a range of 0.010±0.0005 inches, this last range being particularly advantageous. However, it is within the scope of the present disclosure that there may be more than one level of recessed surface. In particular, the levels of recessed surfaces may roughly follow a curve for providing a uniform thickness of the body 8, and/or for providing at least a minimal orthodontic body thickness between each recessed surface and its corresponding appliance exterior surface facing away from the tooth to which the appliance is attached. Alternatively/optionally, the levels of recessed surfaces may roughly follow a curve of the base itself as shown in FIG. 28. Moreover, it is also within the scope of the definition of walls 98 that such walls may not be orthogonal to one or more of the surfaces 90 and 92. In particular, walls 98 may be at an incline of 45 degrees or greater relative to one or more of the surfaces 90 and 92.

Regardless of the nature of the characters 94 actually used, in a preferred embodiment, the base 16 does not have a grid between the characters 94. That is, in contrast to the bracket base shown in FIG. 13 of U.S. Pat. No. 5,595,484, the base 16 of the present disclosure does not have a grid or lattice within which the characters reside. Rather, the present disclosure describes providing characters 94 and a relatively irregular, non-grid like intermediate space 96 to cover the entire interior region 88. The characters 94 and intermediate space 96 thus function directly as the texturing that works in combination with the adhesive to more effectively bond the bracket to the tooth.

In a separate aspect of the present disclosure, the characters 94 may be angled at any orientation relative to the edges 86a, 86b, 86c, and 86d. More specifically, the characters may be oriented parallel with edges 86a and 86c, or perpendicular to edges 86a and 86c. Likewise, the characters may be oriented parallel with edges 86b and 86d, or perpendicular to edges 86b and 86d. Alternately, the characters 94 may be oriented at an angle relative to edges 86a, 86b, 86c, and 86d. As an example without limitation, FIG. 8 illustrates that the characters 94 are oriented at an angle θ of about 15 degrees relative to edges 86a and 86c, and at an angle of about 75 degrees relative to edges 86b and 86d.

Character length "L" and width "W" may vary considerably. Referring again to FIG. 8, in a preferred embodiment, in plan view, the length L of each characters 94 is about 0.034 to 0.040 inches, and more preferably, about 0.036 inches. The width W of each character 94 varies with the length and with the specific character type. For example, in the character string "RMO"® shown in FIG. 8, an "M" is typically wider than an "R" or an "O".

For each character 94, the line width "lw" preferably ranges between about 0.008 to 0.010 inches, where line width lw is the width of the line forming each individual character 94. Typically, line width lw will vary with character length L. Therefore, shorter characters 94 will typically have thinner line widths lw. Obviously, logos, and other symbols as well as certain graphics will have lengths L, widths W, and line widths lw as required to form each individual type of shape.

For each orthodontic appliance of the present disclosure, the total base surface area of the appliance is defined herein as the area between the edges of the appliance base 16 (e.g., edges 86a, 86b, 86c, and 86d of FIG. 8) for the base surfaces that are substantially parallel or non-parallel to the tooth's surface when the orthodontic appliance is applied to the tooth, wherein the non-parallel surfaces are the walls 98, and 99, FIG. 21 as described hereinbelow. The total two dimensional surface area is defined herein as total surface area of the base that is substantially parallel to the tooth when the orthodontic appliance is applied to the tooth. Accordingly, the total two dimensional base surface is substantially the sum of the recessed surface 92 area, and the projected surface 92 area. Thus, if the base 16 is rectangular and two dimensional, the total two dimensional base surface area is just the length of the base 16 multiplied by the width of the base 16. However, since the base 16 is generally curved to approximate the curvature of a tooth to which it is to be attached, the total two dimensional base surface area is greater than the length of the base 16 multiplied by the width of the base 16. Whether the characters 94 are letters, numbers, logos, symbols, or graphics, preferably the recessed surface 92 comprises between about 50% to 60% of the total two dimensional base surface area of the base 16, and more preferably, about 55% of the total two dimensional base surface area of base 16. Correspondingly, preferably the projected surface 90 comprises between about 40% to 50% of the total two dimensional base surface area of the base 16, and more preferably, about 45% of the total two dimensional base surface area of the base 16.

Projected surface 90 (e.g., FIG. 9A) and recessed surface 92 are comprised of characters 94 and intermediate space 96, which is situated between and around characters 94. Characters 94 may occupy the projected surface 90 of the base 16, but preferably occupy the recessed surface 92 of the base 16. Alternatively, intermediate space 96 may occupy the recessed surface 92 of base 16, but preferably occupy the projected surface 90 of base 16. However, in a preferred embodiment, upon attachment of the bracket 10 to the surface of a patient's tooth, intermediate space 96 is the projected surface 90 that is closer to the tooth surface than the characters 94 that are situated along the recessed surface 92. Separation between the characters 94 and intermediate space 96 is formed by bracket character walls 98 that are generally perpendicular or steeply sloped surfaces disposed between the characters 94 and the intermediate space 96. As shown in FIG. 9A, the projected surface 90 contacts the tooth surface upon attachment of the bracket 10 in the direction of arrows A2 to the patient's tooth T. Thus, as shown in FIG. 9A, when the intermediate space 96 occupies the projected surface 90, the intermediate surface 96 is closest to the tooth surface, and the location of characters 94 is recessed relative to the location of intermediate space 96. In contrast, FIG. 9B presents the same cross-sectional view of base 16 as that shown in FIG. 9A, but with the characters 94 and intermediate space 96 inverted. That is, in this modified arrangement, the location of intermediate space 96 is recessed relative to the location of the characters 94. Therefore, the characters 94 contact the tooth surface upon attachment of the bracket 10 in the direction of arrows A2 to the patient's tooth T.

Figure 10:
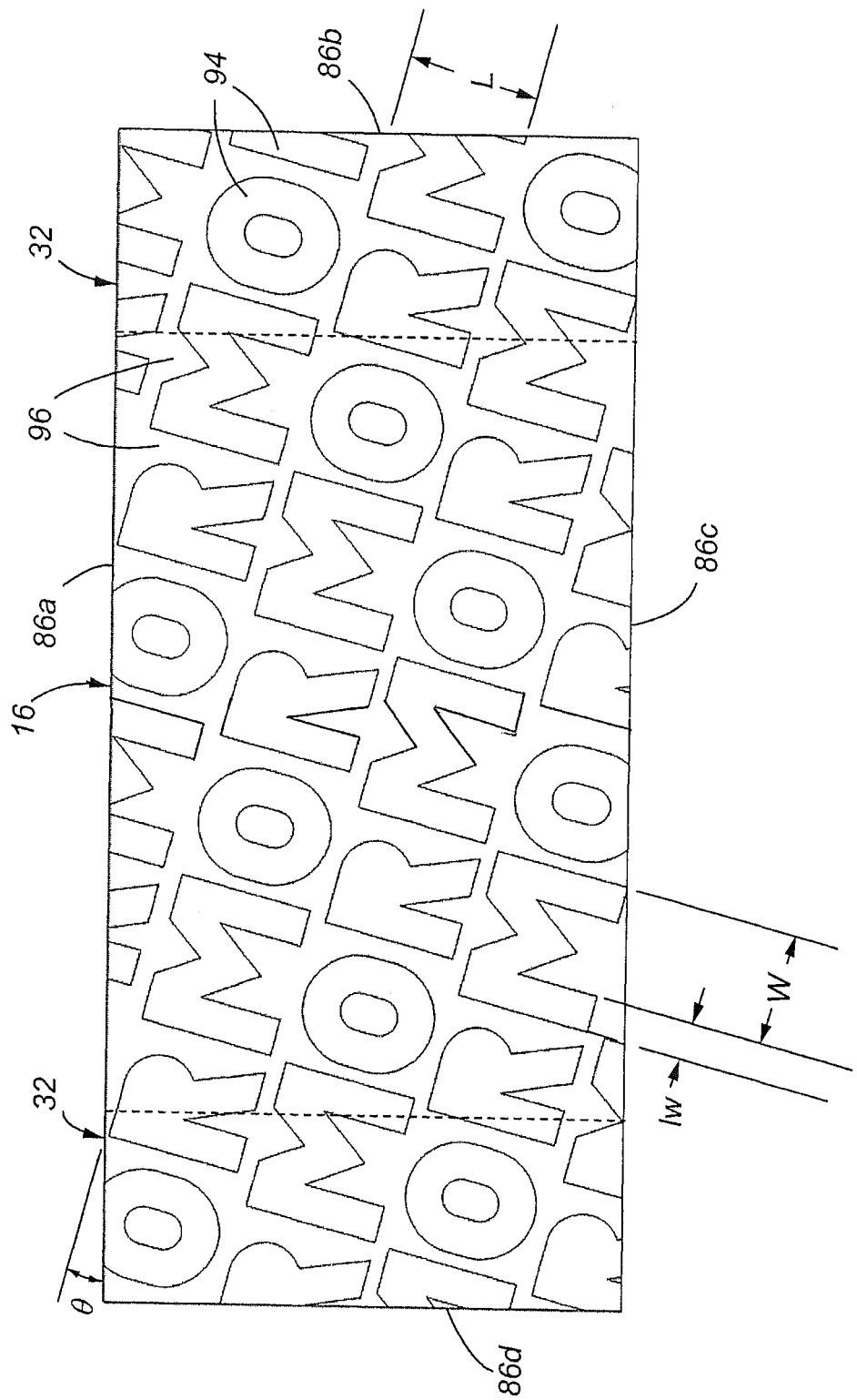
FIG. 10 is a rear or underneath view of the base 16 of an orthodontic appliance, e.g., the bracket shown in FIG. 4B with the flanges, and including a character base pattern.

Referring now to FIGS. 4B and 10, a bracket 10 with a continuous and uninterrupted base 16 and flanges 32 is shown. When flanges 32 are incorporated into the base 16 having characters 94, the characters 94 are preferably extended across the entire rear surface of the bracket 10. Preferably, the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total two dimensional surface area of the base 16 and the flanges 32, and more preferably, about 55% of the total two dimensional surface area of base 16 and the flanges 32. Correspondingly, preferably the projected surface 90 comprises between about 40% to 50% of the total two dimensional surface area of the base 16 and the flanges 32, and more preferably, about 45% of the total two dimensional surface area of the base 16 and the flanges 32. These preferred values have been found to provide better adhesion characteristics between the bracket and the tooth to which it is applied.

Figure 11A:
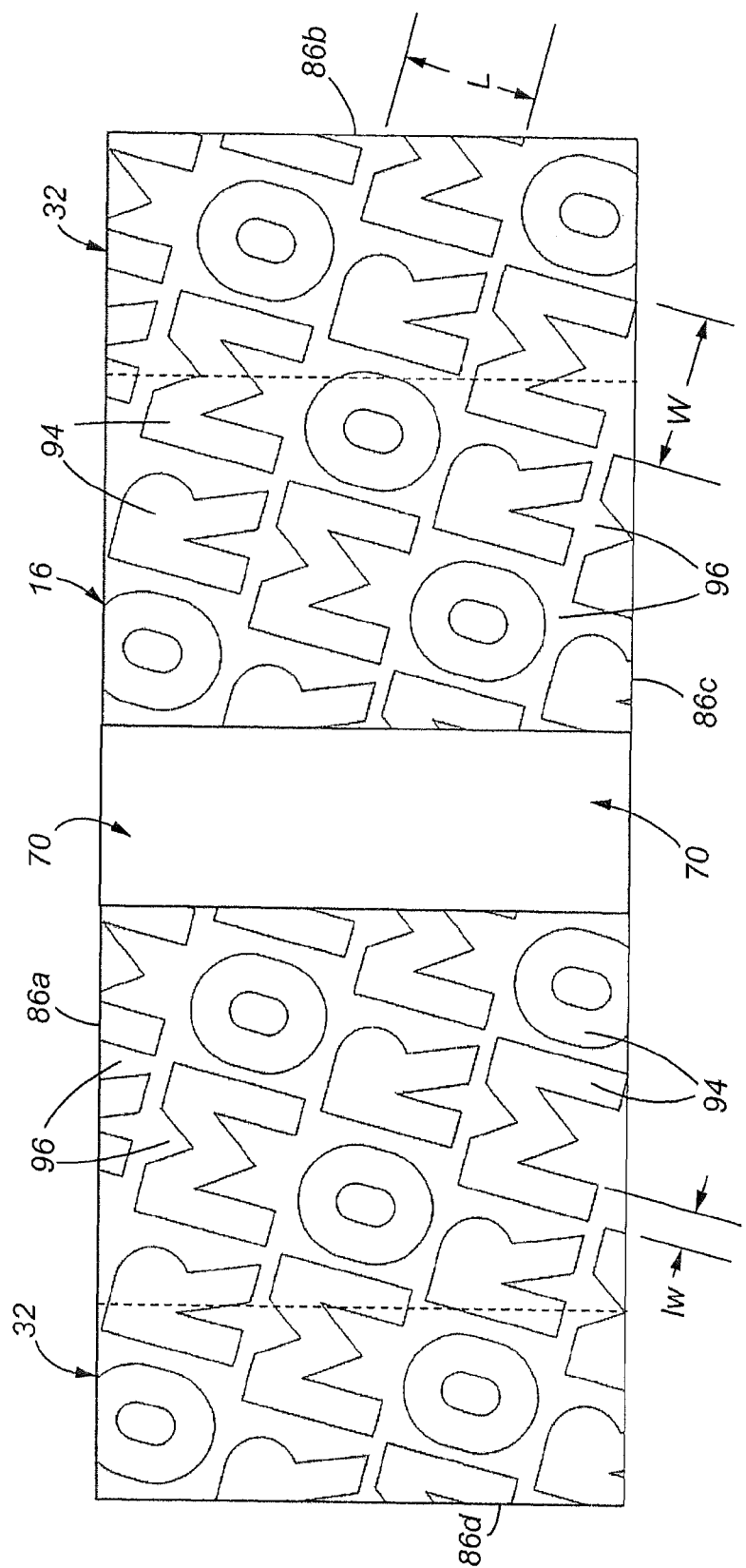
FIG. 11A shows the base of an orthodontic appliance, e.g., the bracket 10 shown in FIGS. 1B and 5B with the flanges, and including a character base pattern and an auxiliary slot without a character pattern in the auxiliary slot.
Figure 11B:
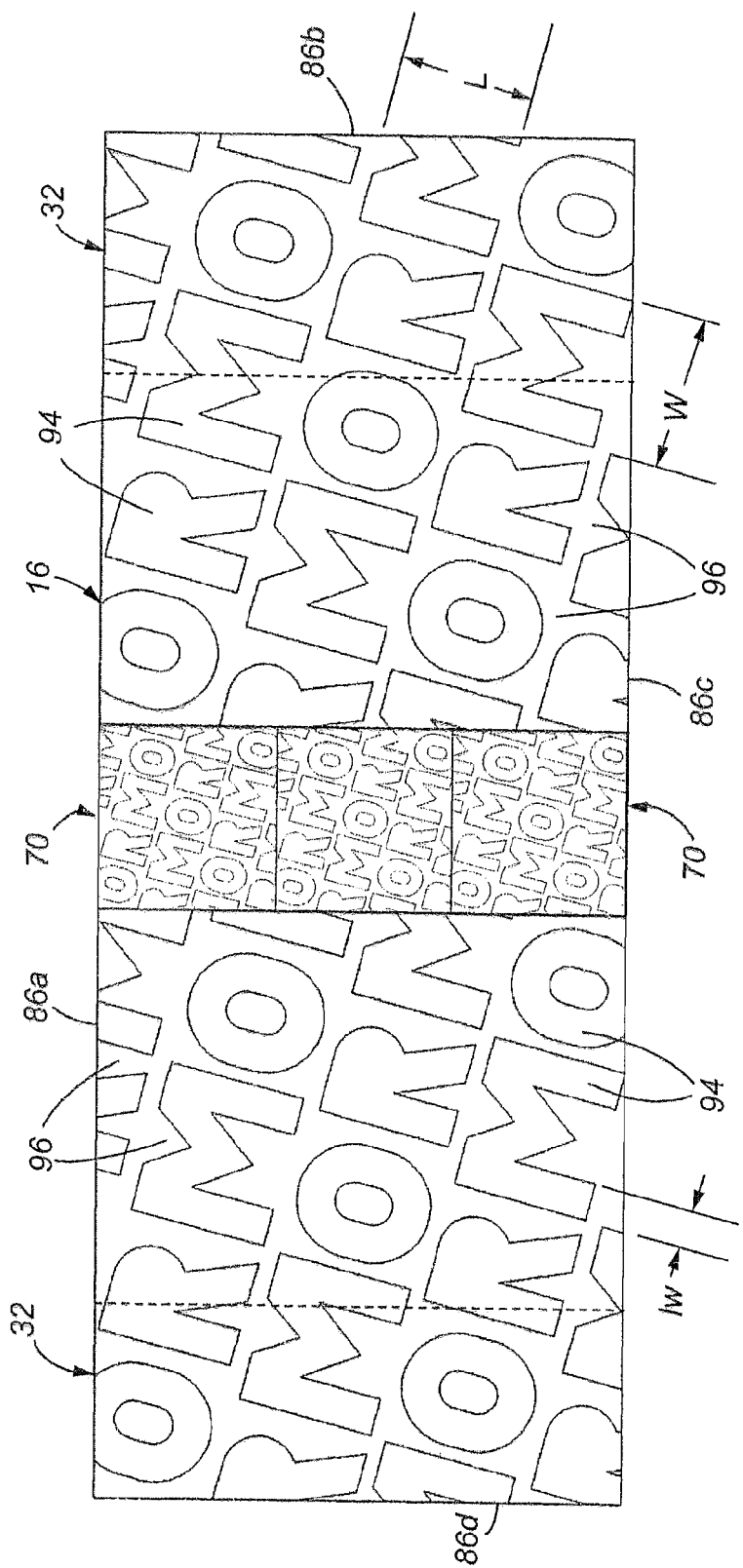
FIG. 11B shows the base of an orthodontic appliance, e.g., the bracket shown in FIGS. 1B and 5B with the flanges, wherein the base includes a character base pattern and an auxiliary slot with a character pattern in the auxiliary slot.
Figure 20:
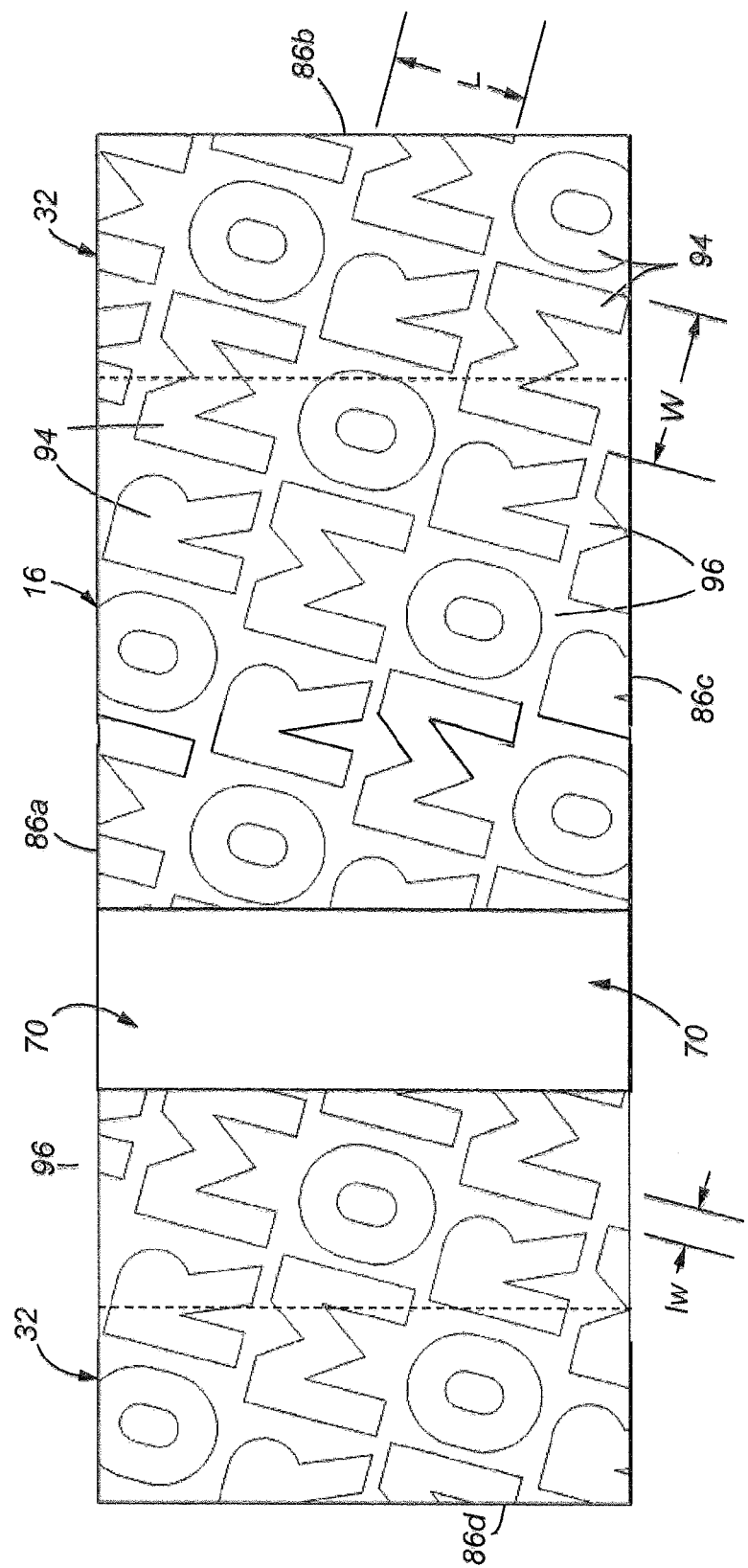
FIG. 20 shows the base of an orthodontic appliance having a character pattern for identifying the supplier of the appliance, wherein there is a single auxiliary slot that is offset from the center of the base 16.

Referring again to FIGS. 1B and 5B, a bracket 10 having a base 16 with a single auxiliary slot 70 is shown. However, such an auxiliary slot 70 need not be centrally located along the mesial-distal extent of the bracket. Instead, the auxiliary slot 70 more to the mesial side of the bracket, or more to the distal side of the bracket. Indeed, FIG. 20 shows such an offset auxiliary slot 70 provided in the base 16 of an orthodontic appliance. A rear plan view of the base of FIGS. 1B and 5B is shown in FIGS. 11A and 11B (although these latter figures may equally well apply to the base 16 of other types of orthodontic appliances, e.g., those having tubes), wherein the rear of the bracket 10 incorporates characters 94. For the bracket (or other orthodontic appliance) shown in FIG. 11A, when flanges 32 are incorporated into the base 16 having characters 94, the characters 94 are preferably extended across the entire rear surface of the bracket 10, with the exception of the area occupied by the auxiliary slot 70. Consistent with the other embodiments described above, preferably the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total two dimensional surface area of the base 16 (not including the area occupied by the auxiliary slot 70) and the flanges 32, and more preferably, about 55% of the total two dimensional surface area of base 16 (not including the area occupied by the auxiliary slot 70) and the flanges 32. Correspondingly, preferably the projected surface 90 comprises between about 40% to 50% of the total two dimensional surface area of the base 16 (not including the area occupied by the auxiliary slot 70) and the flanges 32, and more preferably, about 45% of the total two dimensional surface area of the base 16 (not including the area occupied by the auxiliary slot 70 and the flanges 32. These preferred values have been found to provide better adhesion characteristics between the bracket and the tooth to which it is applied. Accordingly, a determination may be as to whether the characters 94 are provided on the recessed surface 92, or on the projected surface 90 depending on which of these alternatives most closely yields the above preferred surface percentages for the recessed and projected surfaces.

Referring now to FIG. 11B, the orthodontic appliance base 16 includes a character pattern 94 within the area of the auxiliary slot 70. When characters 94 are integrated into the auxiliary slot 70, the characters 94 may have different dimensions than that of the remaining base 16. Preferably, the character pattern 94 may be finer, thus limiting the probability of a tool to be inserted therein from hanging-up or catching on the characters 94. Alternatively, the character pattern 94 in the auxiliary slot 70 may have a rounded (not shown) or alternatively textured exterior surface that advantageously interacts with the tool to be inserted therein.

Figure 12A:
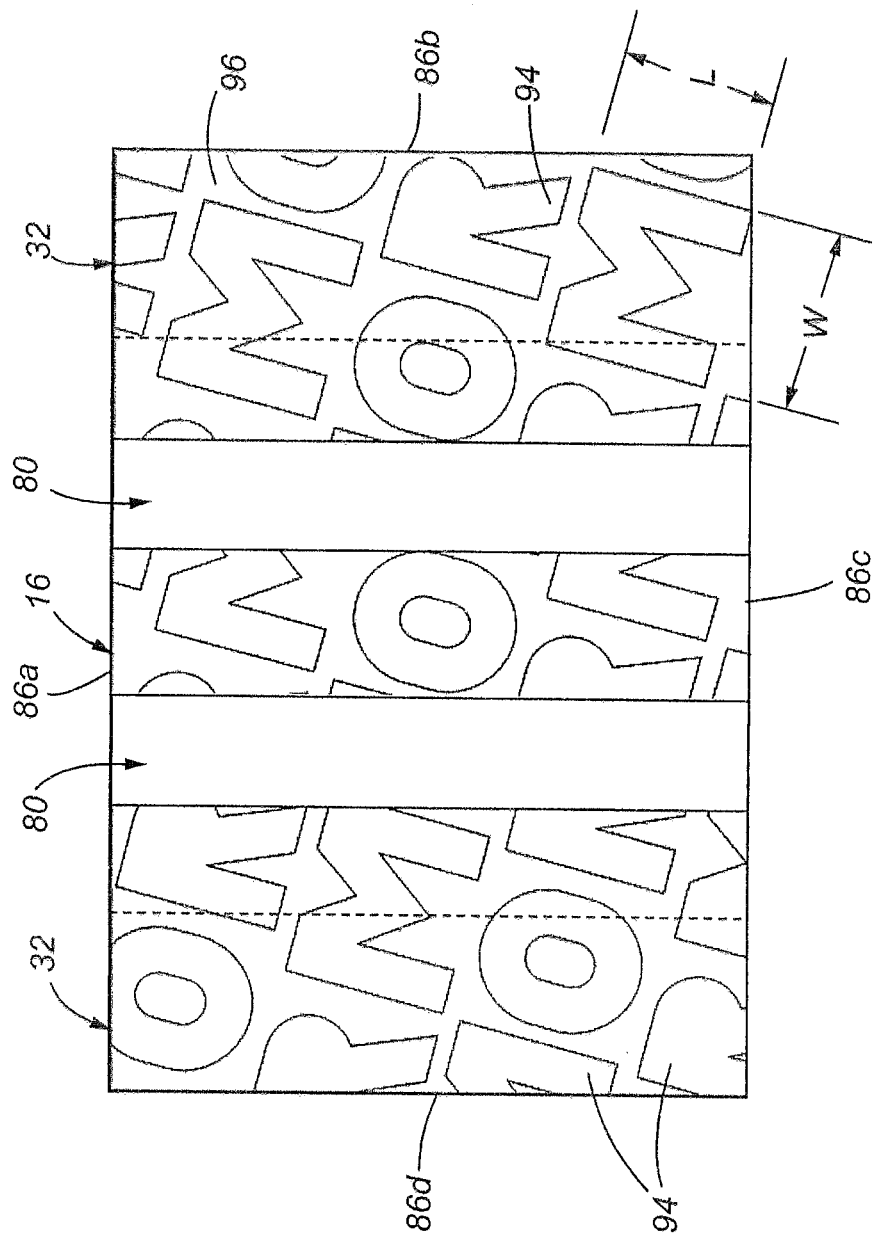
FIG. 12A shows the base of an orthodontic appliance, e.g., the bracket shown in FIG. 6B with flanges, wherein the base includes a character base pattern and twin auxiliary slots without a character pattern in the auxiliary slots.
Figure 12B:
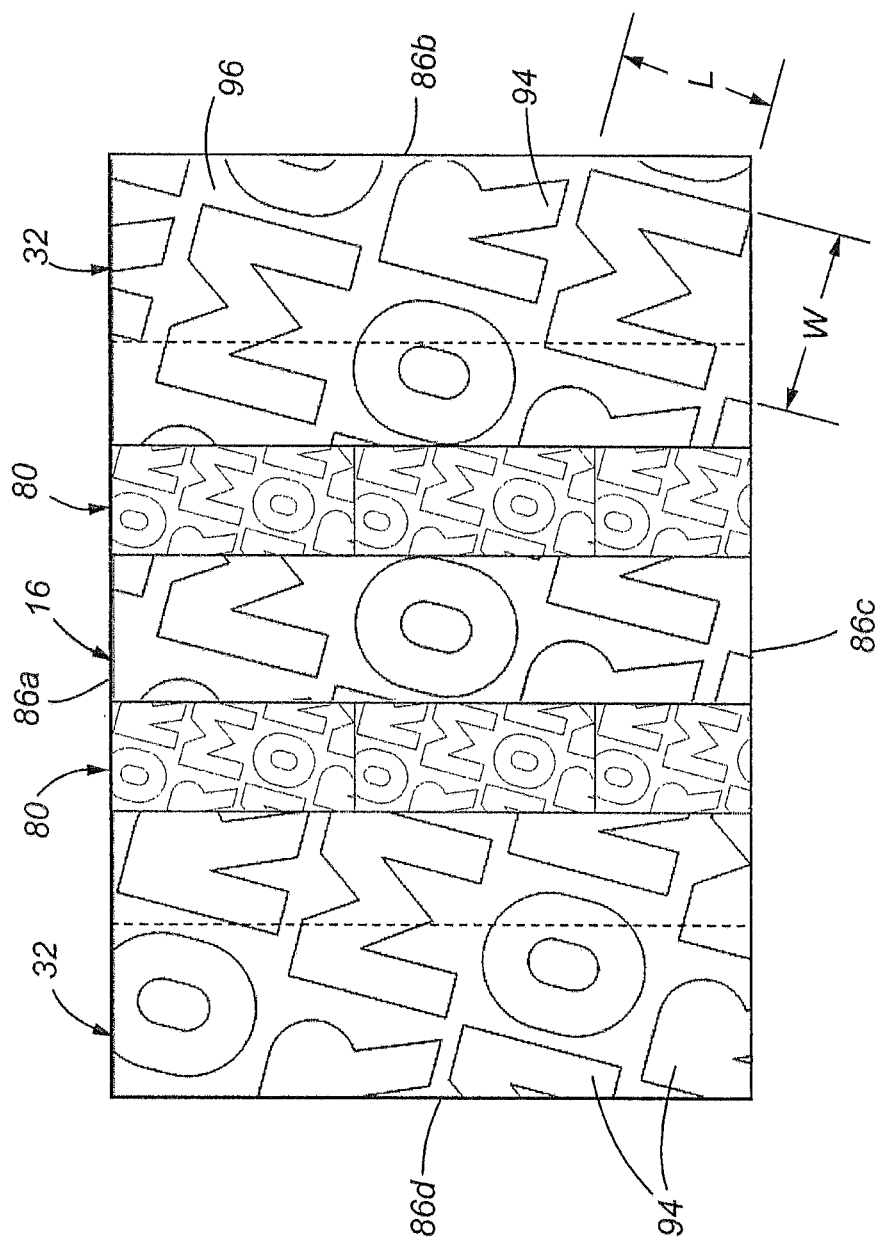
FIG. 12B shows the base of an orthodontic appliance, e.g., the bracket shown in FIG. 6B with flanges, wherein the base includes a character base pattern and twin auxiliary slots with a character pattern in the auxiliary slots.
Figure 13:
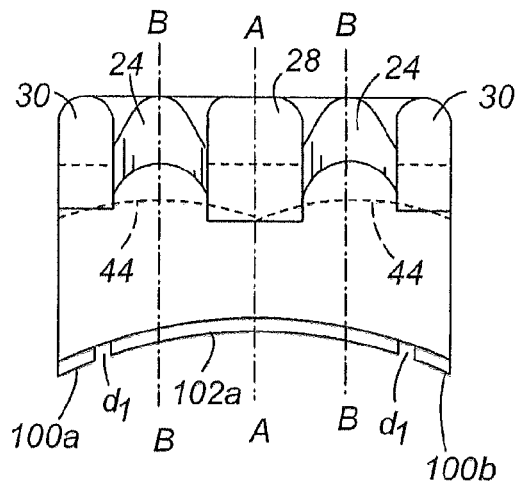
FIG. 13 is a plan view of the bracket of FIG. 4B without flanges, and including a discontinuous perimeter rail.

Referring again to FIG. 3B, a bracket 10 having a base 16 with twin auxiliary slots 80 is shown. A plan view of the rear of FIG. 3B is shown in FIGS. 12A and 12B (although these latter figures may equally well apply to the base 16 of other types of orthodontic appliances, e.g., those having tubes), wherein the rear of the bracket 10 incorporates characters 94. For the base 16 shown in FIG. 12A, when flanges 32 are incorporated into the base 16 having characters 94, the characters 94 are preferably extended across the entire rear surface of the orthodontic appliance, with the exception of the area occupied by the twin auxiliary slots 80. Consistent with the other embodiments described above, preferably the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total two dimensional surface area of the base 16 (not including the area occupied by the twin auxiliary slots 80) and the flanges 32, and more preferably, about 55% of the total two dimensional surface area of base 16 (not including the area occupied by the twin auxiliary slots 80) and the flanges 32. Correspondingly, preferably the projected surface 90 comprises between about 40% to 50% of the total two dimensional surface area of the base 16 (not including the area occupied by the twin auxiliary slots 80) and the flanges 32, and more preferably, about 45% of the total two dimensional surface area of the base 16 (not including the area occupied by the twin auxiliary slots 80) and the flanges 32. These preferred values have been found to provide better adhesion characteristics between the bracket (more generally, orthodontic appliance) and the tooth to which the appliance is applied.

Referring now to FIG. 12B, the base 16 shown includes a character pattern 94 within the area of the auxiliary slots 80. As with the single auxiliary slot 70 shown in FIG. 11B, when characters 94 are integrated into the auxiliary slots 80, the characters 94 may have different dimensions than that of the remaining base 16. Preferably, the character pattern 94 may be finer, thus limiting the probability of a tool to be inserted therein from hanging-up or catching on the characters 94. Alternatively, the character pattern 94 in the auxiliary slots 80 may have a rounded (not shown), or alternatively textured exterior, surface that advantageously interacts with the tool to be inserted therein. Note that such an auxiliary slots 80 need not be symmetrically located along the mesial-distal extent of the bracket. Instead, the auxiliary slots 80 more to the mesial side of the bracket, or more to the distal side of the bracket. The auxiliary slots 80 may be provided in locations along the base 16 according to the auxiliary tool to be fitted therein. Thus, one such auxiliary slot 80 may be near the mesial edge of the base 16, whereas the other auxiliary slot may near the center of mesial-distal extent of the base.

Referring again to FIG. 4B, in yet a separate aspect of the disclosure, the bracket 10 (more generally, an orthodontic appliance) may include a curved base 16. The base 16 may be contoured at a variety of angles depending upon the curvature of the patient's tooth surface.

Referring now to FIGS. 13-15A,B in yet a separate aspect of the disclosure, base 16 of an orthodontic appliance (e.g., bracket 10 or another appliance) preferably includes a perimeter rail, and more preferably, a discontinuous perimeter rail. The discontinuous perimeter rail preferably includes at least one corner segment, and more preferably, a plurality of corner segments, including a distal/gingival corner 100a, a gingival/mesial corner 100b, a mesial/occlusal corner 100c, and an occlusal/distal corner 100d. Corners 100a, 100b, 100c, and 100d are preferably between about 0.008 to 0.011 inches in width "cw", and more preferably, are about 0.085 inches wide. Each corner 100a, 100b, 100c, and 100d is separated from the other corners segments by a distance or a cavity. Preferably, the discontinuous perimeter rail also includes at least one straight segment, and more preferably, a plurality of straight segments. More preferably yet, two straight segments are provided, namely a gingival straight segment 102a and an occlusal straight segment 102c. The gingival straight segment 102a is separated from the distal/gingival corner 100a and the gingival/mesial corner 100b by a cavity or a distance "$d_1$" of about 0.008 to 0.011 inches, and more preferably, by a distance $d_1$ approximately equal to the width cw (FIG. 14) of the discontinuous perimeter rail, or about 0.0085 inches. Similarly, the occlusal straight segment 102c is separated from the mesial/occlusal corner 100c and the occlusal/distal corner 100d by a cavity or distance $d_1$ of about 0.008 to 0.011 inches, and more preferably, by a distance $d_1$ approximately equal to the width cw of the discontinuous perimeter rail, or about 0.0085 inches. Although base 16 of an orthodontic appliance will function without a perimeter rail, the discontinuous perimeter rail in combination with characters 94 increases the bonding strength of orthodontic appliance when it is attached to a tooth using an adhesive.

Referring again to FIG. 14, although it may be present, in a preferred embodiment, the discontinuous perimeter rail does not include a distal straight segment between the distal/gingival corner 100a and the occlusal/distal corner 100d. In addition, in a preferred embodiment, the discontinuous perimeter rail does not include a mesial straight segment between the gingival/mesial corner 100b and the mesial/occlusal corner 100c.

Figure 14:
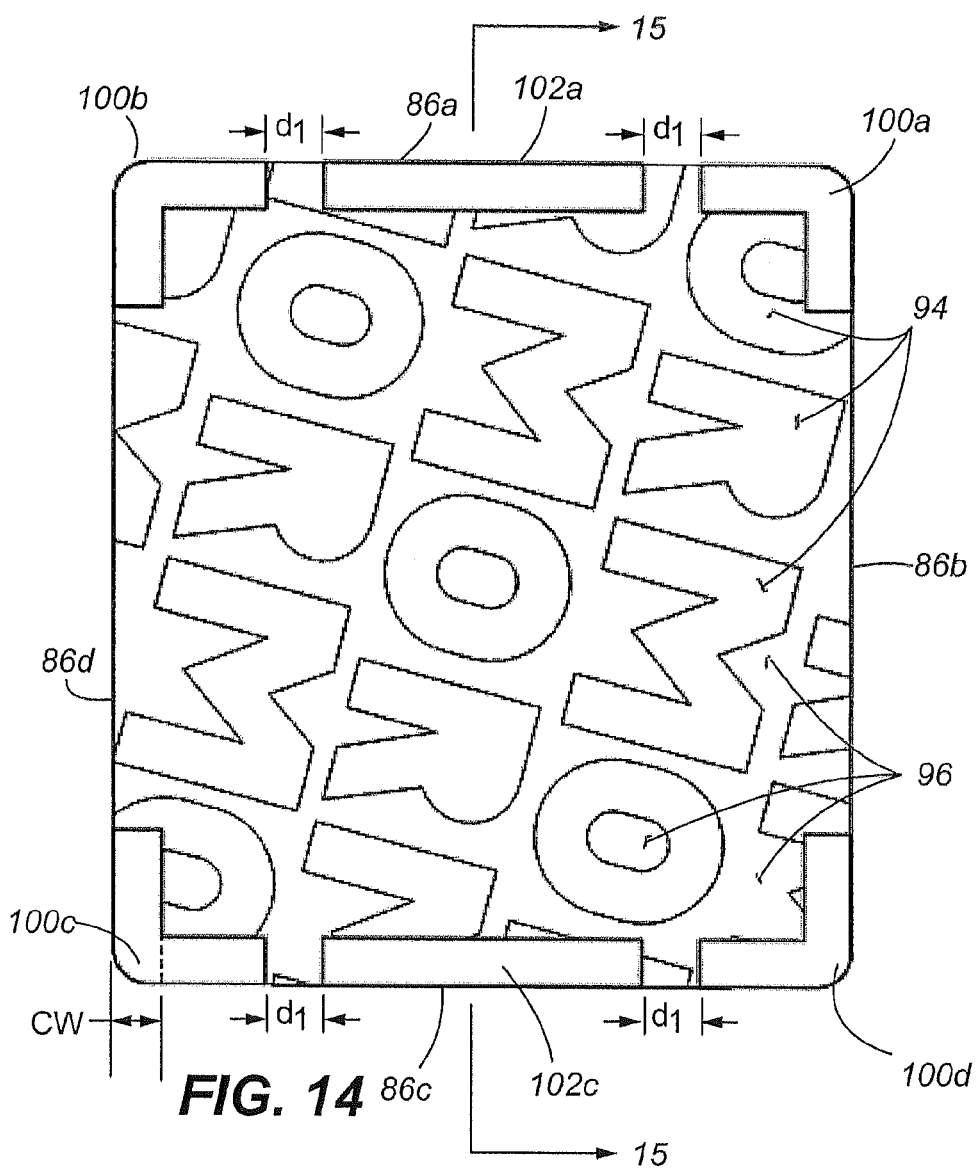
FIG. 14 is a rear or underneath view of the base of the bracket shown in FIG. 13.

Still referring to FIG. 14, in a preferred embodiment, the perimeter rail is preferably positioned within the base 16 area defined by edges 86a, 86b, 86c, and 86d. More specifically, corners 100a, 100b, 100c, and 100d, as well as straight segments 102a and 102c of the discontinuous perimeter rail are all disposed within the interior of the area defined by base edges 86a, 86b, 86c, and 86d. The total two dimensional surface area in rear elevation view, or the exterior surface of the base 16 is defined herein as the area in rear elevation view between edges 86a, 86b, 86c, and 86d for the base surfaces parallel to the tooth's surface. Where a discontinuous perimeter rail is used, the discontinuous perimeter rail portions 100a, 100b, 100c, 100d, 102a and 102c comprise between about 12% to 16% of the total two dimensional surface area of the base 16, and more preferably, about 14% of the total two dimensional surface area of base 16. Whether the characters 94 are letters, numbers, logos, symbols, or graphics, when a discontinuous perimeter rail is present, preferably the recessed surface 92 comprises between about 45% to 50% of the total two dimensional surface area of the base 16, and more preferably, about 48% of the total two dimensional surface area of base 16. Correspondingly, when a discontinuous perimeter rail is present, preferably the projected surface 90 comprises between about 35% to 40% of the total two dimensional surface area of the base 16, and more preferably, about 38% of the total two dimensional surface area of the base 16.

Figure 15A:
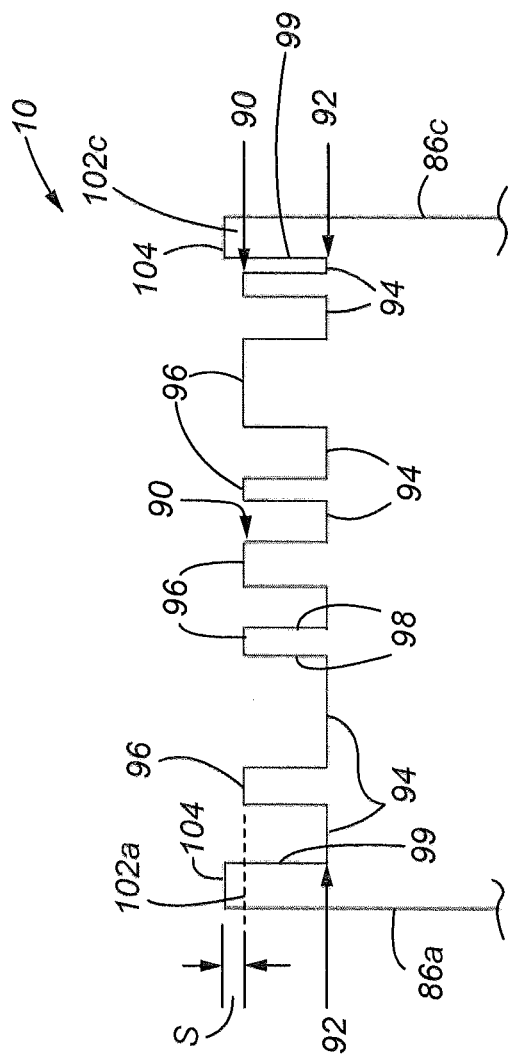
FIGS. 15A-B are cross-sections taken along sectioning plane 15-15 of FIG. 14, this plane represented by the line segments identified with the labels 15.
Figure 15B:
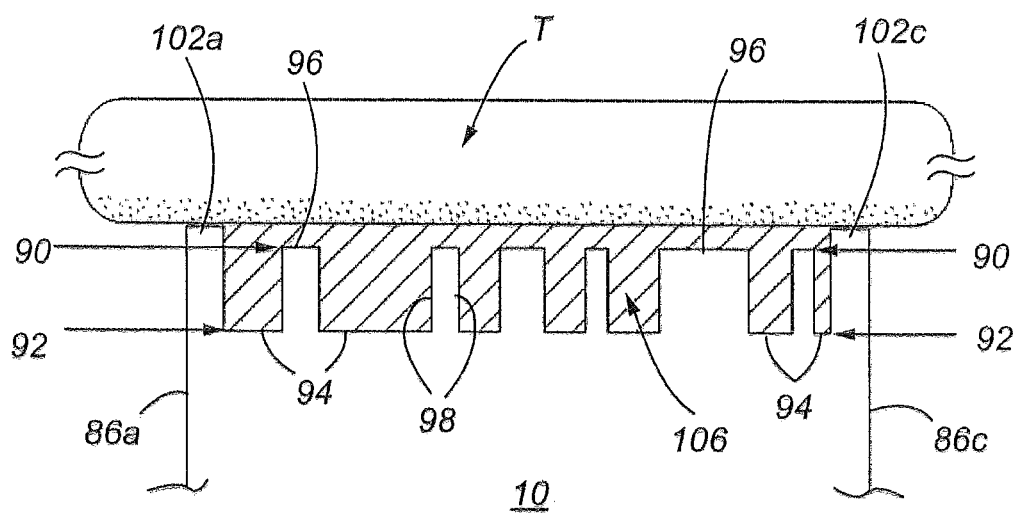

Referring now to FIG. 15A, a cross-sectional view along line 15-15 as shown in FIG. 14 is provided. The cross-sectional view of FIG. 15A shows the gingival straight segment 102a and the occlusal straight segment 102c along the gingival and occlusal edges of the orthodontic appliance whose base 16 is shown in FIG. 14. FIG. 15A also shows that the rail surface 104 is disposed beyond the projected surface 90. In the preferred embodiment depicted in FIG. 15A, the projected surface 90 is comprised of the intermediate space 96 between characters 94, while the recessed surface 92 is comprised of the characters 94. The rail surface 104 preferably projects a distance "s" of about 0.002 to 0.004 inches beyond the projected surface 90, and more preferably, the rail surface 104 projects about 0.003 inches beyond the projected surface 90. Thus, when the orthodontic appliance of FIG. 14 having a discontinuous rail is placed with its base 16 in contact with a patient's tooth, the rail surface 104 contacts the patient's tooth. The discontinuous rail thus forms a pocket for the collection of adhesive. Thus, upon application of the orthodontic appliance of FIG. 14 to a patient's tooth, the openings between the perimeter rail permit excess adhesive to escape under the applied pressure, thereby preventing the appliance from having an adhesive layer that is too thick and moving away from the tooth as a result of increased hydraulic pressure formed within the adhesive pocket when the appliance is first pressed against the tooth to which it is being applied. Thus, the discontinuous structure of the perimeter rail improves the bonding strength between the orthodontic appliance and the patient's tooth because it allows excess adhesive to escape during the application of the appliance to the tooth's surface. Furthermore, as shown in FIG. 15B, the difference in distance provided by the projection of the perimeter rail beyond the projected surface 90 allows a layer of adhesive 106 to bond between the projected surface 90 and the tooth's surface. Thus, a layer of adhesive is formed within the entire interior area 88 of the base that is not otherwise occupied by the discontinuous perimeter rail segments 100a-d, and 102a and 102c. This further improves bonding between the orthodontic appliance and the tooth's surface.

Referring to FIGS. 14 and 15A, as one of skill in the art will understand, the walls 98 (FIG. 15A) together with the rail walls 99 provide substantially more base surface area to which an adhesive can bond. In fact, the embodiment of FIG. 14 results in approximately a base total surface area increase of more than 140%. This can be seen as follows. Since all walls 98 and 99 are at least the height of walls 98, assume for the moment that the height of all walls is the same as walls 98. An approximation to the increase in base total surface area by the walls can be obtained by comparing:
 (a) the sum of the line segments of the extent of the walls 98 and 99 (FIG. 15A), plus, the line segments residing on the projected surface 90 and on the recessed surface 92 of both cross section in FIG. 15A with
 (b) the straight line extent of the base 16 along cross section 15-15 of FIG. 14.

Accordingly, since the wall height is approximately 0.12 of the straight line extent across the base 16 of FIG. 14 at cross section identified by the sectioning plane 15-15, and since there are 12 walls in the cross section shown in FIG. 15A, an approximation to the ratio of: (1) the base surface area immediately surrounding the cross section 15-15 to (2) a non-embedded (e.g., two dimensional) base surface area surrounding the cross section 15-15 to the same extent is approximately (0.12×12) to 1.0 which is 1.44:1.0. Moreover, this ratio holds up over a fine sampling of cross sections of FIG. 14. In particular, for a substantially regularly spaced sampling of 25 cross sections parallel to the cross section of 15-15 of FIG. 14, this same ratio of 1.44:1.0 is obtained. Accordingly, since there may be relatively little curvature in the gingival-occlusal direction of the orthodontic appliance, it is believed that FIG. 14 shows a base 16 with an increase of total surface area of approximately 44% over a corresponding base surface area that does not have characters formed therein; i.e., 144% of the corresponding base surface area that does not have characters formed therein, or equivalently, at least 29% of the total surface area of the base 16 is derived from the surface area of the walls 98 and 99. Moreover, it is believed this approximate increase is somewhat conservative since the extra height of the perimeter rail walls over the projected areas of the base are not included in the above approximation. Furthermore, the increase in total surface area of the base 16 may be made greater by decreasing the width of the font used, and increasing the number of characters (e.g., by providing a greater number of occurrences of the separation character.

Figure 16:
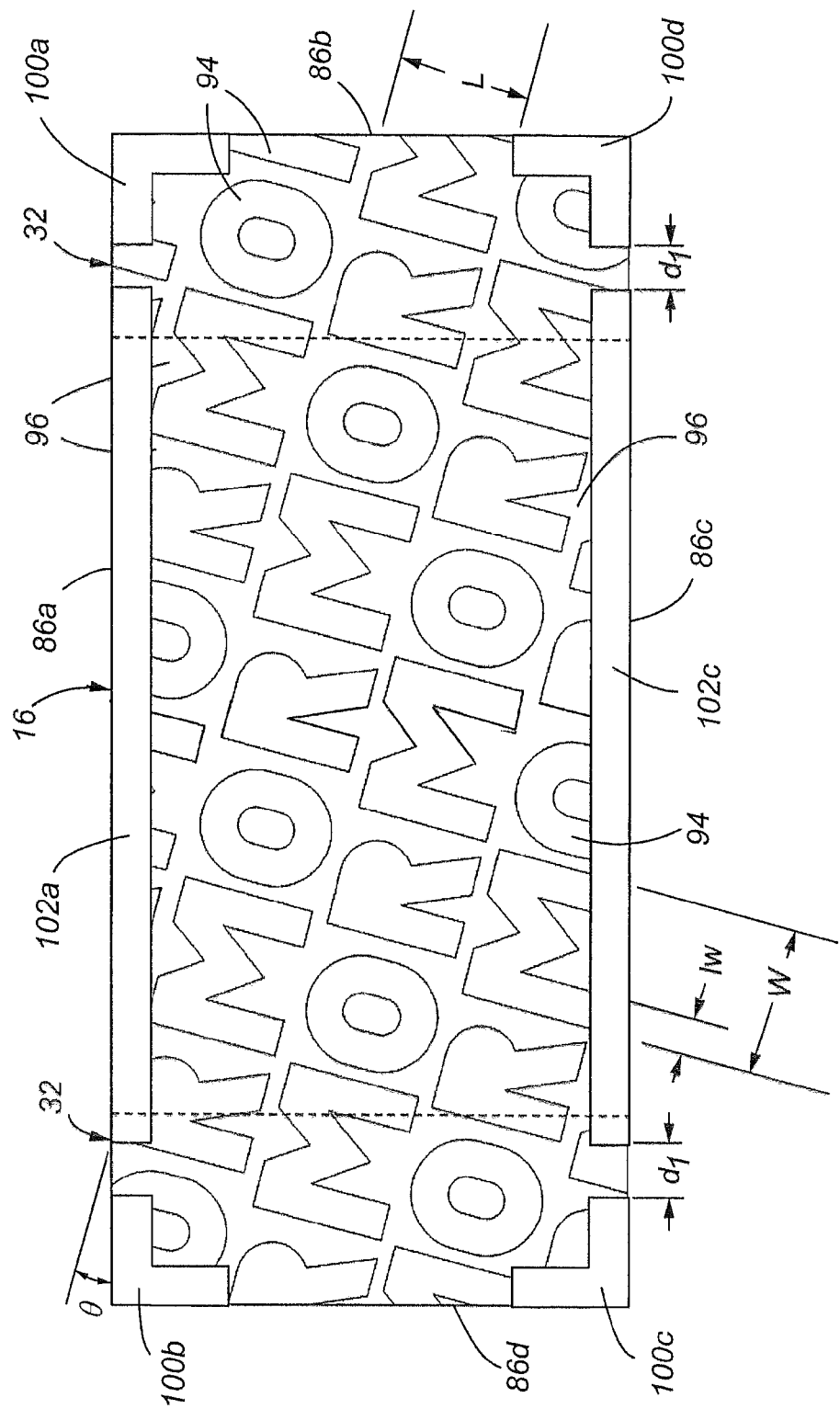
FIG. 16 is a rear view of the base of an orthodontic appliance, e.g., the bracket shown in FIG. 4B with flanges, and including a character base pattern and a discontinuous perimeter rail.

Referring now to FIG. 16, for those orthodontic appliances that include flanges 32 adjacent the base 16, the perimeter rail is preferably located along the outermost edges of the flanges 32. Thus, the discontinuous perimeter rail portions 100a, 100b, 100c, and 100d will occupy the corners formed at the outer limits of the flanges 32. In addition, the gingival straight segment 102a and the occlusal straight segment 102c will occupy portions of the gingival edge 86a and the occlusal edge 86c, respectively. The gingival straight segment 102a and the occlusal straight segment 102c can occupy area along both the base 16 and the flanges 32, depending upon the chosen perimeter rail configuration. In addition, for those orthodontic appliances that include a single auxiliary slot 70 or twin auxiliary slots 80, the perimeter rail is preferably not present along the alignment of the auxiliary slot 70 or slots 80.

In yet a separate aspect of the disclosure, a method of making an orthodontic appliance (e.g., the bracket 10) and its base 16 is disclosed wherein the method is specifically suited for providing a base 16, and optionally flanges 32, having a pattern of characters 94 formed or embedded within the base. In a preferred embodiment, a one-piece molded metal injected orthodontic appliance (e.g., bracket 10) is manufactured from a mold 108. As known to those skilled in the art, the mold 108 (FIG. 17) is produced by electrical discharge machining using shaped electrodes to form the mold 108 itself. More specifically, the shaped electrodes are formed to correspond to the desired shape of at least a portion of one of the exterior surfaces of the orthodontic appliance, such as the exterior surface that forms base 16. The shaped electrodes are then charged and placed in contact with a metal body that will form a portion of mold 108 for production of the actual orthodontic appliances. More specifically, the charged electrode "burns" the desired orthodontic appliance shape into the metal body, thus forming a portion of mold 108. The mold 108 is typically formed from a top and a bottom portion that is then assembled to form a hollow space that defines the contours of the orthodontic appliances to be formed in the mold. The mold 108 is then used to manufacture the orthodontic appliances by injecting the mold 108 with the suitable orthodontic material, such as molten stainless steel, via an injection channel that passes through mold 108 to the interior hollow region defining the appliance form. The molten stainless steel is allowed to cool and harden, and then the mold 108 is separated and the molded orthodontic appliance is subsequently ejected from the mold 108.

In order to adequately bond an orthodontic appliance (having a plurality of characters 94 formed in its base 16) to a tooth surface using an adhesive, the surfaces of the base 16 that are parallel to the tooth's surface are preferably relatively rough. However, if the surfaces of mold 108 corresponding to the base 16 of the orthodontic appliance are too rough, the appliance cannot be ejected from the mold 108 during the appliance's manufacturing process. Thus, in this separate aspect of the disclosure, the mold 108 is preferably manufactured and processed to have appropriate surficial roughness textures along its corresponding base surfaces so that the molded appliances easily release from the mold 108.

Figure 17:
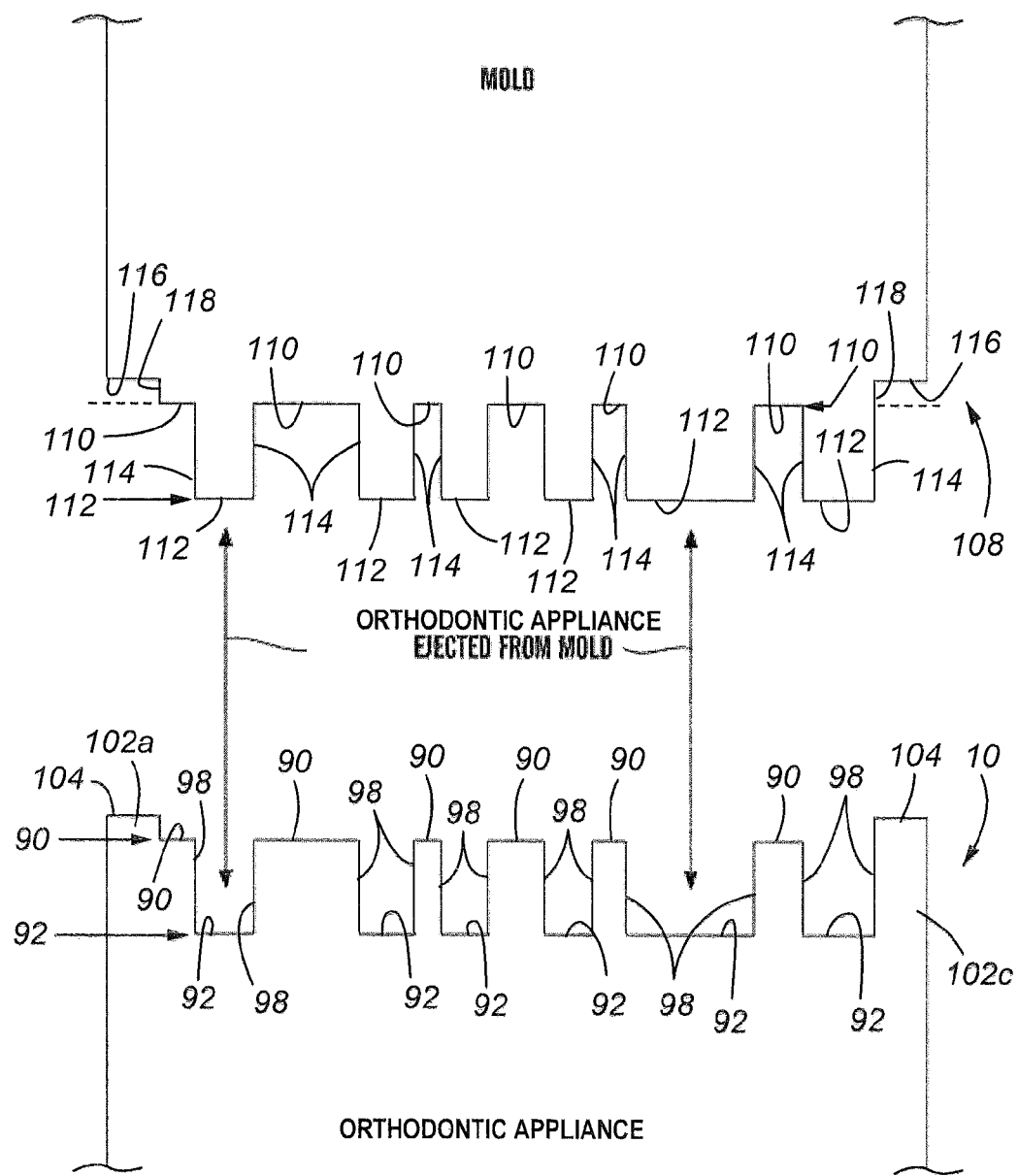
FIG. 17 is a cross-sectional view of the base of an orthodontic appliance having embedded informational characters therein, and a mold used to form the orthodontic appliance.

Referring now to FIG. 17, a mold 108 is shown having a base that includes mold recessed surface 110 and mold projected surface 112, which respectively correspond to the projected surface 90 and the recessed surface 92 of an orthodontic appliance to be manufactured. Preferably, mold recessed surface 110 and mold projected surface 112 have a surface finish of approximately a maximum of 110.8 micro-inches. In contrast, preferably the mold character walls 114 of mold 108 that form the generally sloped or perpendicular surfaces between characters 94 and intermediate spaces 96 of bracket 10 are polished. More specifically, the mold character walls 114 of mold 108 are preferably hand polished to a relatively smooth and polished finish, preferably using a ruby stone, although other means may be employed. Upon manufacture of an orthodontic appliance from mold 108, the hand polished character walls 114 of the mold 108 allow the appliance to be ejected from the mold 108 because the character walls 98 of the appliance are formed to have a smooth and polished finish that corresponds to the polished mold character walls 114 from which they were formed. Thus, a newly formed orthodontic appliance (e.g., the bracket 10) may be ejected from its mold 108 without sticking to the mold 108 and thereby preventing ejection from occurring, or bending or otherwise causing detrimental structural damage to the newly formed appliance during the ejection process. An ejector pin (not shown) may be used to aid the ejection process, wherein the ejection pin forcibly separates the newly formed orthodontic appliance from the mold 108 by pushing base 16 away from mold 108.

Where a perimeter rail is used, the mold 108 preferably includes a deeper recessed surface 116 corresponding to the perimeter rail surface 104. The deeper recessed surface 116 is surficially textured to provide texturing to the perimeter rail surface, which in turn improves bonding between the molded orthodontic appliance and the surface of the tooth. More particularly, the deeper recessed surface 116 of the mold 108 preferably has a surface finish of approximately a maximum of 110.8 micro-inches. In contrast, preferably the mold perimeter rail walls 118 of mold 108 are polished to a smooth finish to prevent a molded orthodontic appliance from sticking to the mold 108 during the ejection process, thereby preventing ejection or otherwise causing detrimental structural damage to the newly formed appliance during the ejection process.

Figure 18:
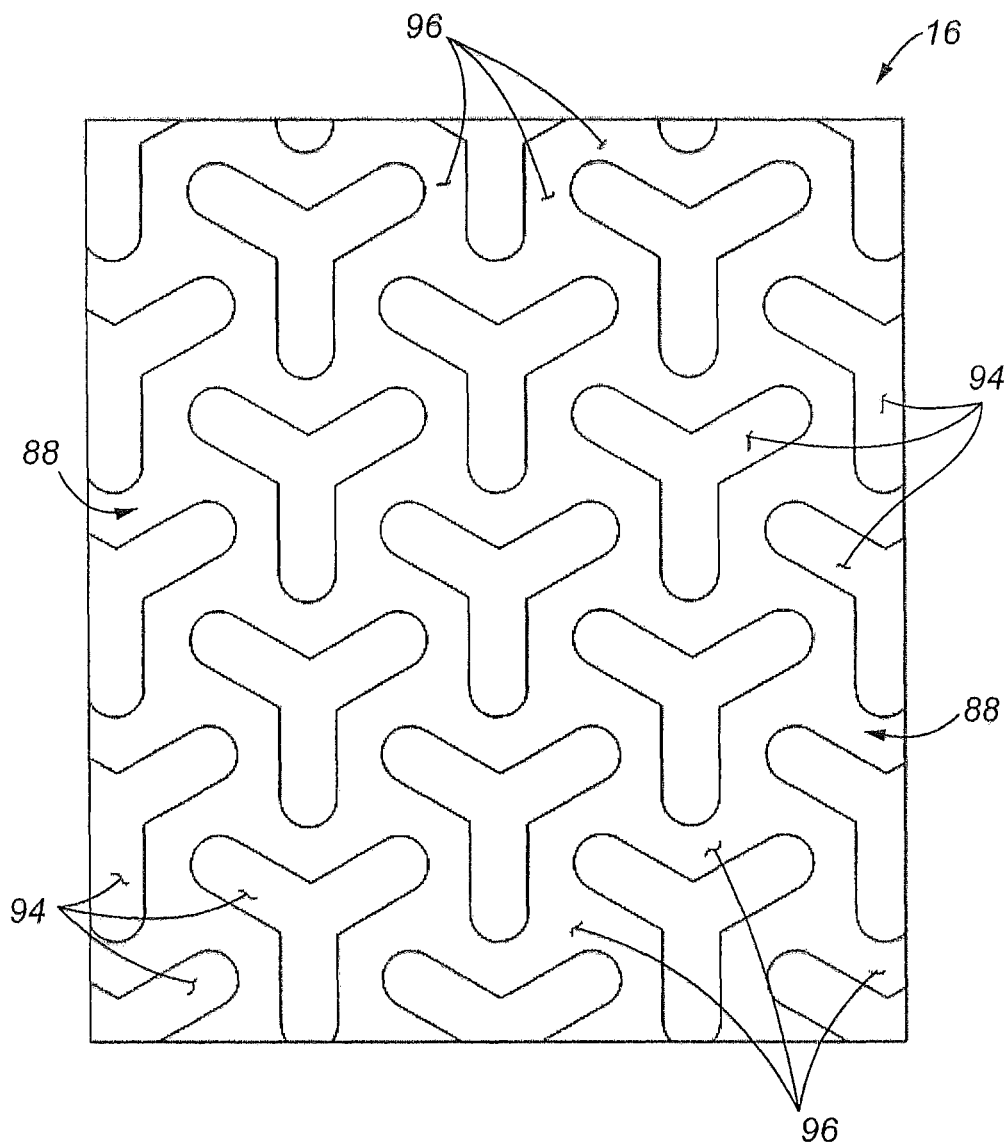
FIG. 18 is a separate embodiment of a pattern embedded into the base 16 of an orthodontic appliance.

Referring now to FIG. 18, an alternate aspect of the disclosure is shown. FIG. 18 presents a pattern of characters 94, wherein the characters are a three-pronged shape resembling the letter "Y". As in the previously described embodiments, intermediate space 96 surrounds the characters 94 within the interior region 88 of the base 16. Accordingly, the present disclosure contemplates the use of patterns of characters 94 wherein the character is a seemingly arbitrary shape, and one in which the base 16 possesses a projected surface 90 and a recessed surface 92. Brackets 10 that included patterns of characters 94 of shapes may further include discontinuous perimeter rail structures as described above.

Figure 19:
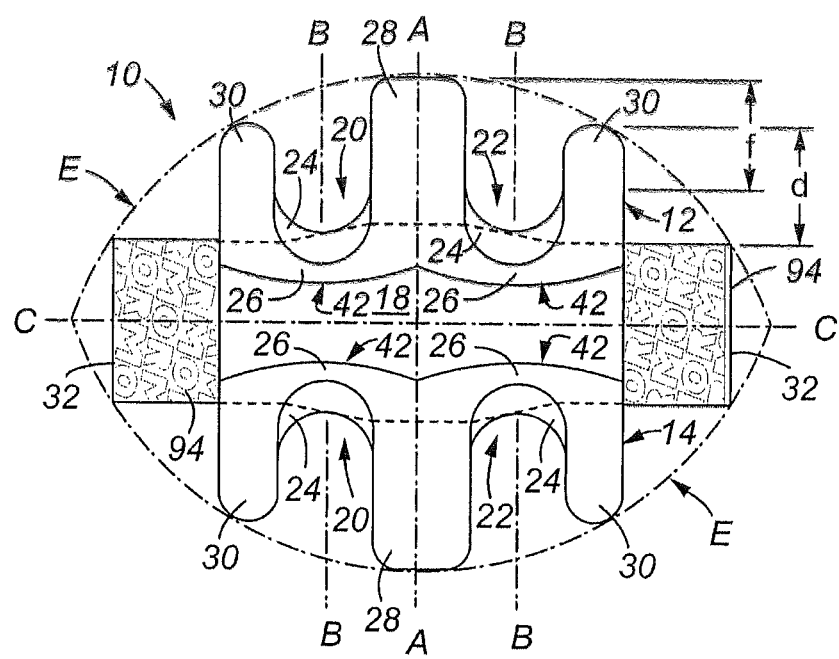
FIG. 19 is a labial view of a bracket having a labial positioned character pattern on its flange portions.

Referring now to FIG. 19, in a separate aspect of the disclosure, a pattern of characters 94 can be integrated into a side or labial position on an orthodontic appliance (e.g., the bracket 10 in FIG. 19). For example, as shown in FIG. 19, the flanges 32 can include a pattern of characters 94 such that the characters 94 are visible from a front view of the bracket 10 (more generally, orthodontic appliance). The pattern 94 could be a trademark of a manufacturer, a message, and/or the pattern 94 may be an ornamental or fanciful design.

In summary, the present disclosure is at least in part directed to a device and method for providing a pattern of characters on the base 16 of an orthodontic bracket. Such characters are preferably formed by creating a recessed pattern of the characters in the base, with the area between the characters raised, such that the area between the characters is closer to the tooth surface when the orthodontic appliance is applied to the surface of a patient's tooth using an adhesive. Alternatively, the characters may be raised and projecting relative to the area between the characters, such that the characters are closer to the tooth surface when the orthodontic appliance is attached to the surface of a patient's tooth.

In a separate aspect of the disclosure, a discontinuous perimeter rail may be used around the character pattern of the base 16. Preferably, the discontinuous perimeter rail includes four separate corner sections and two additional separate straight sections along the gingival and occlusal edges of the base 16. When used, the discontinuous perimeter rail projects beyond the patterned surface of the base, such that the discontinuous perimeter rail is closest to the tooth surface when the orthodontic appliance is attached to a patient's tooth. The discontinuous perimeter rail increases the bonding strength of the orthodontic appliance to the tooth's surface.

The pattern of characters and intermediate space formed on the base 16 of an orthodontic appliance provides a texturing pattern (e.g., an ordered array of projecting features) for bonding the orthodontic appliance to a patient's tooth using an adhesive, while at the same time providing a means of presenting information about the orthodontic appliance on its base surface by advantageously utilizing characters that represent pertinent information, such as the name of the appliance manufacturer, the intended location for the appliance placement, and/or a graphics symbol or logo.

In addition to providing information content on the orthodontic appliance base 16, the embedding of such information substantially increases the base total surface area to which the adhesive can adhere, thus resulting in a more effective bond between a patient's tooth and the orthodontic appliance. However, in some embodiments depending (e.g., on the viscosity of the adhesive), for the adhesive to effectively enter the recesses of the recessed surface 92, such recesses should have at least a minimal extent in two orthogonal directions. As described above, when the recessed portions are characters 94, a line width "lw" for such characters preferably ranges between about 0.008 to 0.010 inches, where line width lw (FIG. 16) is the width of the line forming each individual character 94. This constraint can be extended, wherein if a circle of diameter in the range of at least 0.008 inches were to be provided in all recessed portions and moved about therein the maximal extent possible, then the recessed area covered by the circle should be about at least 85% of the total recessed surface area. That is, only about 15% or less of the recessed surface area should be so confined by one or more walls 98 that this area could not be covered by the circle moving over the maximal extent of the recessed area possible. Note, this more general constraint is clearly shown at least in FIG. 16.

FIGS. 22 through 27 show various orthodontic appliances with bases 16 having encoded information embedded or formed in the bases, wherein the characters 94 are on the projected surface(s) 90 (e.g., as shown in FIGS. 9A and 9B), and the intermediary space 96 between the characters is provided on the recessed surface(s) 92 (e.g., as shown in FIGS. 9A and 9B). Note that the orthodontic appliances shown in these figures include both archwire slots, tubes, and hybrid combinations thereof. The tubes are identified by the label 204.

Figure 40A:
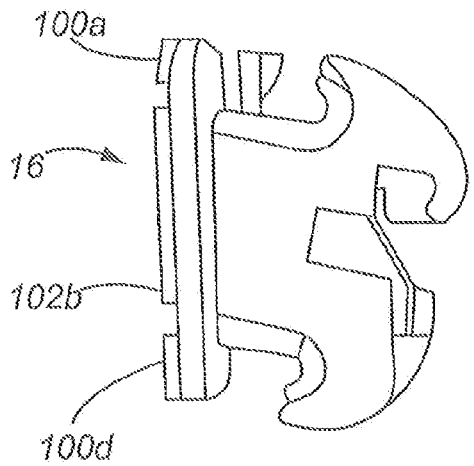
FIGS. 40A and 40B are different views of the same orthodontic appliance.
Figure 40B:
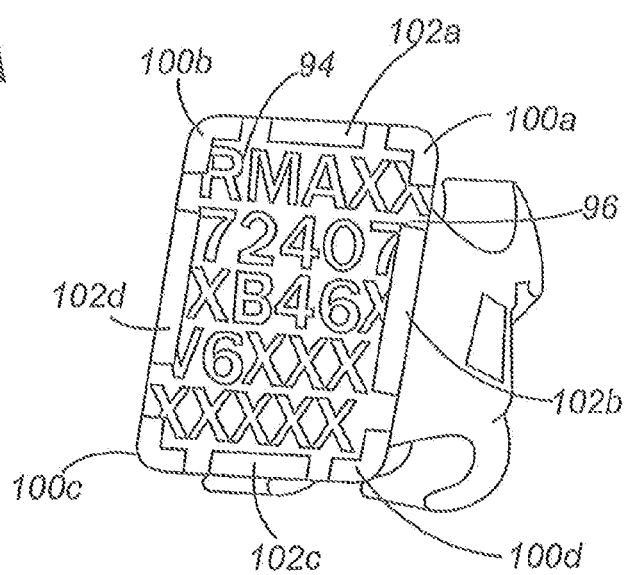
Figure 41:
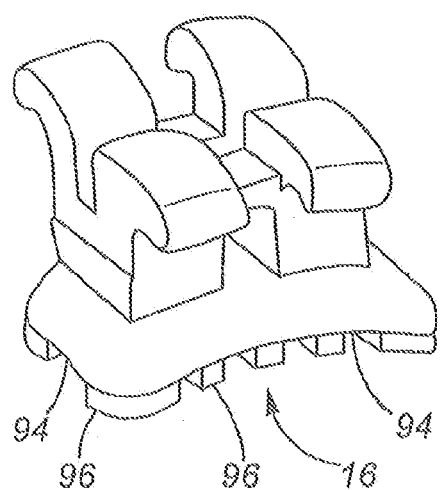

FIGS. 28 through 41 show various orthodontic appliances with bases 16 having encoded information embedded or formed therein, wherein the characters 94 are on the recessed surface(s) 90 (e.g., as shown in FIGS. 9A and 9B), and the intermediary space 96 between the characters is provided on the projected surface(s) 92 (e.g., as shown in FIGS. 9A and 9B). Note that for a given figure number, whenever there are figures A and B for the figure number, such figures A and B are different views of the same orthodontic appliance; e.g., FIGS. 40A and 40B are different views of the same orthodontic appliance. As with the FIGS. 22 through 27, that the orthodontic appliances shown in FIGS. 28 through 59 include both archwire slots, tubes, and hybrid combinations thereof, wherein the tubes are identified by the label 204. Moreover, it is worth mentioning that FIGS. 40A and 40B show an orthodontic appliance (a bracket), wherein the discontinuous perimeter rails of the base 16 further include rails 102b and 102d, respectively on the mesial and distal sides of the orthodontic appliance shown. Although, in general, such an embodiment may not be preferred, such a configuration for the perimeter rails is within the scope of the present disclosure.

The disclosure herein has been describes preferred embodiments of the invention claimed hereinbelow; however, other changes and modifications to the claimed invention may be made which are still contemplated within the spirit and scope of the present disclosure.

The foregoing disclosure has been provided for purposes of illustration and description. This disclosure is not intended to limit the invention claimed hereinbelow, and various embodiments thereof. Variations, embodiments and modifications will be apparent to those skilled in the art and are intended to be within the scope of the following claims

What is claimed is:

1. An orthodontic bracket, comprising:
    a body having a front and a back, the back for facing a tooth when the bracket is operably attached thereto, and the front having an archwire slot therein, the archwire slot having a length with at least a bottom, opposing sides, and an opening for providing an archwire therein, wherein the opening extends the length;
    a rotatable member for rotating relative to the body from an open position wherein the opening provides archwire access to operably position the archwire within the archwire slot, to at least one closed position wherein for each of the at least one closed position, at least a portion of the rotatable member inhibits the archwire from moving through the opening;
    wherein a first portion of the rotatable member is secured within a recess of the body, and rotates therein when the rotatable member rotates between the open position and the at least one closed position;
    wherein the rotatable member includes a slot cover external to the body so that in the open position the slot cover provides archwire access for positioning the archwire within the archwire slot, and in the at least one closed position the cover inhibits the archwire from moving through the opening, and wherein said slot cover comprises two slot coverable extensions that are substantially straight and bar shaped, each of said extensions having first and second sides that extend parallel to each other, and wherein, in said open position, said two slot coverable extensions are aligned parallel to each other and parallel to the opposing sides of the archwire slot, with a gap between the slot coverable extensions to allow an archwire to be passed therethrough, said rotatable member having an axis of rotation extending substantially directly beneath the archwire slot such that the axis of rotation of the rotatable member extends directly below and perpendicular to a longitudinal axis of the archwire when the archwire is positioned within the archwire slot, the archwire being positioned between the two slot coverable extensions when in the open position, and being restrained by the two slot coverable extensions when in the at least one closed position;
    wherein the at least one closed position comprises an active closed position and a passive closed position, said active closed position forcing said archwire into contact with a floor of the archwire slot with sufficient force to inhibit movement of the archwire in a direction along a length of the archwire slot;
    wherein upon rotation of the rotatable member, the first portion contacts predetermined discrete notches within the recess for positioning the rotatable member at corresponding predetermined angular orientations about an axis of rotation through the body.

2. The orthodontic bracket as set forth in claim 1, wherein said notches comprise from two to four notches.

3. The orthodontic bracket as set forth in claim 1, wherein said rotatable member is secured in said recess by at least one tab.

4. The orthodontic bracket as set forth in claim 3, wherein said at least one tab is biased by a spring.

5. The orthodontic bracket as set forth in claim 3, wherein said notches comprise from two to four notches.

6. The orthodontic bracket as set forth in claim 5, wherein said at least one tab is movable to engage with said two to four notches.

7. The orthodontic bracket as set forth in claim 5, wherein a stop wall is provided to prevent the at least one tab from rotating beyond an extent of said two to four notches.

8. An orthodontic bracket, comprising:
    a body having a front and a back, the back for facing a tooth when the bracket is operably attached thereto, and the front having an archwire slot therein, the archwire slot having a length with at least a bottom, opposing sides, and an opening for providing an archwire therein, wherein the opening extends the length;
    a rotatable member for rotating relative to the body from an open position wherein the opening provides archwire access to operably position the archwire within the archwire slot, to at least one closed position wherein for each of the at least one closed position, at least a portion of the rotatable member inhibits the archwire from moving through the opening;
    wherein a first portion of the rotatable member is secured within a recess of the body, and rotates therein when the rotatable member rotates between the open position and the at least one closed position;
    wherein the rotatable member includes a slot cover external to the body so that in the open position the slot cover provides archwire access for positioning the archwire within the archwire slot, and in the at least one closed position the cover inhibits the archwire from moving through the opening, and wherein said slot cover comprises two opposing slot coverable extensions each having a first linear side and a second irregularly shaped side, the first linear side of each of the two slot coverable extensions being substantially straight and extending parallel to each other, and wherein, in said open position, said first linear sides of the two slot coverable extensions are aligned parallel to each other and parallel to the opposing sides of the archwire slot, with a gap between the slot coverable extensions to allow an archwire to be passed therethrough, said rotatable member having an axis of rotation extending substantially directly beneath the archwire slot such that the axis of rotation of the rotatable member extends directly below and perpendicular to a longitudinal axis of the archwire when the archwire is positioned within the archwire slot, the archwire being positioned between the two slot coverable extensions when in the open position, and being restrained by the two slot coverable extensions when in the at least one closed position;
    wherein the at least one closed position comprises an active closed position and a passive closed position, said active closed position forcing said archwire into contact with a floor of the archwire slot with sufficient force to inhibit movement of the archwire in a direction along a length of the archwire slot;
    wherein upon rotation of the rotatable member, the first portion contacts predetermined discrete notches within the recess for positioning the rotatable member at corresponding predetermined angular orientations about an axis of rotation through the body.

9. The orthodontic bracket of claim 8, wherein the slot coverable extensions have an underside, convexly curved portion that faces the slot, said slot coverable extensions having a thicker portion at a first end of said slot coverable extensions and a thinner portion at an outer most end of the slot coverable extensions, wherein when the rotable member is rotated into the active closed position, the irregular shape of the slot coverable extensions increase the extent of the slot being covered by the slot coverable extensions.

10. The orthodontic bracket of claim 8, wherein the slot coverable extensions are fluted.

11. The orthodontic bracket of claim 8, wherein approximately twice the amount of the slot is covered by the extensions in the active closed position than in the passive closed position.

12. The orthodontic bracket of claim 8, wherein a slot opening coverage is in a range from 20% to 100% more slot coverage in the active closed position than in the passive closed position.

13. The orthodontic bracket of claim 8, wherein a slot opening coverage is at least 40% more slot coverage in the active closed position than in the passive closed position.

14. The orthodontic bracket of claim 8, further comprising locking tabs that lock into the notches for securing the rotatable member in the open position.

15. The orthodontic bracket of claim 8, wherein the rotatable member further includes a variable archwire stabilizer on an underside of the slot coverable extensions.

16. The orthodontic bracket of claim 8, wherein the rotatable member includes a ring that assists in maintaining proper orientation of the rotatable member when the rotatable member is rotated.

17. The orthodontic bracket of claim 16, wherein the ring is flexible to accommodate radial movement of locking tabs in and out of the notches.

18. The orthodontic bracket of claim 16, wherein the ring has threads on an inner cylindrical surface.

19. The orthodontic bracket as set forth in claim 8, wherein said rotatable member is secured in said recess by at least one tab.

20. The orthodontic bracket as set forth in claim 8, wherein said second irregularly shaped side of each of the two slot coverable extensions provides for an orthodontic receiving attachment area for grasping the rotatable member.

* * * * *